(12) United States Patent
Saeidi et al.

(10) Patent No.: US 8,338,570 B2
(45) Date of Patent: Dec. 25, 2012

(54) COLLAGEN FIBRILLAR CONSTRUCTION

(75) Inventors: Nima Saeidi, Allston, MA (US); Jeffrey W. Ruberti, Lexington, MA (US)

(73) Assignee: Northeastern University, Boston, MA (US)

(*) Notice: Subject to any disclaimer, the term of this patent is extended or adjusted under 35 U.S.C. 154(b) by 0 days.

(21) Appl. No.: 12/901,286

(22) Filed: Oct. 8, 2010

(65) Prior Publication Data

US 2011/0166325 A1 Jul. 7, 2011

Related U.S. Application Data

(63) Continuation of application No. PCT/US2009/040364, filed on Apr. 13, 2009.

(60) Provisional application No. 61/044,103, filed on Apr. 11, 2008, provisional application No. 61/045,439, filed on Apr. 16, 2008, provisional application No. 61/060,644, filed on Jun. 11, 2008.

(51) Int. Cl.
*C07K 1/36* (2006.01)
(52) U.S. Cl. ...................................... 530/356
(58) Field of Classification Search .................. None
See application file for complete search history.

(56) References Cited

U.S. PATENT DOCUMENTS

2005/0019488 A1* 1/2005 Braithwaite et al. .......... 427/240

OTHER PUBLICATIONS van der Rijt et al., "Micromechanical Testing of Individual Collagen Fibrils", Macromolecular Biosciences, 2006, vol. 6, No. 9, pp. 697-702.*
Hay et al., "Fine Structure of the Developing Avian Cornea," *Monogr. Dev. Biol.* 1:1-152 (1969).
Provenzano, P. and Vanderby, R. "Collagen fibril morphology and organization: Implications for force transmission in ligament and tendon," *Matrix Biol.* 25:71-84 (2006).
Marchini et al., "Ultrastructural Observations on Collagen and Proteoglycans in the Annulus Fibrosus of the Intervertebral Disc," *Basic Appl. Histochem.* 23:137-148 (1979).
Fini, M.E. and Stramer, B.M., "How the Cornea Heals: Cornea-Specific Repair Mechanisms Affecting Surgical Outcomes," *Cornea* 24:S2-S11 (2005).
Frank, C.B. "Ligament structure, physiology and function," *Musculoskelet. Neuronal Interact.* 4:199-201 (2004).
Lotz, J.D. and Kim, A.J., "Disc Regeneration: Why, When, and How," *Neurosurg. Clin. N. Am.* 16:657-663 (2005).
Ruberti, J.W. and Hallab, N.J., "Strain-controlled enzymatic cleavage of collagen in loaded matrix," *Biochem. Biophys. Res. Commun.* 336:483-489 (2005).
Bailey, A.J. and Rhodes, D.N, "Irradiation-Induced Crosslinking of Collagen," Radiation Res. vol. 22: 606-621 (1964).
Housley, T. et al., "Collagen Crosslinking: Isolation of Hydroxyaldol-Histidine," *Biochem. Biophys. Res. Commun.* 67:824-830 (1975).
Siegel, R. "Biosynthesis of Collagen Crosslinks: Increased Activity of Purified Lysyl Oxidase with Reconsistuted Collagen Fibrils," *Proc. Natl. Acad. Sci. U. S. A.* 71: 4826-4830 (1974).
Mechanic, G. and Tanzer, M., "Biochemistry of Collagen Crosslinking Isolation of a New Crosslink; Hydroxylysinohydroxynorleucine, and Its Reduced Precursor, Dihydroxynorleucine, From Bovine Tendon," *Biochem. Biophys. Res. Commun.* 41:1597-1604 (1970).
Shoshan, S. and Finkelstein, S., "Studies on collagen crosslinking in vivo," *Biochim. Biophys. Acta* 154(1): 261-263 (1968).
Guo, X. et al., "Morphologic Characterization of Organized Extracellular Matrix Deposition by Ascorbic Acid-Stimulated Human Corneal Fibroblasts," et al., Invest. Opthalmol. Vis. Science, vol. 48(9): 4050-4060 (2007).
Ren, R. et al. "Human Primary Corneal Fibroblasts Synthesize and Deposit Proteoglycans in Long-Term 3-D Cultures," *Dev. Dyn.* 237:2705-2715 (2008).
Meek, K.M. and Boote, C., "The organization of collagen in the corneal stroma," *Exp. Eye Res.* 78:503-512 (2004).
Trinkaus-Randall, V., et al., "Quantification of Stromal Destruction in the Inflamed Cornea," *Invest. Ophthalmol. Vis. Sci.* 32: 603-609 (1991).
Petroll, W.M. and Ma, L., "Direct, Dynamic Assessment of Cell-Matrix Interactions Inside Fibrillar Collagen Lattices," *Cell Motility and the Cytoskeleton*, vol. 55:254-264 (2003).
Wan, K-T, et al., "A theoretical and numerical study of a thin clamped circular film under an external load in the presence of a tensile residual stress,", *Thin Solid Films*, 425: 150-162 (2003).
Chaudhuri, B.B. et al., "Detection and gradation of oriented texture," Pattern Recognition Letters, vol. 14: 147-153 (1993).
Scott, J.E., "Proteoglycan Histochemistry—A Valulable Tool for Connective Tissue Biochemists," Coll. Relat. Res. 5:541-575 (1985).
Young, R.D. et al., "Keratan Sulfate Glycosaminoglycan and the Association with Collagen Fibrils in Rudimentary Lamellae in the Developing Avian Cornea,", *Invest. Ophthalmol. Vis. Sci.* 48: 3083-3088 (2007).
Brown, C. et al., "Extraction and purification of decorin from corneal stroma retain structure and biological activity," Protein Expr. Purif., vol. 25: 389-3999 (2002).
Dunlevy, J.R. and Rada, J., "Interaction of Lumican with Aggrecan in the Aging Human Sclera," *Invest. Ophthalmol. Vis. Sci.* 45:3849-3856 (2004).
Meek, K.M. and Quantock, A.J. "The Use of X-Ray Scattering Techniques to Determine Corneal Ultrastructure," *Prog. Retin. Eye Res.* 20:95-137 (2001).
Worthington, C.R. and Inouye, H., "X-Ray diffraction study of the cornea," *Intl. J. Biol. Macromolecules* 7: 2-8 (1985).
Quantock, A.J. et al., "An X-Ray Diffraction Investigation of Corneal Structure in Lumican-Deficient Mice," vol. 42(8): 1750-1756 (2001).
Birk, D. et al., "Collagen fibrollogenesis in vitro: interaction of types I and V collagen regulates fibril diameter," J. Cell Sci. 95:649-657 (1990).
Byers et al., "Interchain disulfide bonds in procollagen are located in a large nontriple-helical COOH-terminal domain," *Proc. Natl. Acad. Sci. U.S.A.* 72:3009-3013 (1975).
Church, et al. "Engineering the Future of Biology and Medicine," BMES Oct. 12, 2007 (4 pages).

(Continued)

*Primary Examiner* — Suzanne M Noakes

(74) *Attorney, Agent, or Firm* — Wilmer Cutler Pickering Hale & Dorr LLP.

(57) ABSTRACT

Methods and compositions are described for organizing collagen into fibrillar networks, e.g., short and long-range organization. Collagen produced by the disclosed methods can be used for tissue engineering.

15 Claims, 34 Drawing Sheets

OTHER PUBLICATIONS

Tzafriri, A.R. et al., "Reaction Diffusion Model of the Enzymatic Erosion of Insoluble Fibrillar Matrices," *Biophys. J.* 83:776-793 (2002).

Gelman, R.A. and Piez, K.A., "Collagen Fibril Formation in Vitro," *J. Biol. Chem.* 255:8098-8102 (1980).

Basser et al., "Mechanical Properties of the Collagen Network in Human Articular Cartilage as Measured by Osmotic Stress Technique," *Arch. Biochem. Biophys.* 351:207-219 (1998).

Verzijl, N. et al., "Crosslinking by Advanced Glycation End Products Increases the Stiffness of the Collagen Network in Human Articular Cartilage,", *Arthritis Rheum.* 46: 114-123 (2002).

Aquet et al., "Sub-resolution Axial Localization of Nanoparticles in Fluorescence Microscopy," Confocal, Multiphoton, and Nonlinear Microscopic Imaging II; 4 pages (2005).

* cited by examiner

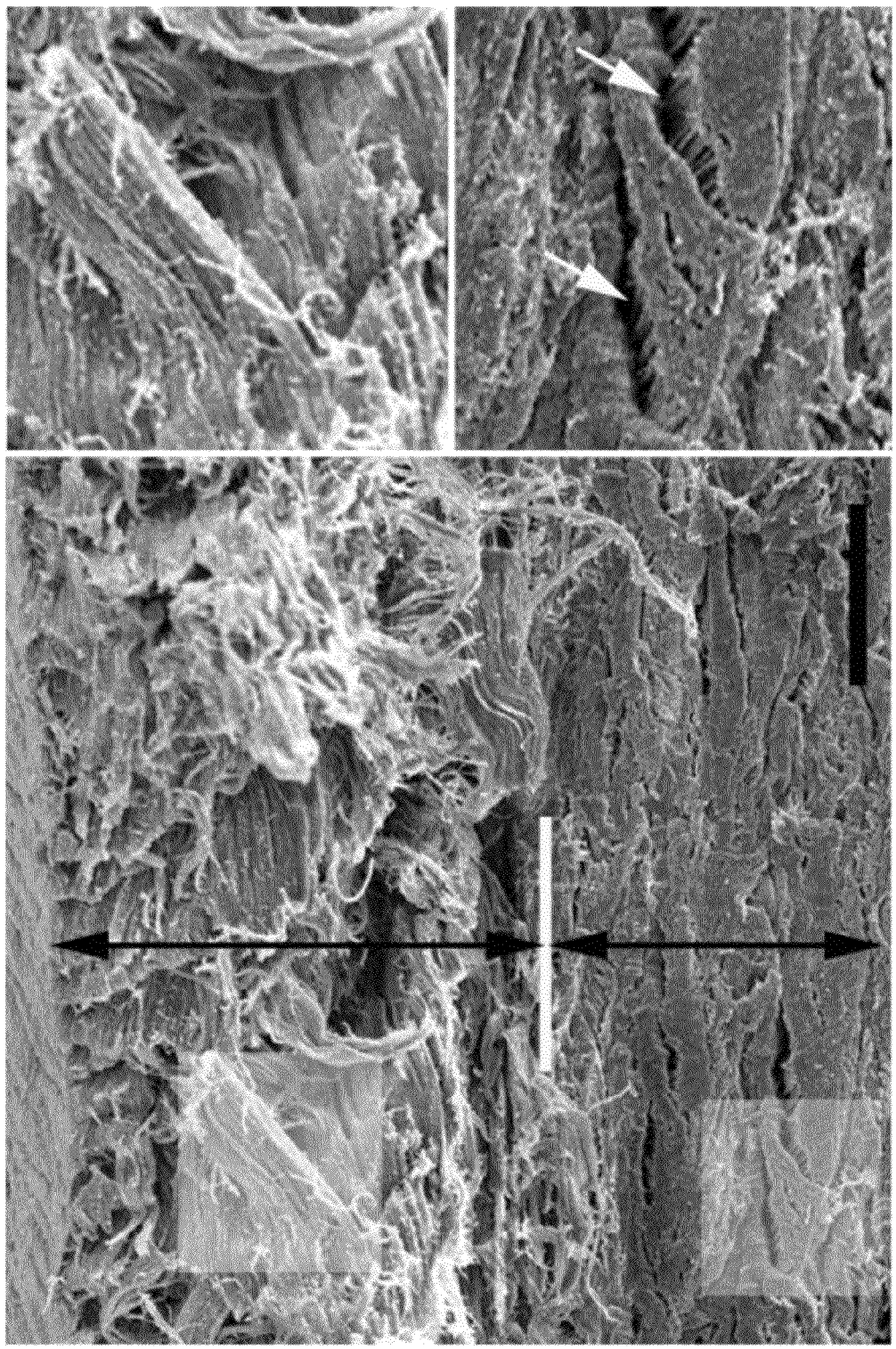

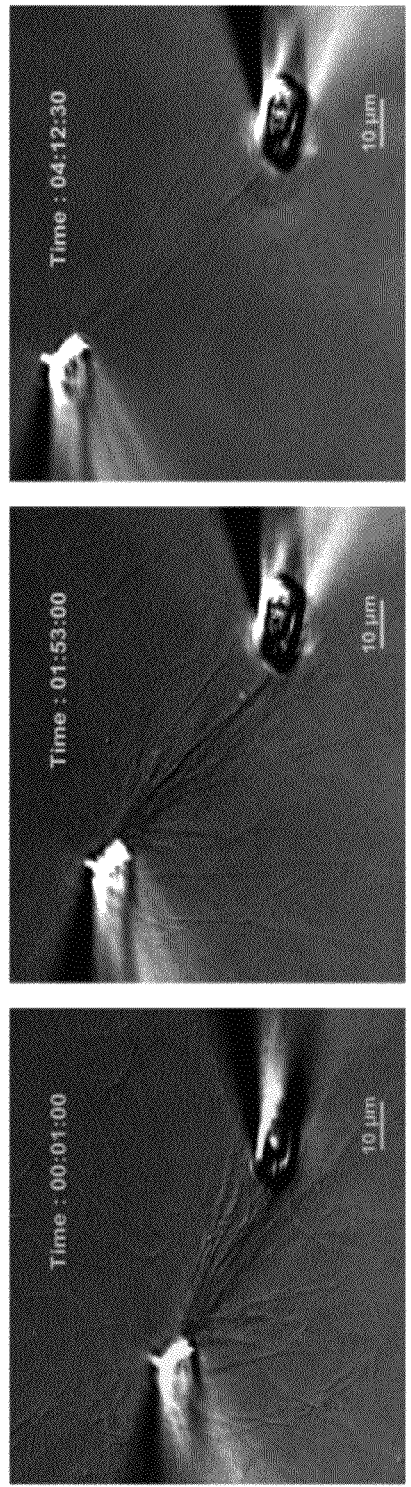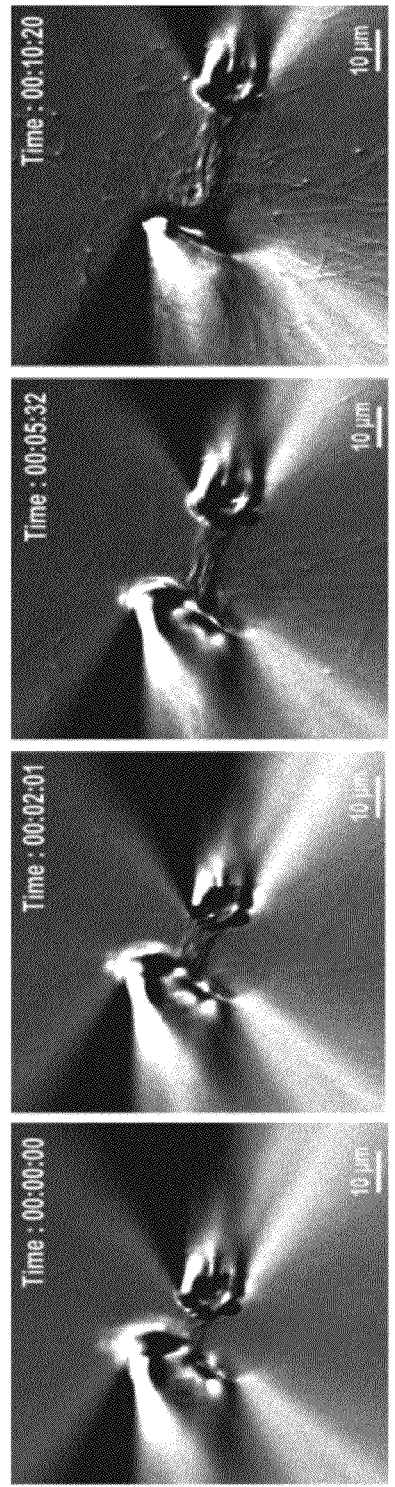

COLLAGEN FIBRILLAR CONSTRUCTION

CROSS-REFERENCE TO RELATED APPLICATIONS

This application is a continuation of International Application No. PCT/US2009/040364, filed Apr. 13, 2009, which claims the benefit of U.S. Provisional Application No. 61/044,103, filed Apr. 11, 2008, U.S. Provisional Application No. 61/045,439, filed Apr. 16, 2008, and U.S. Provisional Application No. 61/060,644, filed Jun. 11, 2008, the contents of all of which are hereby incorporated in their entirety herein.

STATEMENT REGARDING FEDERALLY SPONSORED RESEARCH OR DEVELOPMENT

This invention was made in part with government support under Grant No. 5R21AR053551-02, awarded by The National Institutes of Health. The United States government has certain rights in this invention.

FIELD OF THE INVENTION

The invention is in the fields of tissue engineering and medicine.

BACKGROUND OF THE INVENTION

Though significant effort has been expended to "tissue-engineer" natural grafts for the replacement of damaged or diseased load-bearing extracellular matrices (ECMs) such as ligament, tendon and cornea, no clinically viable constructs have been produced. One of the most difficult problems associated with engineering connective tissue (which typically begins with weak, self-assembled collagen-based scaffolds) is the achievement of adequate mechanical strength. The inability of such constructs to bear in vivo or near in vivo loads at the time of implantation has led to the development of methods which employ complex degradable high-strength scaffolds (e.g., silk) onto which fibroblastic cells are seeded. Once seeded, the fibroblasts in the matrix are stimulated (chemically and/or mechanically) to replace the resorbing scaffold material with a natural collagen-based matrix. This approach is hampered by uncertainties in the kinetics of the degradation and replacement process as well as the usual problems associated with the use of non-native biomaterials.

Collagen molecules comprise an epigenetically adaptable load-bearing matrix that can be culled by enzymatic degradation or reinforced by incorporation of monomers (longitudinally and in the radial direction). The generic ability of collagen-based matrices to add and remove monomers from fibrils is a remarkable feature of native load-bearing ECM, as are its mechanical properties (due to collagen's high tensile mechanical strength). Such tissue can be characterized by its highly anisotropic and ordered collagen fibrillar organization (cornea (Hay et al., *Monogr. Dev. Biol.* 1:1-144 (1969)), ligament and tendon (Provenzano et al., *Matrix Biol.* 25:71-84 (2006)), and annulus fibrosus (Marchini et al., *Basic Appl. Histochem.* 23:137-148 (1979)). Unfortunately, collagen has limited regenerative ability following injury (Fini et al., *Cornea* 24:S2-S11 (2005); Frank, *Musculoskelet. Neuronal Interact.* 4:199-201 (2004); Lotz et al., *Neurosurg. Clin. N. Am.* 16:657-663 (2005)).

Fibrillar collagen is the principal load-bearing molecule in vertebrate animals and the most abundant protein in vertebrates. The untimely failure of collagenous load-bearing tissues (which are often refractory to self-repair) due to degeneration, acute injury or collagen-related disease affects hundreds of millions of people world-wide and often can have a devastating impact on the quality of life of the individual if left untreated. In the industrialized world, degenerative disease of collagen-based tissue has a high prevalence. In the US, 32 million people over the age of 20 have frequent lower back pain; the majority of these cases are likely the result of intervertebral disc degeneration. The cost of indirect and direct medical care for herniated disks was estimated to be $1.6 B in 1995. Osteoarthritis, a degenerative cartilage pathology of unknown etiology, affects over 20 million US adults and is second only to chronic heart disease as the reason for long-term disability payment requests. Acute injury to connective tissue also contributes significantly to the loss of load-bearing tissue function. There are 200,000 anterior cruciate ligament (ACL) injuries and between 60,000 and 95,000 ACL reconstructions are performed each year in the US to restore mechanical function.

There also are a constellation of collagen-related diseases due to genetic mutations which include Ehlers-Danlos syndrome, Bethlem myopathy, Alport syndrome, Knobloch syndrome, osteoporosis (some cases), osteogenesis imperfecta, arterial aneurysm and rheumatoid arthritis (autoimmune).

Very little is known about the mechanisms which govern the organization and morphology of collagen during synthesis by fibroblasts in vivo, for it is the loss of or damage to organized collagen that is often irreparable. The majority of tissue engineers have opted to investigate synthetic biomaterials and have, with few exceptions, treated collagen as a "degradable" cell transport vehicle. There are more than 10 million cases of corneal blindness (caused by both injury and disease), the vast majority of which could benefit from suitable corneal replacement. In the US, 33,000 corneal transplants are performed each year in the US; however, recipients will be subject to a looming graft material shortage induced by the extensive use of LASIK corrective surgery, which renders corneas unsuitable for donation.

SUMMARY OF THE DISCLOSURE

The disclosure is based, at least in part, on the discovery that collagen monomers can be organized into long-range fibrillar networks by confining solutions of concentrated collagen monomers within templates. Accordingly, in one aspect, the disclosure features a method of producing an organized array of collagen fibrils. The method includes contacting a template with a still solution comprising collagen monomers in liquid crystalline phase; and neutralizing the solution in contact with the template, thereby inducing the assembly of the collagen monomers into an organized array of collagen fibrils.

In some embodiments, the collagen monomers comprise a nematic phase. In other embodiments, the collagen monomers comprise a smectic phase. In yet other embodiments, the collagen monomers comprise a cholesteric phase.

In certain embodiments, the solution comprises about 30 mg/ml to about 1000 mg/ml collagen monomers, about 30 mg/ml to about 500 mg/ml, about 40 mg/ml to about 400 mg/ml, about 50 mg/ml to about 300 mg/ml, about 60 mg/ml to about 200 mg/ml, about 70 mg/ml to about 150 mg/ml, about 80 mg/ml to about 125 mg/ml, about 90 mg/ml to about 120 mg/ml, or about 100 mg/ml collagen monomers.

In some embodiments, the method includes neutralizing the solution by adjusting the solution to a pH of about 5 to about 10, about 5.5 to about 9.5, about 6 to about 9, about 6.5 to about 8.5, or about 6.5 to about 8.

In other embodiments, the method includes neutralizing the solution in contact with the template at about 10° C. to about 39° C., at about 10° C. to about 35° C., about 15° C. to about 30° C., or about 20° C. to about 25° C.

In certain embodiments, the method further comprises applying an electric charge to the template.

In particular embodiments, the template comprises one or more guidance structures. In specific embodiments, the one or more guidance structures are one or more internal guidance structures and the template is placed in a stationary position within the solution. In some embodiments, the guidance structures comprise a surface having a pattern of hydrophobic and hydrophilic stripes.

In other embodiments, the one or more internal guidance structures comprise a high aspect ratio geometry. In particular embodiments, the one or more internal guidance structures comprise a minor length scale of between about 14 nm and about 20 µm, for example, between about 20 nm and about 15 µm, between about 25 nm and about 10 µm, between about 30 nm and about 5 µm, between about 40 nm and about 100 nm, between about 50 nm and about 90 nm, between about 60 nm and about 80 nm, or about 70 nm.

In some embodiments, one or more of the internal guidance structures comprise a biodegradable material. In certain embodiments, the biodegradable material is silk, PLGA, or a PLA-type material (such as PDLA, PLLA, or PDLLA).

In yet other embodiments, the template comprises a plurality of external guidance structures. In some embodiments, the external guidance structures have an interstructure distance of about 2 µm to about 200 µm, for example about 4 µm to about 175 µm, about 8 µm to about 150 µm, about 10 µm to about 125 µm, about 20 µm to about 100 µm, about 30 µm to about 90 µm, about 40 µm to about 80 µm, or about 50 µm to about 70 µm. In some embodiments, the template comprises one or more internal guidance structures and one or more external guidance structures.

In certain embodiments, the template comprises a cylindrical tube, two concentric cylindrical tubes, or two concentric hemispheres. In some embodiments, the template comprises a cylindrical tube having an inner diameter of about 100 µm to about 1 mm, for example about 125 µm to about 900 µm, about 150 µm to about 800 µm, about 175 µm to about 700 µm, about 200 µm to about 600 µm, about 300 µm to about 500 µm, or about 400 µm to about 450 µm. In other embodiments, the template comprises two concentric cylinders with a gap width of about 2 µm to about 4 mm, for example, about 4 µm to about 2 mm, about 8 µm to about 1 mm, about 10 µm to about 900 µm, about 20 µm to about 800 µm, about 30 µm to about 700 µm, about 40 µm to about 600 µm, about 50 µm to about 500 µm, about 100 µm to about 400 µm, or about 200 µm to about 300 µm. In yet other embodiments, the template comprises two concentric hemispheres with a gap width of about 2 µm to about 4 mm, for example, about 4 µm to about 2 mm, about 8 µm to about 1 mm, about 10 µm to about 900 µm, about 20 µm to about 800 µm, about 30 µm to about 700 µm, about 40 µm to about 600 µm, about 50 µm to about 500 µm, about 100 µm to about 400 µm, or about 200 µm to about 300 µm.

In some embodiments, the template comprises a scaffold that mimics a cornea, a ligament, a tendon, a meniscus, an intervertebral disk, or articular cartilage.

In certain embodiments, the collagen monomers are selected from the group consisting of Type I collagen monomers, Type II collagen monomers, Type III collagen monomers, Type V collagen monomers, Type XI collagen monomers, an MMP-resistant mutant thereof, and combinations thereof. In other embodiments, the collagen monomers are selected from the group consisting of atelo-collagen monomers, tropocollagen monomers, procollagen monomers, and combinations thereof.

In particular embodiments, the solution comprises a buffer or salt selected from the group of $CaCl_2$, NaOH, NaCl, $Na_2HPO_4$, $NaHCO_3$, Hepes, PBS, Trizma base, Tris-Hcl, cell culture media, and combinations thereof.

In yet other embodiments, the solution comprises one or more co-nonsolvency agents. In certain embodiments, the co-nonsolvency agent is polyethylene glycol, hyaluronic acid, a glycosaminoglycan, a proteoglycan, or a combination thereof. In some embodiments, the glycosaminoglycan is chondroitin sulfate, hyaluronic acid, heparin, heparin sulfate, keratin sulfate, or dermatan sulfate.

In other embodiments, the solution further comprises a collagen binding agent. In some embodiments, the collagen binding agent is a proteoglycan, a glycoprotein, a collagen-binding portion thereof, or a combination thereof. In certain embodiments, the proteoglycan is lumican, decorin, biglycan, perlecan, versican, fibromodulin, aggrecan, sydecan or a combination thereof. In other embodiments, the glycoprotein is fibronectin, laminin, osteonectin, or a combination thereof.

In yet other embodiments, the organized array of collagen fibrils is about 100 µm to about 30 cm in length, for example, about 200 µm to about 20 cm, about 400 µm to about 10 cm, about 500 µm to about 5 cm, about 750 µm to about 1 cm, about 1 mm to about 500 mm, about 10 mm to about 400 mm, about 50 mm to about 300 mm, about 100 mm to about 200 mm, or about 100 mm to about 150 mm.

In some embodiments, the organized array of collagen fibrils comprises D-banded collagen fibrils.

In certain embodiments, the method further comprises contacting the collagen monomers in the organized array of collagen fibrils with a crosslinking agent. In some embodiments, the crosslinking agent is formaldehyde, hexamethylene diisocyanate, glutaraldehyde, a polyepoxy compound, gamma irradiation, ultraviolet irradiation with riboflavin, transglutaminases, acyl azidesglycidyl ethers, diisocyanates, hexamethylenediisocyanate, bis-epoxide, carbodiimide, dimethylsuberimidate, nordihydroguaiaretic acid, lysyl oxidase, or a combination thereof.

In other embodiments, the method further comprises modulating the surface energy of the guidance structures. In some embodiments, the surface energy is modulated by plasma cleaning, silanization, or hydrophobic/hydrophilic bonding.

In some embodiments, the method further comprises organizing the array of collagen fibrils into a structure mimetic of a load-bearing tissue by contacting the array with a secondary template. In certain embodiments, the secondary template comprises cells, such as primary fibroblasts or stem cells, and forms a load-bearing tissue of a given morphology.

In another aspect, the invention features a method of producing an organized array of collagen fibrils. The method comprises contacting a template with a solution comprising collagen monomers to form collagen fibrils in the solution; applying tension to a plurality of collagen fibrils in the solution, where the tension produces a strain of about 1% to about 20%; and contacting the collagen fibrils with a collagen lytic protease; thereby producing an organized array of collagen fibrils from the plurality of collagen fibrils by selective removal of fibrils with lower strain. In some embodiments, applying tension to the plurality of collagen fibrils protects the plurality of collagen fibrils from enzymatic degradation by the collagen lytic protease.

In some embodiments, the collagen lytic protease is a bacterial collagenase, a matrix metalloproteinase (MMP), cathepsin K, or a biologically active fragment thereof.

In some embodiments, the method further comprises neutralizing the solution in contact with the template. In certain embodiments, the method includes neutralizing the solution by adjusting the solution to a pH of about 5 to about 10, for example, about 5.5 to about 9.5, about 6 to about 9, about 6.5 to about 8.5, or about 6.5 to about 8. In other embodiments, the method includes neutralizing the solution in contact with the template at about 10° C. to about 39° C., for example, at about 10° C. to about 35° C., about 15° C. to about 30° C., or about 20° C. to about 25° C.

In certain embodiments, the tension produces a fibril strain of about 1% to about 20%, for example, about 1% to about 10%, about 1% to about 9%, about 2% to about 8%, about 3% to about 7%, or about 4% to about 6%. In other embodiments, the tension produces a strain of about 1%, about 2%, about 3%, about 4%, about 5%, about 6%, about 7%, about 8%, about 9%, or about 10%.

In some embodiments, the tension is applied to the fibrils in a constant manner. In other embodiments, the tension is applied to the fibrils in an oscillatory manner. In particular examples, the tension produces an oscillatory strain of about 1% to about 10% amplitude on the fibrils. In certain embodiments, the tension produces an oscillatory strain at a frequency of about 0.1 Hz to about 5 Hz, for example, about 0.2 Hz to about 4 Hz, about 0.3 Hz to about 3 Hz, or about 0.5 Hz to about 2 Hz.

In certain embodiments, the tension is applied to both ends of the plurality of collagen fibrils.

In other embodiments, the method further comprises adding supplemental collagen monomers to the solution after tension is applied. In some embodiments, the collagen lytic protease and the supplemental collagen monomers are added simultaneously to the solution. In other embodiments, the collagen lytic protease and the supplemental collagen monomers are added sequentially to the solution. In yet other embodiments, the collagen lytic protease and the supplemental collagen are added more than once to the solution.

In some embodiments, the method further comprises organizing the array of collagen fibrils into a tissue.

In another aspect, the invention features an organized array of collagen fibrils produced by any of the methods described herein.

In another aspect, the invention features a method of directing the assembly of collagen fibrils. The method comprises contacting a template with a still solution comprising collagen monomers in liquid crystalline phase, the template comprising a plurality of guidance structures; and neutralizing the solution in contact with the template; wherein contacting the template directs the assembly of the collagen monomers in a pattern or direction defined by the guidance structures.

The following figures are presented for the purpose of illustration only, and are not intended to be limiting.

BRIEF DESCRIPTION OF THE DRAWINGS

FIG. 6A is a representation of a SEM micrograph of fractured cross-section of collagen in high-concentration de novo construct, and insets depict a clear change of direction in highly-aligned collagen fibrils in lamellae, where lower black arrow indicates fibrils that are cut in cross-section that are densely packed and that appear to be "solid," and bar is 10μ.

FIG. 20A is a representation of a DIC image of degradation of a reconstituted collagen gel by MMP-8 at time 00:01:00.

FIG. 20B is a representation of a DIC image of degradation of a reconstituted collagen gel by MMP-8 at time 01:53:00.

FIG. 20C is a representation of a DIC image of degradation of a reconstituted collagen gel by MMP-8 at time 04:12:30.

FIG. 21A is a representation of a DIC image of growth of a loaded cluster of reconstituted collagen fibrils at time 00:00:00.

FIG. 21B is a representation of a DIC image of growth of a loaded cluster of reconstituted collagen fibrils at time 00:02:01.

FIG. 21C is a representation of a DIC image of growth of a loaded cluster of reconstituted collagen fibrils at time 00:05:32.

FIG. 21D is a representation of a DIC image of growth of a loaded cluster of reconstituted collagen fibrils at time 00:10:20.

Figure 1A:
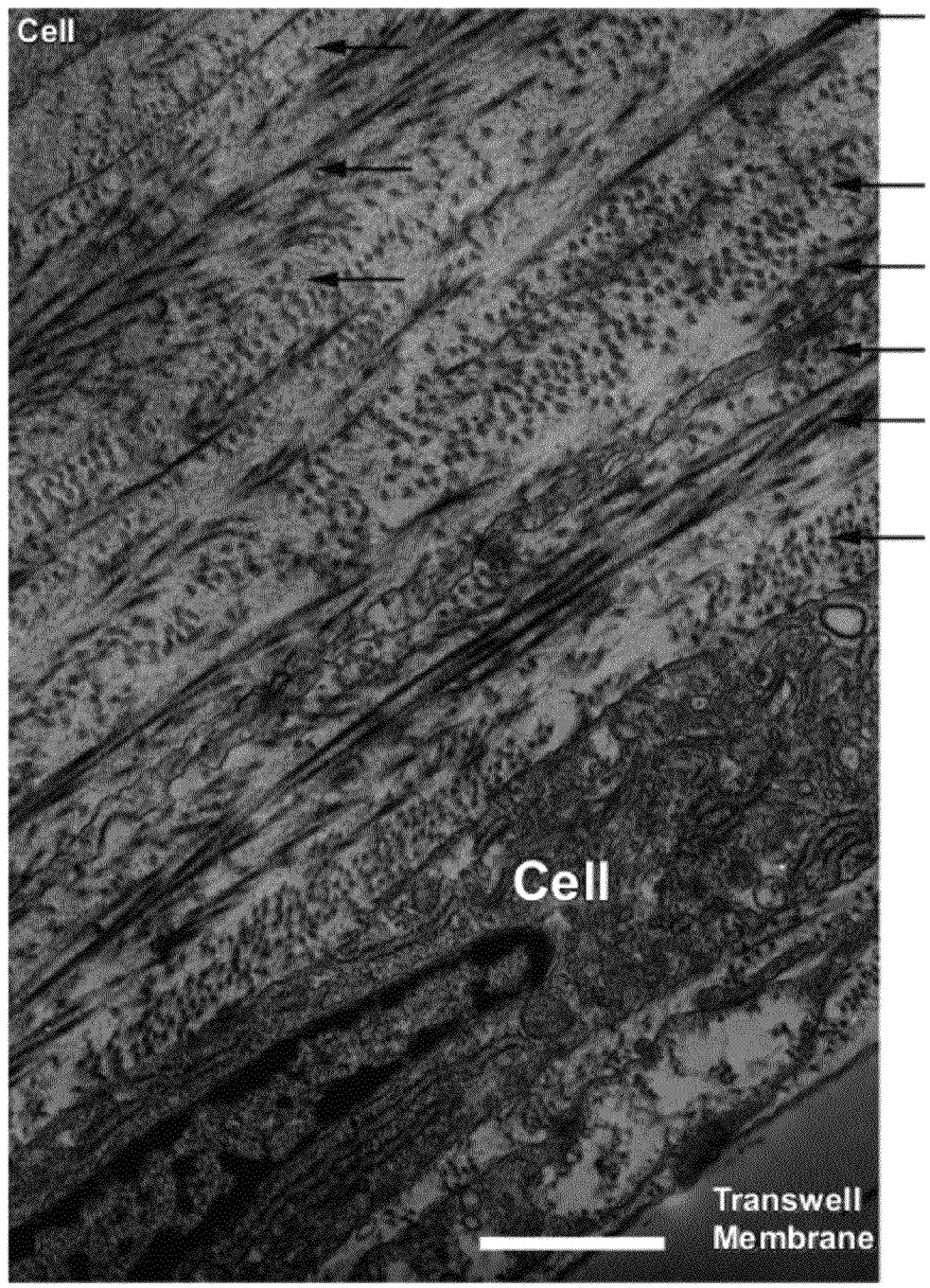
FIG. 1A is a representation of a TEM micrograph of organized, alternating collagen lamellae deposited by human primary corneal fibroblasts in vitro at 28 days where bar is 2μ. Fibril direction changes in the human culture system are indicated by the black arrows; Col=collagen; fl=flocculent material.

Other features and advantages of the invention will be apparent from the following detailed description, and from the claims.

DETAILED DESCRIPTION OF THE INVENTION

Although methods and materials similar or equivalent to those described herein can be used in the practice or testing of the present invention, suitable methods and materials are described below. All publications, patent applications, patents, and other references mentioned herein, including Gen- Bank database sequences, are incorporated by reference in their entirety. In case of conflict, the present specification, including definitions, will control. In addition, the materials, methods, and examples are illustrative only and not intended to be limiting.

Unless otherwise defined, all technical and scientific terms used herein have the same meaning as commonly understood by one of ordinary skill in the art to which this invention belongs.

Definitions

As used herein, a "template" is a three-dimensional structure or substrate that controls collagen fibril organization. A template creates a zone of local influence within a solution of collagen. A template comprises one or a plurality of guidance structures.

As used herein, a "guidance structure" is a structure with a high aspect ratio with a minor length scale of between about 14 nm and about 20 µm. The guidance structure is defined by the operative length scale of a collagen monomer.

Ranges may be expressed herein as from "about" one particular value, and/or to "about" another particular value. The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

As used herein, "interstructure distance" means the distance between the outer surfaces of two adjacent guidance structures.

As used herein, "alignment" in reference to collagen fibrils means that most of the fibrils in the same radial plane in a tube wall run roughly parallel to each other. It is not meant that every fibril must be parallel to every other fibril in the plane, but that a general alignment pattern must be discernable.

As used herein, a "fibril" is an association of several collagen monomers into a structure that appears fibrous with suitable magnification.

As used herein, "collagen" means a protein component of an extracellular matrix having a tertiary structure that includes polypeptide chains intertwining to form a collagen triple helix or having a characteristic amino acid composition comprising Gly-X-Y repeat units, or a fragment thereof. Collagens can be any collagen known in the art (e.g., one of collagen Type 1-29).

General

The methods described herein are based, at least in part, on the discovery that collagen and its complement matrix and enzymes form the basis of a "smart" engineering material on multiple levels, including the ability to self-organize over both short and long length scales. Aligned layers of collagen fibrils can be produced by precipitating fibrils from liquid crystalline collagen. The precipitated monomers can produce naturally load bearing fibrillar structures. As the thickness of the sample can be controlled, the methods described herein can be used in artificial tissue engineering, e.g, to produce both the short and long-range organization and morphology of collagen in highly-anisotropic native tissues such as tendon, ligament, bone, annulus fibrosus and cornea. Further, the absence of toxic material in the methods described herein can result in a biocompatible construct. Finally, the collagen produced by the methods described herein has much higher mechanical strength compared to regular collagen gels.

Collagen

The methods described herein can be used to produce organized collagen, e.g, to engineer tissues. Collagen is the most abundant protein in the extracellular matrix (ECM) of vertebrates and is the most common structural molecule in tensile load-bearing applications.

More than 29 different collagenous sequences are known. Fibrillar collagens (e.g., Types I, II, III, V and XI) are the principal structural component in load-bearing extracellular matrix (ECM), which provides a network for cells to interact and form three dimensional, multi-cellular organisms. Collagen possesses a linear-helical structure comprising three left-handed helical alpha chains whose complementary amino acid sequence results in the formation of a right-handed supramolecular triple helix. Collagen contains the repetitive sequence amino acid sequence Gly-X-Y, where X and Y are usually proline and hydroxyproline, respectively.

As described herein, collagen is not a passively manipulated element, but rather a principal component in a cooperative engineering material system, a system that significantly enhances the ability of fibroblastic cells to produce and optimize load-bearing tissue.

Any known collagen can be used in the methods described herein and can be isolated or derived from a natural source, manufactured biochemically or synthetically, produced through genetic engineering, or produced through any other means or combinations thereof. In addition, collagen is commercially available (e.g, from Inamed Biomaterials, Fremont, Calif.; and FibroGen, Inc., San Francisco, Calif.). Natural sources include, but are not limited to, collagens produced by or contained within the tissue of living organisms (e.g, cows, pigs, birds, fish, rabbits, sheep, mice, rats, and humans). Further, natural collagen can be obtained from, for example, tendons, bones, cartilage, skin, or any other organ by any known extraction method. Exemplary sources include rat tail tendon and calf skin.

Some collagens that are useful in the methods described herein include, but are not limited to, collagen Types I, II, III, IV, V, VI, VII, VIII, IX, X, XI, XII, XIII, XIV, XV, XVI, XVII, XVIII, and XIX. Synthetic collagen can include collagen produced by any artificial means, and numerous methods for producing collagens and other proteins known in the art can be used. For example, synthetic collagen can be prepared using specific sequences, such as specific amino acids that are the same or that differ from natural collagen. Engineered collagen can be produced by any method known in the art including, for example, polypeptide synthesis.

Structural Arrangement of Collagen in Native Load-Bearing ECMs

The mechanics of native collagenous matrices are based on the nanoscale organization of the collagen fibrils. With the exception of bone (due to its unique remodeling mechanism comprising Haversion systems), the structure of load-bearing tissues is "set" during development and does not appreciably change in the general long-range organization in the adult. There are principally two organizational regimes depicted for the collagen fibrils: 1) uniaxial prismatic cylinders, and 2) uniaxial sheets or "lamellae". In the case of the latter, 3-dimensional structures are "built-up" by successive layering of these lamellae in stacks where the angle between lamellae is changed. The stacks can be formed in concentric cylinders (such as in lamellar and osteonal bone, annulus fibrosus) or nested hemispheres (such as in cornea). These structures are actually 2-D (plus) and are naturally optimized for bearing tension in the plane of the lamellae (such as in cornea) or for resisting torsion (such as in annulus fibrosus).

Methods of Organizing Collagen

Concentrating and Precipitating Collagen

In some instances, the methods described herein include confining a solution of collagen monomers within a template having a defined confinement geometry (e.g, having defined external guidance structures). The solution can include any type of collagen monomers. However, certain methods utilize the same type of collagen as the collagen that mainly constitutes a particular tissue of interest. For example, for skin, bones, and tendons, Type I collagen can be used; for cartilage, Type II can be used; and for skin and muscles, Type III can be used.

The collagen in solution can be in a liquid crystalline phase, e.g., in nematic, smectic, or cholesteric phase. In certain instances, the concentration of collagen monomers in the solution is between about 30 mg/ml and about 500 mg/ml. In other instances, the collagen solution includes a buffer. Examples of buffers include, without limitation, $CaCl_2$, NaOH, NaCl, $Na_2HPO_4$, $NaHCO_3$, Hepes, PBS, Tris, cell culture media, and combinations thereof.

By confining the solution of collagen monomers within external guidance structures, the collagen monomers are induced to precipitate and to form collagen arrays having a desired tissue architecture. In one exemplary method, collagen monomers are concentrated to about 100 mg/ml and are confined between featureless planar glass coverslips separated by about 40µ, leading to fibril precipitation from the solution with a high-degree of alignment in planes parallel to the coverslips. In this situation, the coverslips provide external guidance structures that induce the alignment of the fibrils. Further, the collagen fibrils can form layers in which the orientation of the alignment of the fibrils can change direction, forming a natural load-bearing structure similar to native collagen organization found in cornea, bone, blood vessel intima or adventitia, and annulus fibrosus. Thus, the concentration and confinement of collagen in axially symmetric geometries can result in the formation of structures similar to any collagenous tissue, such as ligament or tendon.

In other methods, the local organization of collagen is controlled by using internal templates (e.g., internal guidance structures). While not wishing to be bound by theory, it is believed that such internal templates mimic embedded fibroblasts (or fibroblast filipodia) to influence the local organization of collagen fibrils. In certain instances, the internal template is made of a biodegradable polymer. Nonlimiting examples of biodegradable polymers include silk, poly(lactide), poly(glycolic acid), poly(lactide-co-glycolide), poly(caprolactone), polycarbonates, polyamides, polyanhydrides, polyamino acids, polyortho esters, polyacetals, polycyanoacrylates, and degradable polyurethanes.

In one exemplary method, an internal template is made of fine degradable filaments that are woven into a sparse scaffold. The scaffold can then be immersed in a solution of concentrated collagen monomers, which induces the alignment of the precipitating collagen to follow the internal template. The spacing and size of the internal template (e.g., biodegradable filaments) can be arranged to result in a particular collagen fibrillar organization of interest. Thus, the use of internal guidance structures allows internal control over the organization of collagen, such as solutions of collagen monomers confined within a particular geometry (e.g, within external guidance structures).

Modifying External and Internal Templates

The external and internal templates (e.g., external and internal guidance structures) can be modified to influence the collagen fibrillar organization. For example, using known methods, the surfaces of the external and internal templates can be plasma cleaned, patterned, or functionalized in other ways to control the local organization of the interfacing fibrils to produce collagen arrays. In particular methods, the surfaces of the external and/or internal templates are silanated or carbodiimidated using known methods.

In some instances, the surface charges of collagen molecules can be used to direct the process of collagen assembly by applying an electric charge to one or more surfaces of the external and/or internal templates. In particular methods, collagen molecules can be confined between two metallic plates containing an electrical field to direct the assembly of collagen. In other situations, the amount of free ion charges in the solution can be altered to change the degree of variation in alignment between layers.

Auxiliary Molecules

The methods described herein can include the use of one or more auxiliary molecules, e.g., collagen modulating molecules such as extracellular matrix molecules. Such molecules include, but are not limited to, proteoglycans (such as perlecan, versican, syndecan, decorin, lumican, and biglycan), proteoglycan core proteins, glycosaminoglycans (such as hyaluronic acid, chondroitin-4 sulfate, chondroitin-6 sulfate, dermatan sulfate, heparin, heparin sulfate, and keratan sulfate), Type V collagen, fibronectin, or any molecule that competes with collagen for available water (such as polyethylene glycol). Such molecules can be added to a solution containing collagen monomers prior to or following the precipitation of collagen as described herein.

Methods of Strain Stabilization, Monomer Incorporation and Enzymatic Degradation of Collagen Some of the methods described herein are based, at least in part, on the discovery of a strain-dependent mechanism that can modulate collagen fibril susceptibility to enzymatic degradation. This mechanism can produce a physicochemical change at the matrix level that is bound to fibril strain. Based on this "strain-stabilization of collagen" mechanism, tensile strains can provide a robust signal, leading to a load-controlled differential degradation (catabolism) of collagen in extracellular matrix. Further, tensile strains on collagen fibrils can provide a signal, leading to the incorporation of collagen monomers into loaded fibrils (this is monomer incorporation). In some instances, the adaptive remodelling response of load-bearing ECM can be controlled by collagen and its complement enzymes (e.g., bacterial collagenase, MMPs, and cathepsins), which couple the control signal (i.e., mechanical load) to a physicochemical change in the collagen molecules or fibrils. In addition, this mechanism can relieve fibroblasts of the burden of "knowing" which fibrils to degrade during remodelling and which to reinforce. Based on this mechanism, load-stimulated fibroblasts can produce a load-adapted morphological change during, e.g., epigenetic connective tissue remodelling, repair, homeostasis and disease.

In some instances, collagen is precipitated as described herein, and the collagen organization is further refined by subjecting the initial collagenous construct to cross-linking, mechanical strain, and/or enzymes to cull unwanted (unstrained) fibrils (see, e.g., Ruberti et al., *Biochem. Biophys. Res. Commun.* 336:483-489 (2005)).

Figure 25A:
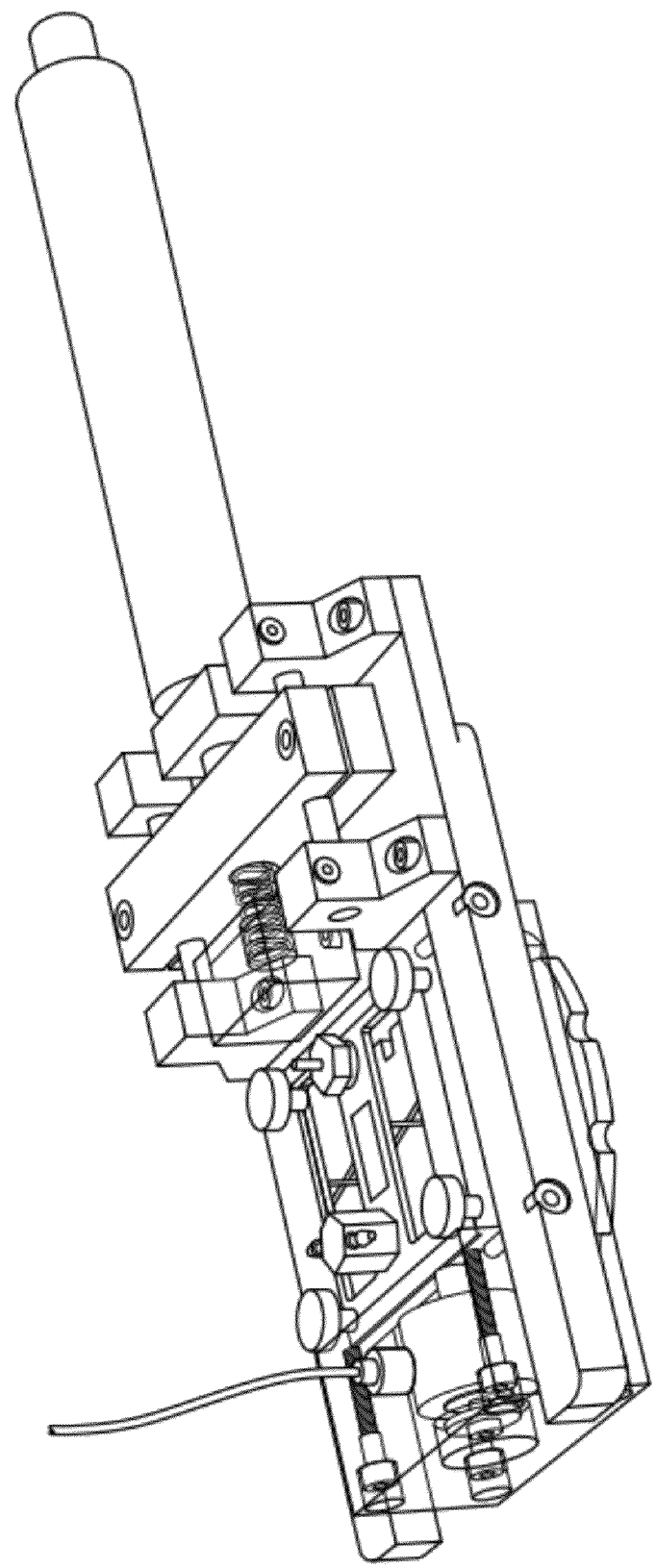
FIG. 25A is a representation of a Solidworks rendered image of a uniaxial loading system for growing construct strips under load.
Figure 25B:
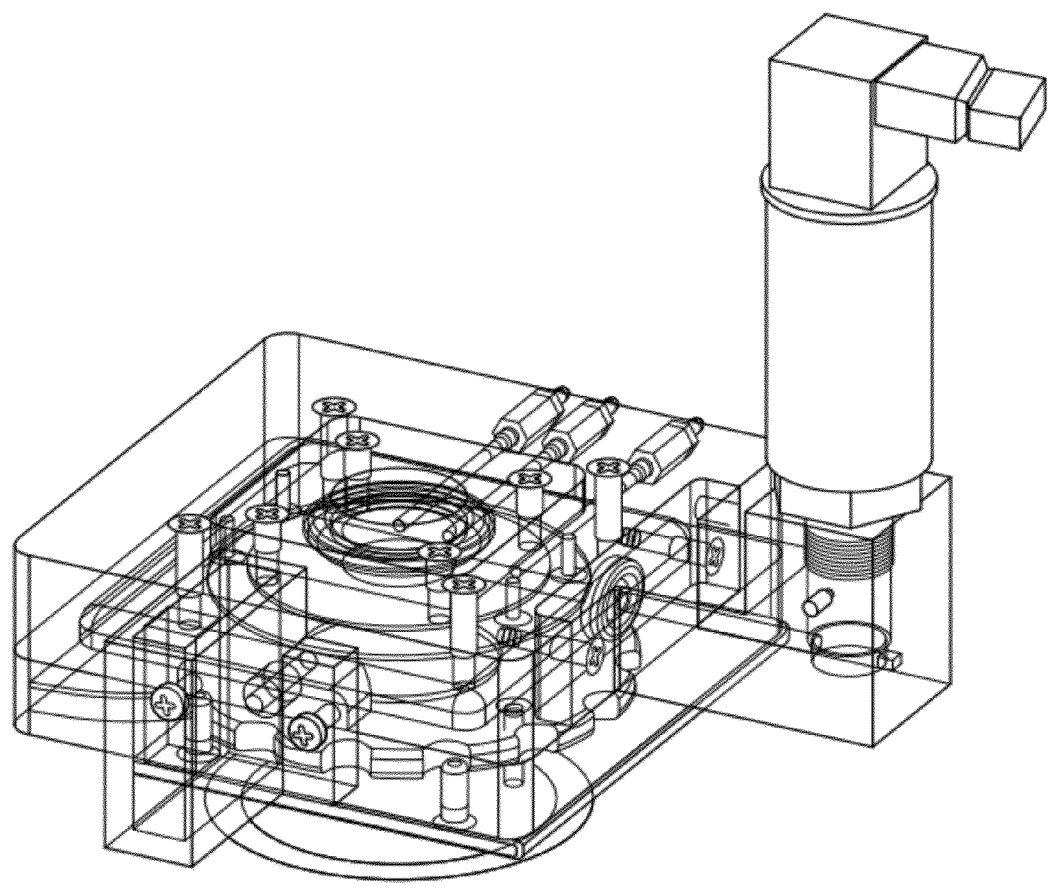
FIG. 25B is a representation of a Solidworks image of a tangential loading chamber for growing whole constructs under tangential load.

Mechanical strain can be applied to collagen fibrils using, e.g., a microchamber (see, e.g., FIG. 25). In such methods, the collagen can be fixed to grips in a microchamber by, e.g., direct clamping or by adhesives (such as cyanoacrylates). In some situations, the collagen is affixed to functionalized micropipettes as described herein. During the loading of mechanical strain, auxiliary molecules can optionally be included. In addition, hydroxyapatite and noncollagenous proteins can be added to calcify the system during loading.

In some situations, prior to the loading of the construct, collagen fibrils are cross-linked to facilitate strain production. Any suitable crosslinking agent known in the art can be used including, without limitation, formaldehyde, hexamethylene diisocyanate, glutaraldehyde, polyepoxy compounds, gamma irradiation, and ultraviolet irradiation with riboflavin. The crosslinking can be performed by any known method (see, e.g., Bailey et al., *Radiat. Res.* 22:606-621 (1964); Housley et al., *Biochem. Biophys. Res. Commun.* 67:824-830 (1975); Siegel, *Proc. Natl. Acad. Sci. U.S.A.* 71:4826-4830 (1974); Mechanic et al., *Biochem. Biophys. Res. Commun.* 45:644-653 (1971); Mechanic et al., *Biochem. Biophys. Res. Commun.* 41:1597-1604 (1970); and Shoshan et al., *Biochim. Biophys. Acta* 154:261-263 (1968)).

Enzymes

The methods described herein can be used to "sculpt" collagenous ECMs through application of mechanical load and also exposure to collagen-degrading enzymes including, without limitation, collagenase (e.g, bacterial collagenase), cathepsin, and matrix metalloproteases (MMPs). Thus, in some instances, collagen is contacted with a collagen-degrading enzyme and simultaneously subjected to mechanical load.

One non-limiting useful collagen degrading enzyme is bacterial collagenase (BC). BC attacks the triple helical domain of fibrillar collagen non-specifically at multiple sites. Another non-limiting useful collagen degrading enzyme is a matrix metalloprotease (MMP). In mammals, fibroblasts degrade matrix by expressing MMPs, which cleave collagen at a specific location three-quarters of the distance from the amino-terminus. MMP degradation of collagen proceeds by a ratchet mechanism, whereby the enzyme moves along collagen fibrils in steps, alternately binding to and cleaving the available monomers. MMPs cleave the collagen triple helix en bloc at a site that is at the interface of a loose, less rigid portion of the collagen triple helix (due to a lower hydroxyproline content) and a tighter portion of the triple helix. For cleavage to occur, the MMP catalytic domain also "unwinds" the collagen triple helix locally to gain access to a single alpha chain, while the hemopexin-like domain orients and destabilizes the collagen. While not wishing to be bound by theory, tensile mechanical loads may affect, e.g, reduce, the rate of MMP cleavage by one of the three following mechanisms: 1) reduction of configurational entropy of the binding site, which increases the energy to unwind and orient the collagen, 2) binding site distortion, which reduces the binding affinity, and 3) causing a relative shift in alpha chain registration, which makes cleaving difficult.

The cleavage rate of fibrillar collagen by MMPs or the rate of monomer incorporation into fibrils can be affected, e.g., reduced, by tensile mechanical loads. The load state of the matrix dictates which collagen fibrils are affected by the collagen degrading enzymes. As a corollary, newly secreted collagen intermediate filaments or monomers are preferentially incorporated into loaded fibrils and gain resistance to MMP degradation. Thus, these methods can be used to preserve only fibrils under strain, resulting in a matrix that is adapted to the applied load.

Methods of Engineering Tissues

Collagen produced by the methods described herein can be used to engineer tissues or organs including, but not limited to, bone, dental structures, joints, cartilage, skeletal muscle, smooth muscle, cardiac muscle, tendons, menisci, ligaments, blood vessels, stents, heart valves, corneas, ear drums, nerve guides, tissue or organ patches or sealants, a filler for missing tissues, sheets for cosmetic repairs, skin (sheets with cells added to make a skin equivalent), soft tissue structures of the throat (such as trachea, epiglottis, and vocal cords), other cartilaginous structures (such as articular cartilage, nasal cartilage, tarsal plates, tracheal rings, thyroid cartilage, and arytenoid cartilage), connective tissue, vascular grafts and components thereof, and sheets for topical applications or for repair or replacement of organs (such as livers, kidneys, and pancreas).

In some situations, the collagen is produced having a predetermined shape, such as a predetermined shape dictated by external and internal templates described herein. In specific instances, the templates can be shaped, for example, in the shape of a nerve guide, skin or muscle patch, fascial sheath, vertebral disc, knee meniscus, ligament, tendon, or a vascular graft for subsequent use in vivo. The collagen can also be shaped to fit a defect or site to be filled, e.g., a site where a tumor has been removed or an injury site in the skin (e.g., a cut, a biopsy site, a hole or other defect) or to reconstruct or replace a missing or shattered piece of bone. The methods described herein allow for great flexibility and the ability to customize the collagen to virtually any shape needed. Specific geometries include, but are not limited to, a cylindrical shape, a flattened oval shape, capillary tubes (as in tendon), concentric cylinders (as in artery, annulus fibrosus, lamellar bone) and nested hemispheres (as in cornea).

In some instances, further shaping can be achieved by manually processing the formed collagen. For example, formed collagen can be sutured, sealed, stapled, or otherwise attached to one another to form a desired shape The invention is further illustrated by the following examples. The examples are provided for illustrative purposes only. They are not to be construed as limiting the scope or content of the invention in any way.

EXAMPLES

Example 1

In Vitro Production of Organized Collagen Lamellae using a Scaffold-Free Model of Corneal Stromal Development An in vitro model of corneal stromal development was developed as follows. Briefly, primary human corneal fibroblasts by migration from corneal explants in culture) were grown to confluence on a transwell membrane and stimulated to produce matrix with a stable form of ascorbic acid (Guo et al., *Invest. Ophthalmol. Vis. Sci.* (2007), 48(9):4050-4060). This scaffold-free approach allowed the fibroblasts to self-organize and then stratify, and is the first culture system capable of producing significant quantities of organized lamellae that are morphologically similar to in vivo lamellae in that they alternate in direction. It also shares some features of developing systems, including cell organization and a relatively high ratio of cell volume to matrix volume (at least initially).

Figure 1B:
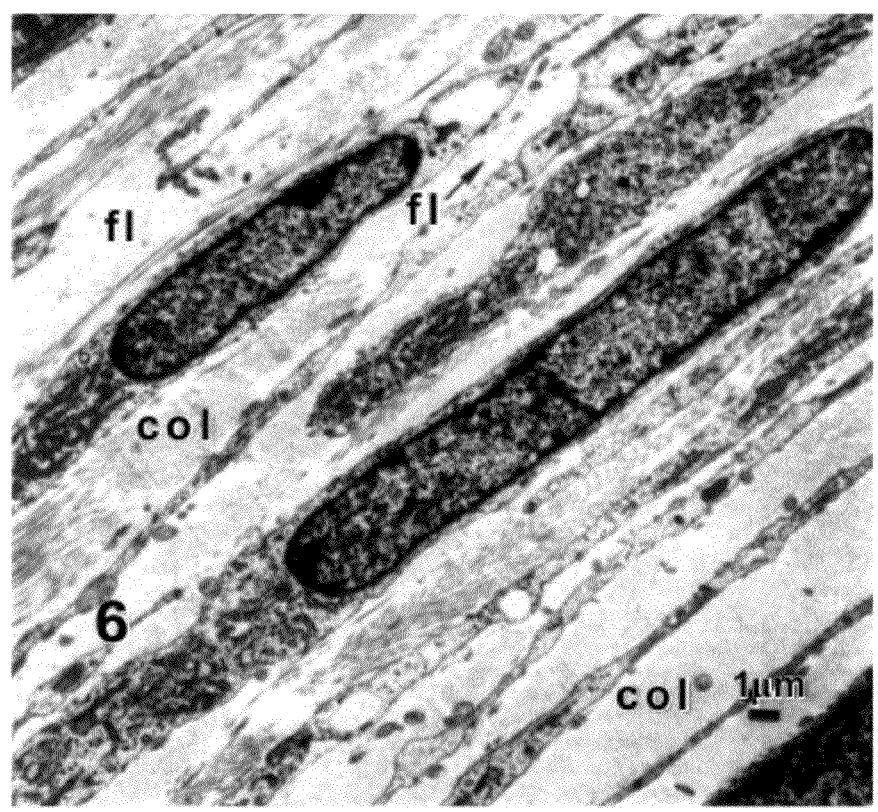
FIG. 1B is a representation of a TEM micrograph of organized, alternating collagen lamellae deposited by human primary corneal fibroblasts during the development of a non-human primate (macaque) cornea in vivo at 60 days. Fibril direction changes in the human culture system are indicated by the black arrows; Col=collagen; fl=flocculent material.

The data obtained demonstrate that highly-organized collagen was synthesized between two confluent monolayers of fibroblast cells. The monolayers appeared to separate from one another, as organized matrix was secreted between them. FIGS. 1A-1B compare in vivo development of collagen organization in the primary human fibroblast culture to that of a developing primate. Both images demonstrated flattened fibroblasts (dedifferentiated human fibroblasts for the in vitro study and mesenchymal fibroblasts for the in vivo development study) and collagen fibrils that alternated in direction in subsequently deposited lamellae. The thickness of the lamellar collagen arrays was about 1μ-2μ in both systems (which may be an intrinsic length scale for collagen rotation).

The fibroblasts produced 25μ of aligned collagen lamellae (each about 2 μm) within a thicker construct (36 μm) by four weeks as measured by differential interference contrast microscopy (DIC). The model was extended to 12 weeks and reached steady state by 8 weeks (50 μm thick with 25 μm of organized matrix), but appeared to begin to lose collagen fibrils by 12 weeks.

The organized collagenous lamellae were confined between the bounding cell layers, which may show that confinement is important. Further, the lamellae were approximately 2 μm thick before changing direction, which may show the existence of an intrinsic organizational length scale.

Example 2

De Novo Production of Sheets of Organized Collagen by Concentration and Confinement To generate local, long-range and three dimensional fibril organization, a method was developed using the organizational information encoded into the collagen triple helix. Using this method, confined, patterned arrays of monomers condensed into organized arrays of fibrils upon enzymatic cleavage of collagen propeptides.

Methods

Preparation of Collagenous Constructs—Method I.

3 mg/ml solution of collagen (Inamed biomaterials, Fremont, Calif.) was dialyzed against 40% solution of polyethylene glycol (PEG) (20 kMWCO, Sigma) at 4° C. to reach the concentrations in the range of 140 mg/ml-200 mg/ml (medium concentration). The collagen solution was neutralized (pH 4.5-7) with 1.5 M Trizma based solution (Sigma-Aldrich, St. Louis, Mo.), confined between two coverslips, transferred into a 37° C. incubator, and stored for 6 hrs prior to assessment.

Preparation of Collagenous Constructs—Method II.

A medium concentration solution of collagen (prepared as described above) was transferred into a 3.5 kMWCO dialysis cassette (Thermo Scientific, Rockford, Ill.) and left in 40% solution of PEG overnight at 4° C. to reach concentrations in the range of 200 mg/ml-400 mg/ml. To neutralize the collagen solution, the cassettes were transferred into a neutralized PEG solution (using Trizma base) and stored up to 2 wks prior to assessment.

Primary Human Corneal Stromal Cell-Derived Constructs.

Cell-derived constructs were produced as described in Guo et al. (*Invest. Ophthalmol. Vis. Sci.* 48:4050-4060 (2007)) on disorganized collagenous mats (Ren, et al. *Dev. Dyn.* 237: 2705-2715 (2008)).

Transmission Electron Microscopy (TEM).

Constructs were fixed overnight in Karnovsky fixative (2.5% glutaraldehyde, 2.5% formaldehyde, 0.1 M cacodylate buffer), washed with 0.1 M buffer, post-fixed in 2% osmium tetroxide, and dehydrated in degraded ethanol. The samples were infiltrated and embedded in modified spun resin (as described in Ellis, Microscopy Today 14:32 (2006)). 60 nm cross sectional and en face sections were cut using a diamond knife ultramicrotome (Ultra Cut E Microtome; Reichert, Depew, N.Y.) and stained with 5% uranyl acetate and Reynolds lead citrate. The sections were viewed and photographed with a transmission electron microscope (JEM 1010; JEOL, Tokyo, Japan).

Scanning Electron Microscopy (SEM).

SEM analysis was conducted as described in Example 3.

Differential Interference Contrast (DIC) Microscopy.

The long range organization of the collagen fibrils was investigated using DIC (Guo et al., *Invest. Ophthalmol. Vis. Sci.* 48:4050-4060 (2007)). The collagenous constructs were transferred between two coverslips and placed on the stage of an inverted microscope (TE2000U; Nikon). The alignment of collagen fibrils was studied using series of in-plane and Z-stacks.

Results

As shown in FIG. 2, primary human corneal fibroblasts naturally formed confluent and generally orthogonal sheets on two-dimensional surfaces. The following experiment was conducted to determine whether confinement and concentration of monomers leads to the production of organized arrays of collagen fibrils, the following. Triple helical domains of Type I collagen (atelo-collagen monomers extracted from bovine dermis (PURECOL®)) were concentrated to liquid crystalline levels at the following two different concentrations. Low concentration (LC) was 140 mg/ml-200 mg/ml and high concentration (HC) was 280 mg/ml-400 mg/ml. The collagen monomers in the resulting viscous solutions were then "precipitated" to form fibrillar structures while confined between two surfaces.

Figure 2A:
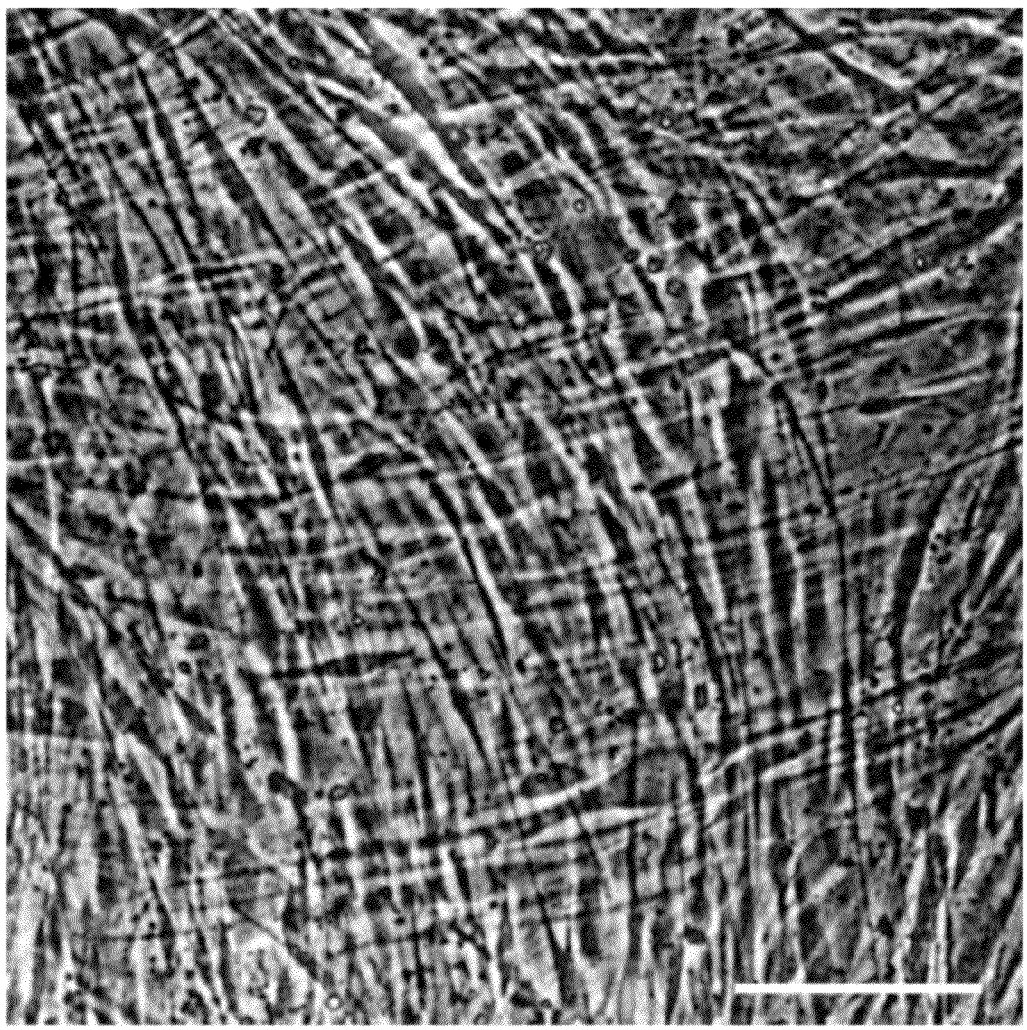
FIG. 2A is a representation of a phase contrast image of 2 week old in vitro primary human corneal stromal cell (PHCSC)-derived collagen constructs, where bar is 50μ.
Figure 2B:
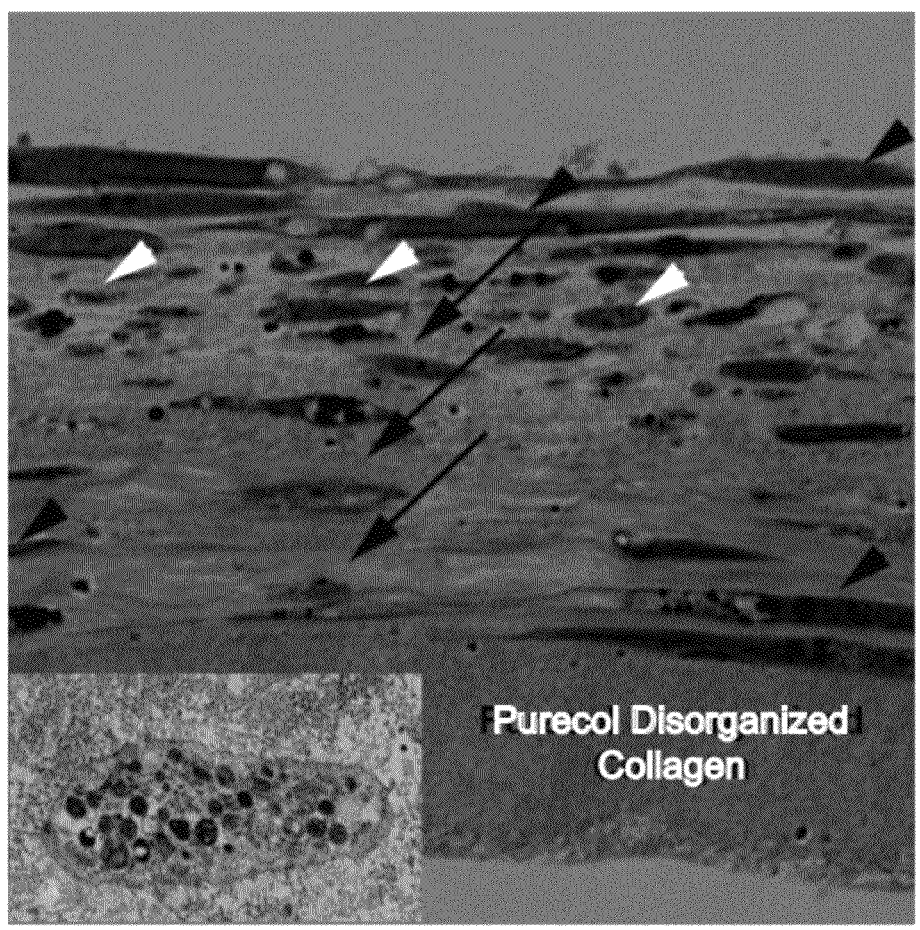
FIG. 2B is a representation of an optical thick section of 8 week old PHCSC-derived, stratified collagen construct comprising PHCSCs with "orthogonal" orientation changes (white and black arrowheads) and layers where aligned collagen lamellae are typically observed (black arrows), and the inset depicts an sTEM of single PHCSC in cross-section surrounded by collagen fibrils aligned with cell long axis. This demonstrates internal templating by the resident cells.
Figure 2C:
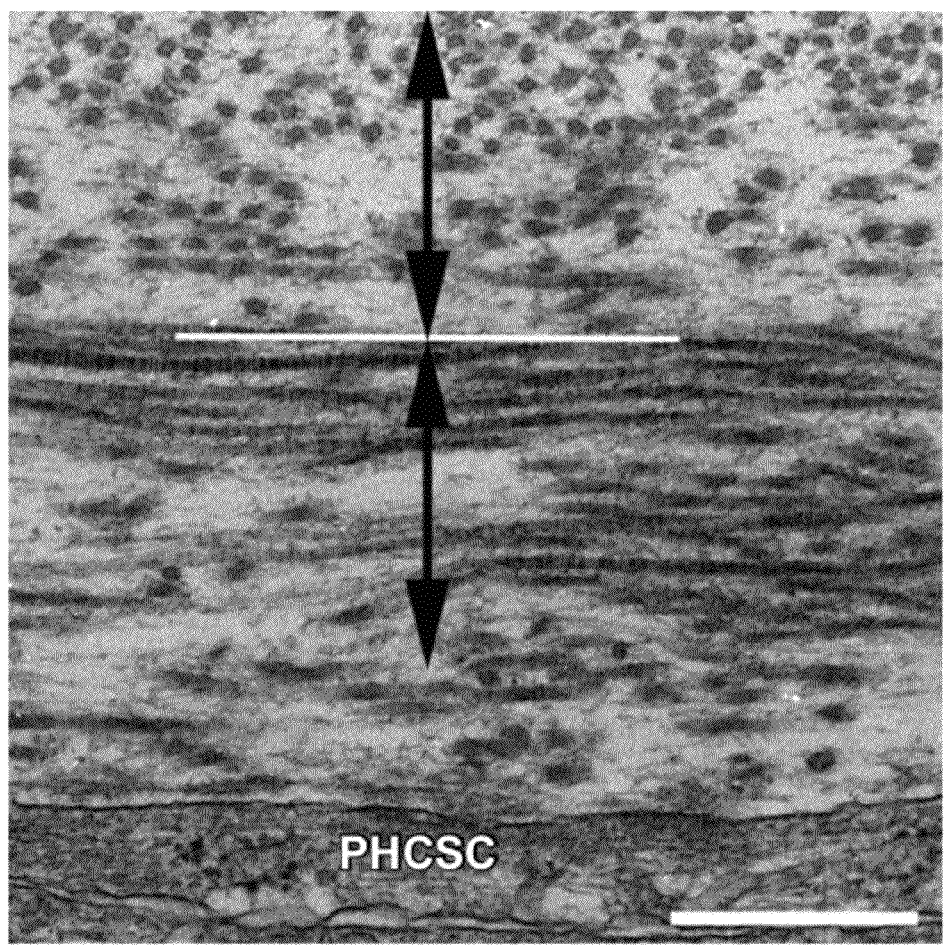
FIG. 2C is a representation of an sTEM of cell-synthesized collagenous matrix comprising alternating layers of small diameter collagen fibrils, where bar is 500 nm.
Figure 2D:
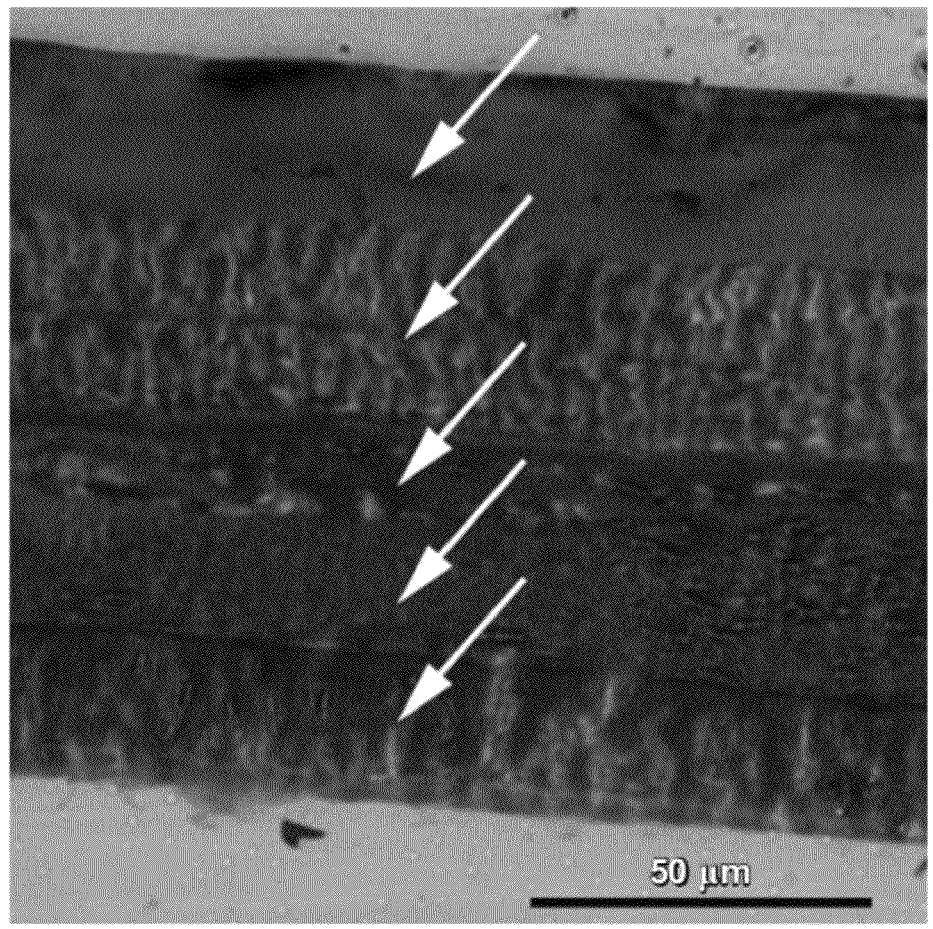
FIG. 2D is a representation of an optical thick section of a low concentration (LC) liquid-crystal-collagen-derived de novo construct, where five morphologically distinct layers (at low magnification light microscopy) are clearly visible in this 100 micron thick cross-section (white arrows indicate individual layers).

FIG. 2D shows the cross-section of the lamellar-like stratification of a typical LC de novo construct produced by confinement and concentration of monomer followed by fibillogenesis.

Figure 3B:
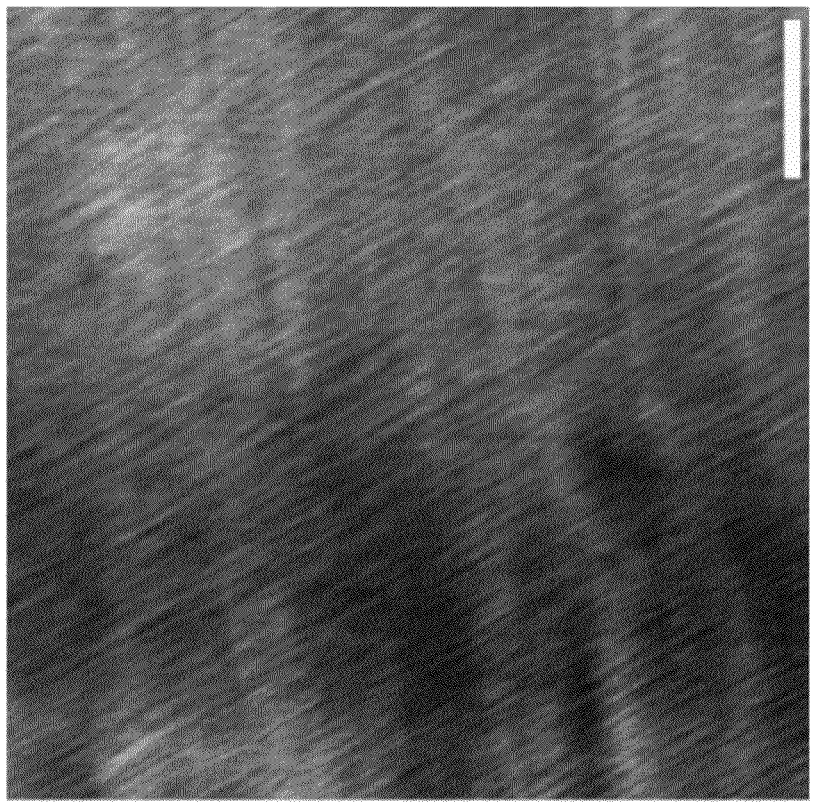
FIG. 3B is a representation of a DIC optical micrograph of de novo collagen constructs from high concentration of collagen monomers.
Figure 3A:
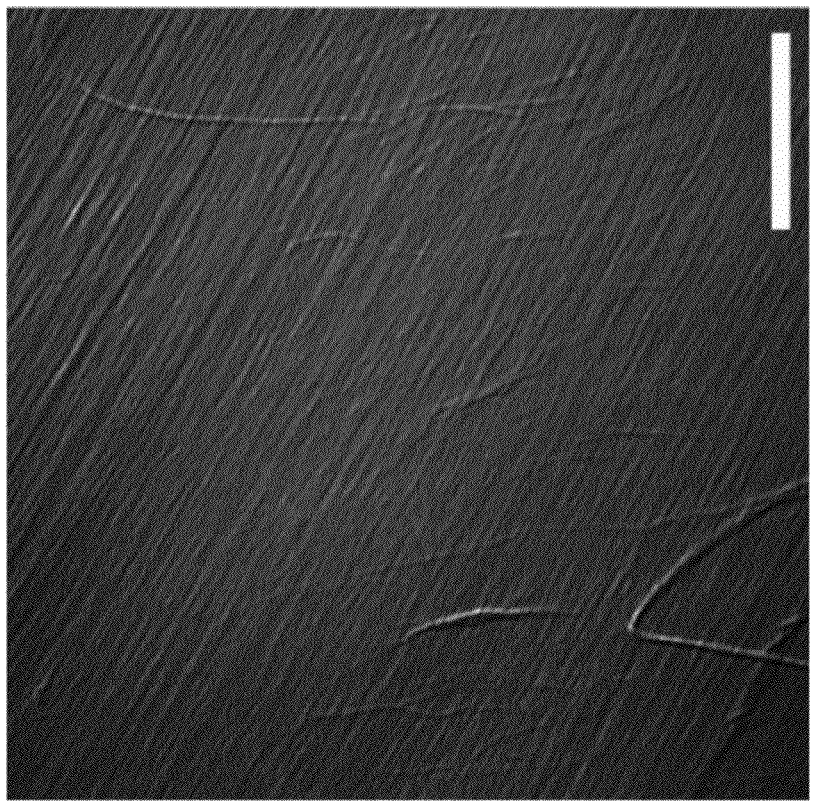
FIG. 3A is a representation of a DIC optical micrograph of de novo collagen constructs from low concentration of collagen monomers.
Figure 3D:
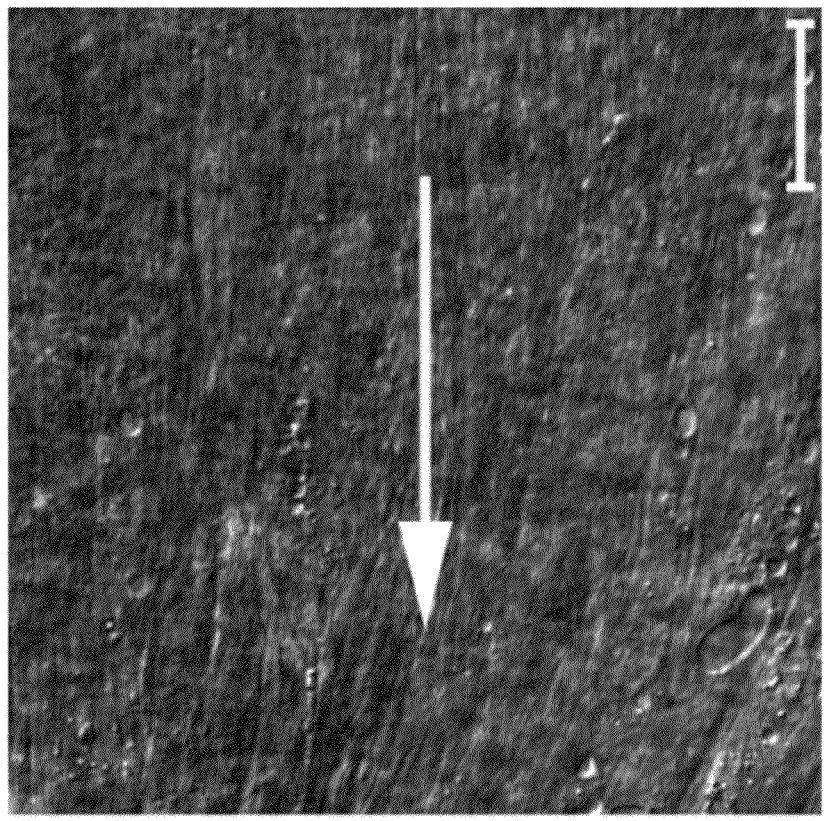
FIG. 3D is a representation of a DIC optical micrograph extracted from z-scans of PHCSC-derived collagenous matrix alignment. The matrix alignment angle changes 90° over a depth of 7μ. The bar is 20μ.
Figure 3C:
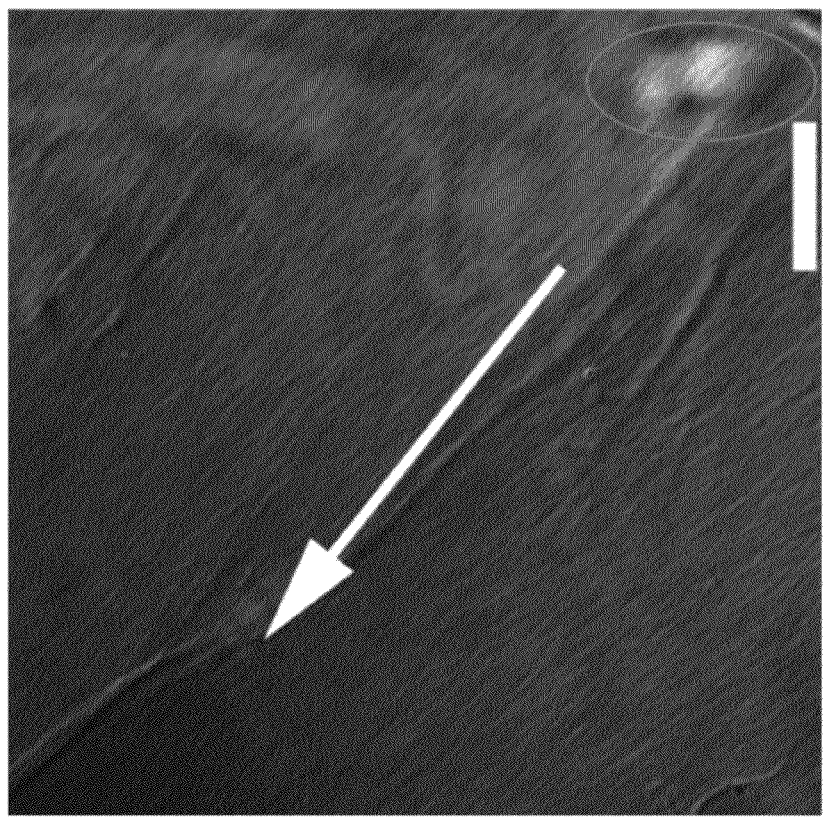
FIG. 3C is a representation of a DIC optical micrograph extracted from z-scans of de novo collagen constructs from low concentration of collagen monomers. The matrix alignment angle changes 30° over a depth of 30μ. The bar is 20μ.
Figure 3F:
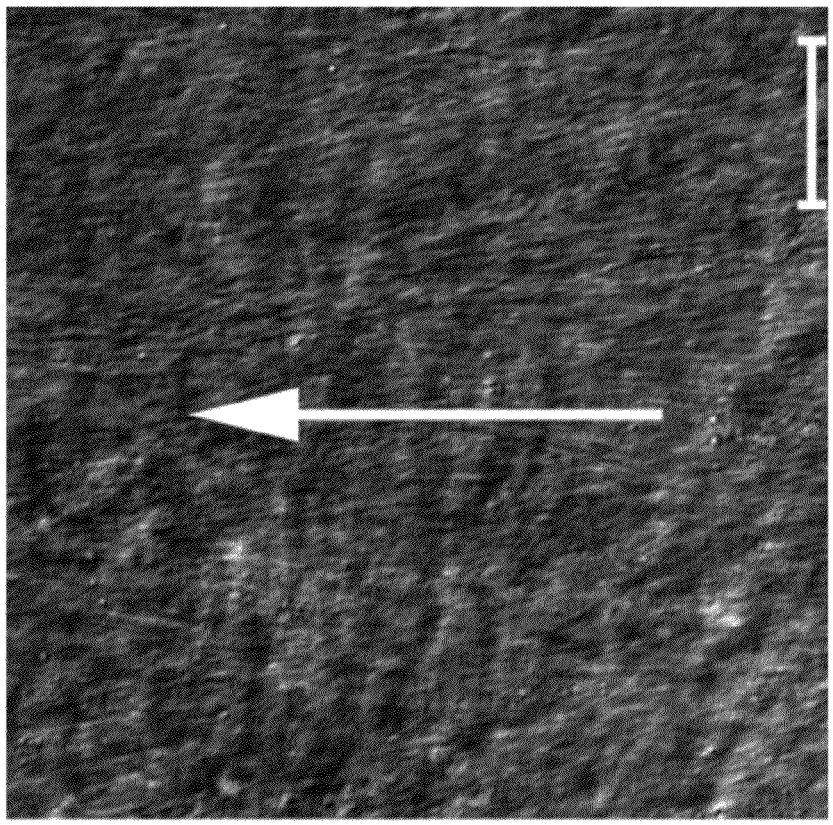
FIG. 3F is a representation of a DIC optical micrograph extracted from z-scans of PHCSC-derived collagenous matrix alignment. The matrix alignment angle changes 90° over a depth of 7μ. The bar is 20μ.
Figure 3E:
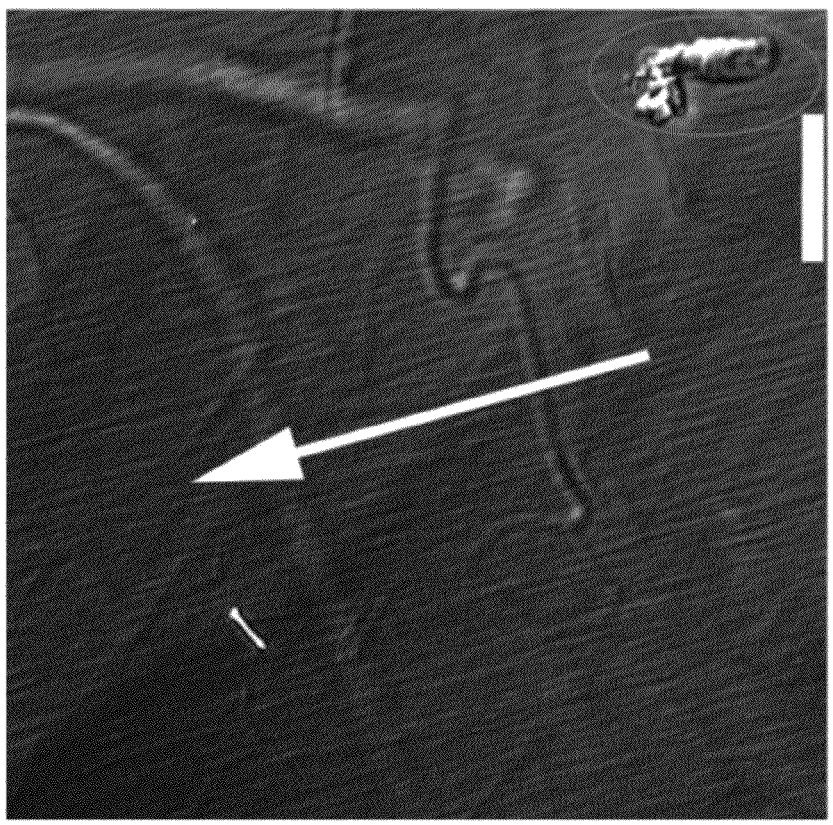
FIG. 3E is a representation of a DIC optical micrograph extracted from z-scans of de novo collagen constructs from low concentration of collagen monomers. The matrix alignment angle changes 30° over a depth of 30μ. The bar is 20μ.

Differential interference contrast (DIC) z-scan optical imaging was in agreement with the thick section data and revealed that the de novo constructs possessed multiple "lamellae" within which the fibrillar matrix was uniformly aligned over long distances in the x-y plane on the order of hundreds of microns (FIG. 3A). For the LC experiments, the spontaneously formed lamellae were 16.6μ±6.3μ thick and their constituent fibrils changed direction en mass at an average angle of 50±24 degrees.

DIC images of the LC constructs were qualitatively compared with constructs produced by fibroblasts in vitro. In general, the lamellar organization in the LC de novo constructs compared favorably with the matrix alignment found in PHCSC-derived stromal constructs (FIG. 3). In PHCSC-derived constructs, synthesized lamellae are generally 2μ-5μ thick and appear to change direction by 90°. This was observed when direction changes were clearly observable by DIC (see FIGS. 3D and 3F). In the normal human cornea, collagen lamellae are approximately 2μ thick, and the angle between successive lamellae is also generally 90° (as described in Meek et al., *Exp. Eye Res.* 78:503-512 (2004)). Thus, the LC de novo constructs synthesized comprised thicker aligned lamellar structures that changed direction more arbitrarily than native tissue.

Figure 4B:
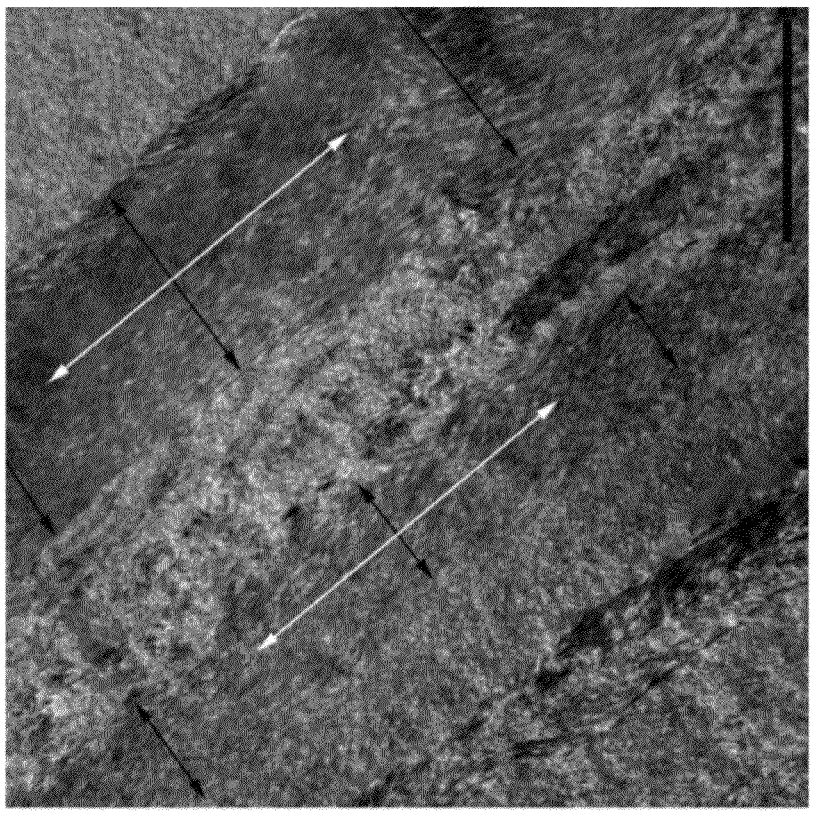
FIG. 4B is a representation of a cross-section low magnification sTEM micrograph of lamellar structures spontaneously formed in de novo construct at low concentration of collagen. Black arrows indicate the width of a lamella, and white arrow indicates the direction of fibril alignment in a lamellar plate, where bar is 2μ.
Figure 4A:
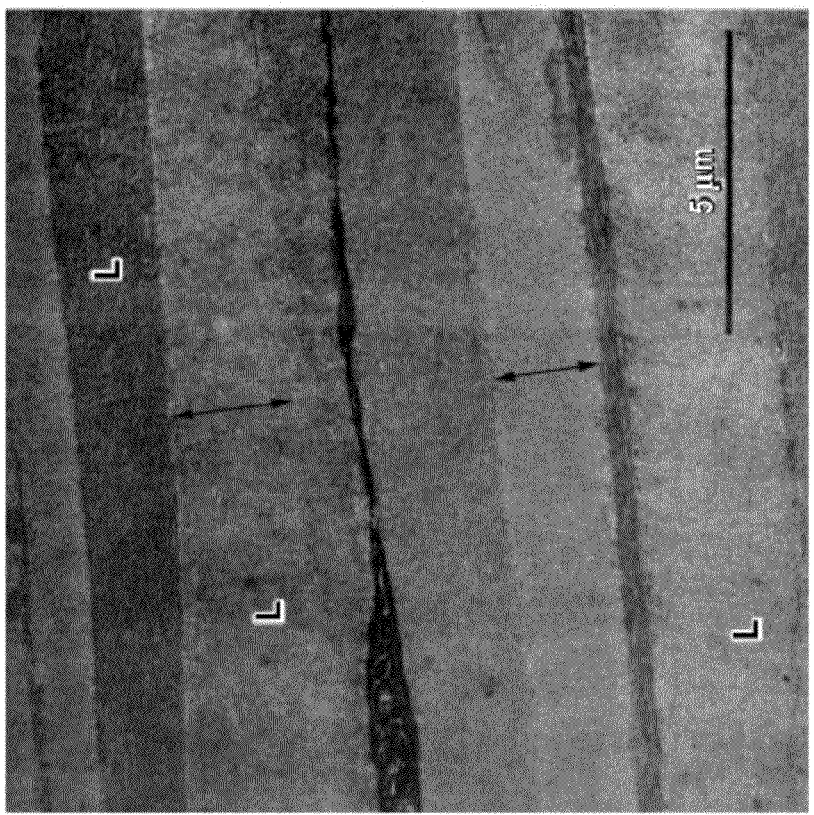
FIG. 4A is a representation of a cross-section low magnification sTEM micrograph of human corneal lamellae.
Figure 4D:
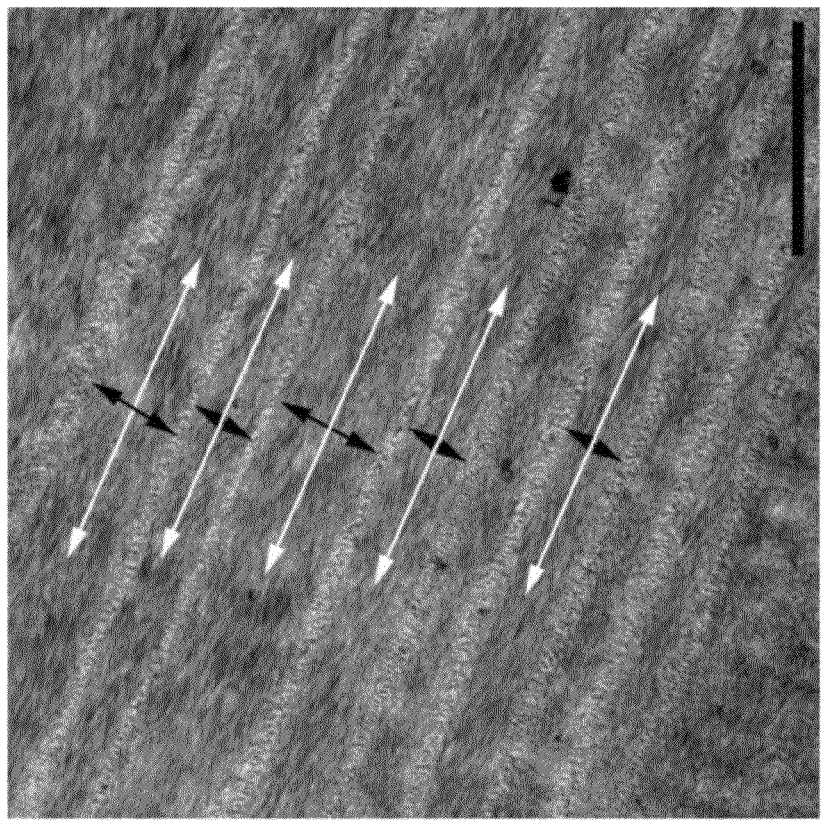
FIG. 4D is a representation of a cross-section low magnification sTEM micrograph of lamellar structures formed in de novo constructs at high collagen concentration, where bar is 2μ.
Figure 4C:
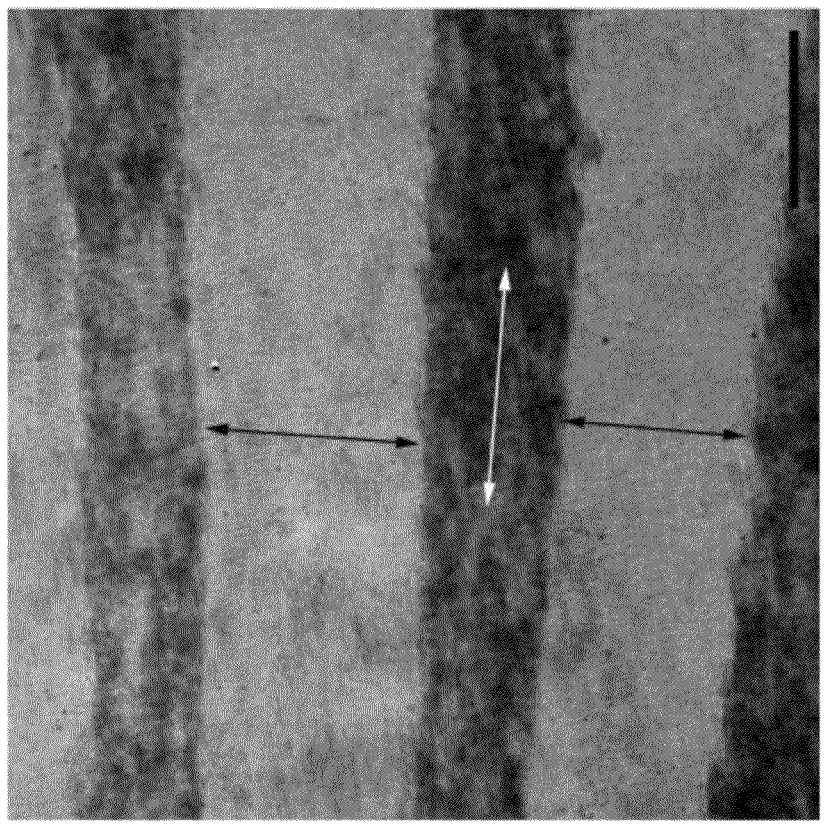
FIG. 4C is a representation of a cross-section low magnification sTEM micrograph of lamellar structures formed in de novo constructs at high collagen concentration, where bar is 5μ.
Figure 6C:
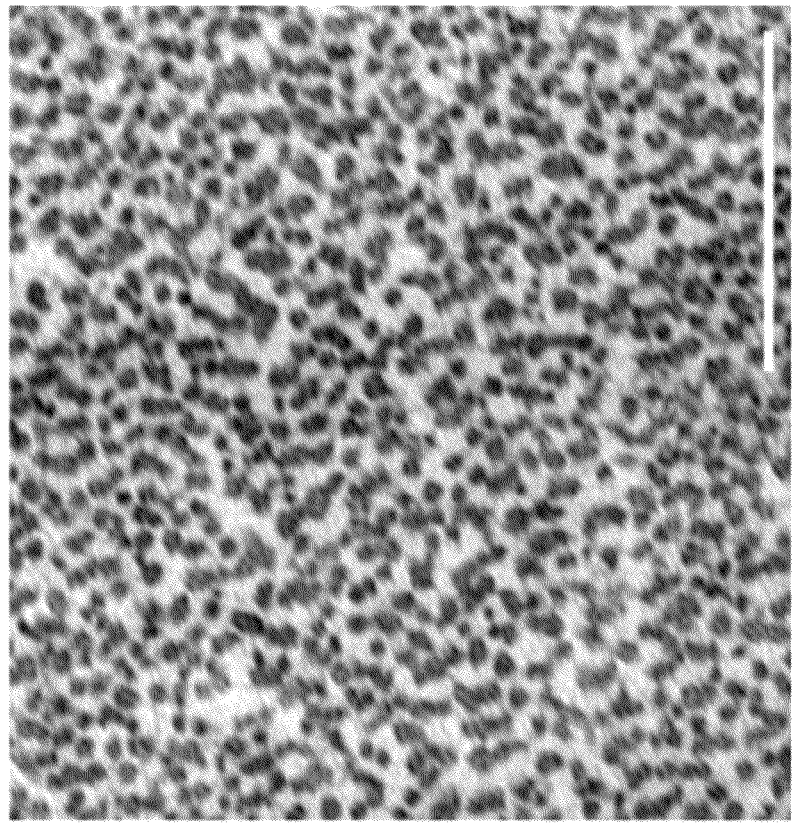
FIG. 6C is a representation of a high magnification sTEM micrograph of collagen in cross-section showing the presence of individual fibrils, where bar is 500 nm.

Standard transmission (sTEM) and scanning (SEM) electron microscopy of the de novo constructs in cross-section corroborated the results of the DIC imaging by revealing alternating arrays of aligned fibrils in ersatz "lamellae". Low magnification sTEMs of the constructs produced from LC (FIG. 4B) and HC (FIG. 4C) collagen bore a striking resemblance to sTEMs of the normal human cornea (FIG. 4A) (see, Komai et al., *Invest. Ophthalmol. Vis. Sci.* 24:543-556 (1983)). Cross-sectional SEM also confirmed the high fibril density, high-degree of fibril alignment and lamellar structure in constructs produced from HC collagen (FIG. 6A). The sTEMs also showed that the spontaneously formed lamellae varied in thickness (FIG. 4D).

Taken together, the low magnification sTEM, SEM and DIC confirm that dense, aligned fibrillar structures spontaneously precipitated from confined, concentrated monomers. Confined collagen appears to be cooperative in that lamellae appeared to be spontaneously formed parallel to the confining surfaces.

Figure 5A:
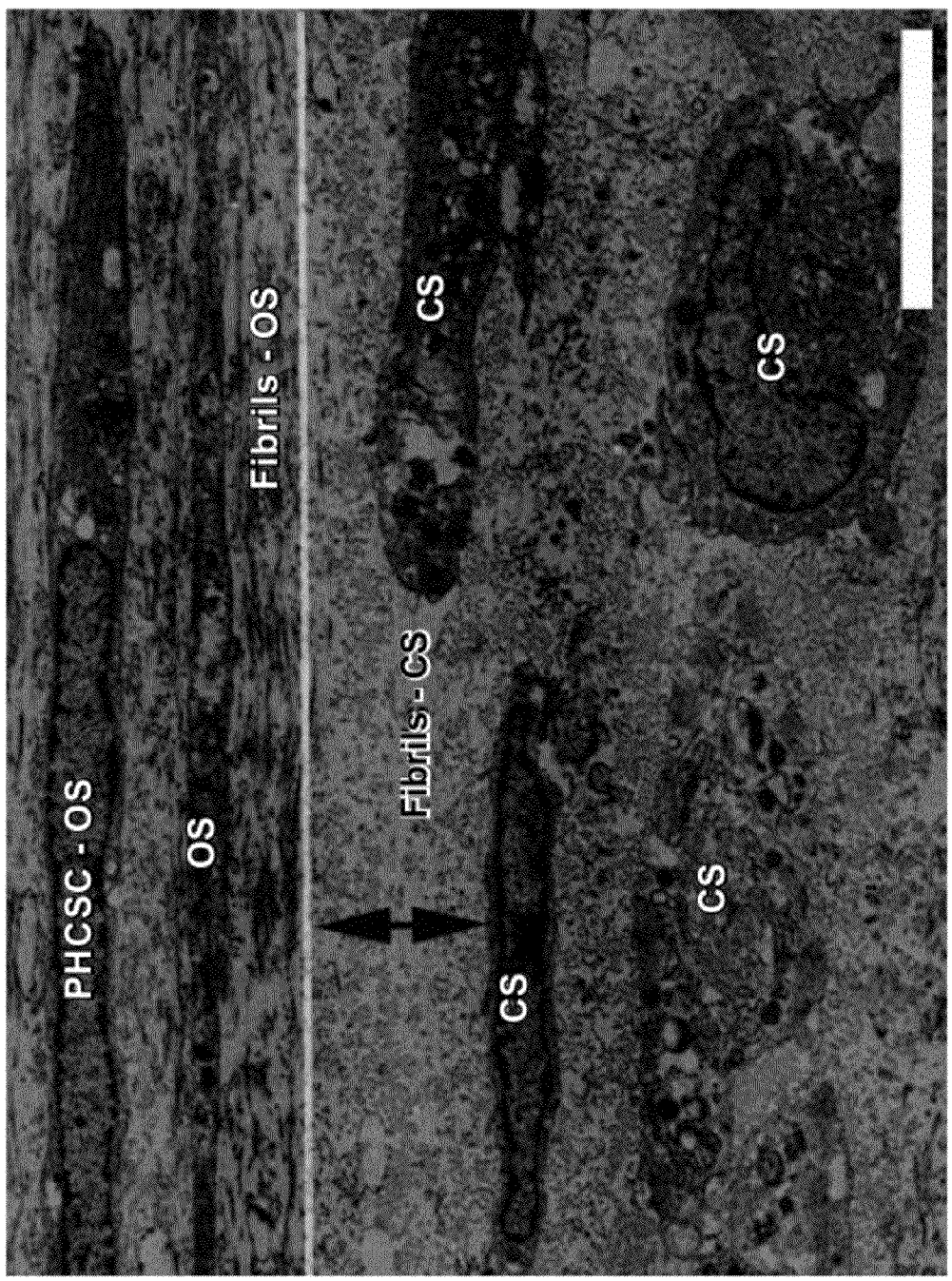
FIG. 5A is a representation of a sTEM micrograph of PHCSC cells in a 4 week old construct co-aligned with collagen fibrils, where collagen fibrillar arrays change direction at the white line; below the white line, collagen fibrils and cells are in cross-section (CS); and above the line cells and fibrils are in oblique section (OS), where black double arrow indicates the distance over which cell orientation could be influencing the fibril orientation, and bar is 4μ.
Figure 5B:
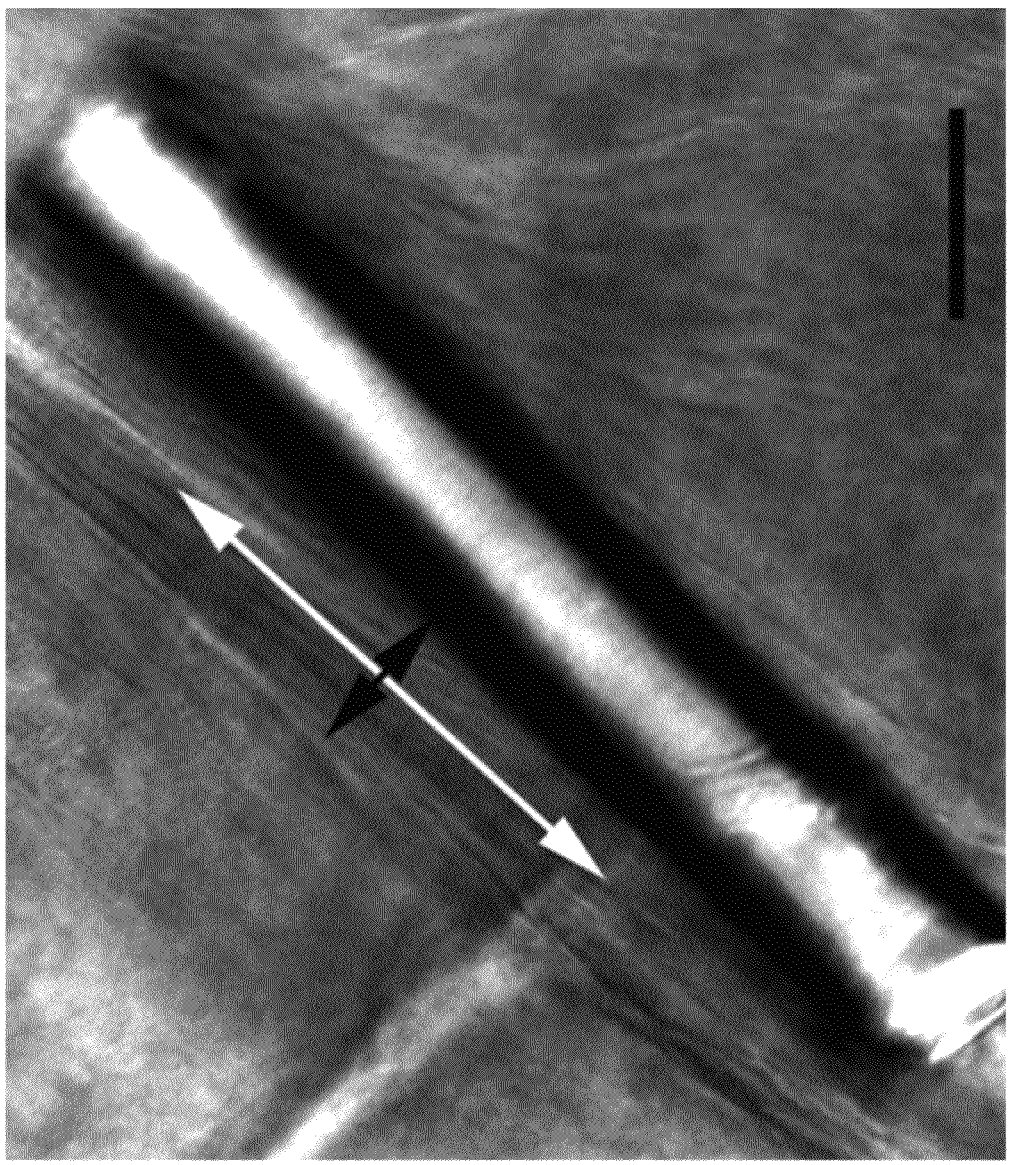
FIG. 5B is a representation of a DIC micrograph of a glass microcylinder embedded in fibrils precipitated from liquid crystalline collagen monomers, where black double arrow indicates the distance over which the glass "guides" collagen; white double arrow indicates direction of fibrils, and bar is 20μ.

Fibroblasts may play a role in providing additional "guidance cues" to direct the forming collagen lamellae. Fibroblasts in the bounding confluent layers may provide external guidance cues (e.g, elongated cell shape) while embedded fibroblasts may control local directionality of the monomers via internal guidance cues (e.g, elongated cell shape and filipodial extensions). In PHCSC derived constructs, collagen fibrils were often seen in co-alignment with the long axis of the fibroblast body. FIG. 5A shows two adjacent lamellae produced by PHCSCs where direction of the fibrils and of the embedded cells (which are co-aligned) changes abruptly. FIG. 5B demonstrates that the direction of collagen fibrils can be locally modified by the presence of a high-aspect-ratio object (such as a glass microcylinder). Thus, the combination of geometric confinement and internal guidance cues (spaced appropriately) may be used to fully control the orientation of collagen fibrils precipitated from dense solutions of collagen monomers.

Figure 6B:
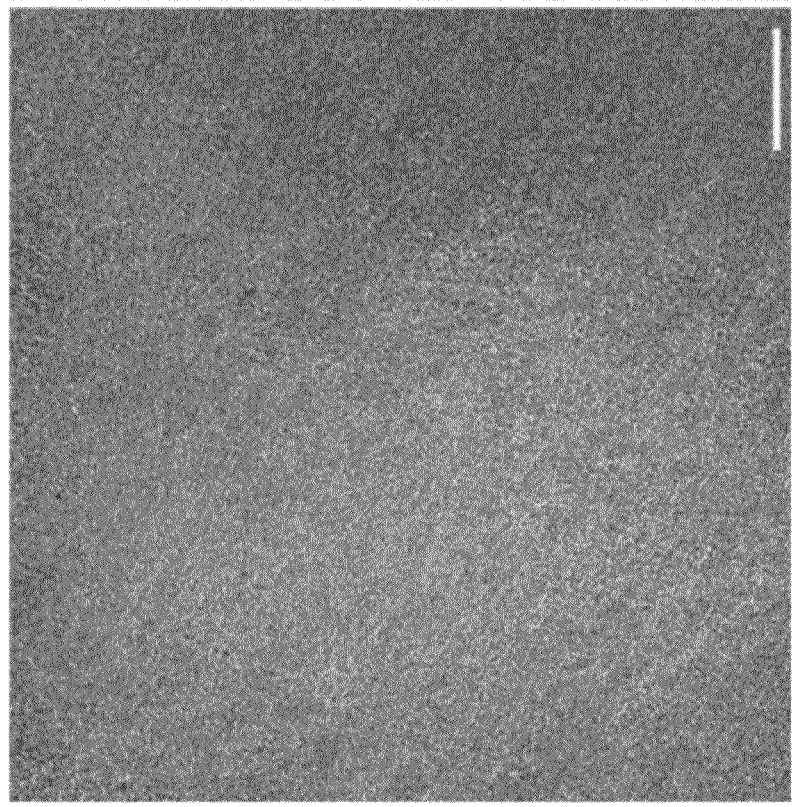
FIG. 6B is a representation of a low magnification sTEM micrograph of a large uniform area in cross-section showing the high-density and uniformity of the fibrillar array, where bar is 2μ.

The cross-sectional morphology of precipitated fibrils was also examined. FIGS. 6A and 6B are low magnification and high magnification sTEMs of an array of collagen fibrils in cross-section that were precipitated from HC collagen monomer solutions. The higher magnification image of the de novo construct fibrils revealed generally small diameter, highly polydisperse and irregular "fused" fibrils. Auxiliary ECM molecules such as proteoglycans, glycosaminoglycans or other collagens may aid in the formation of uniform diameter or circular fibrils.

Figure 7B:
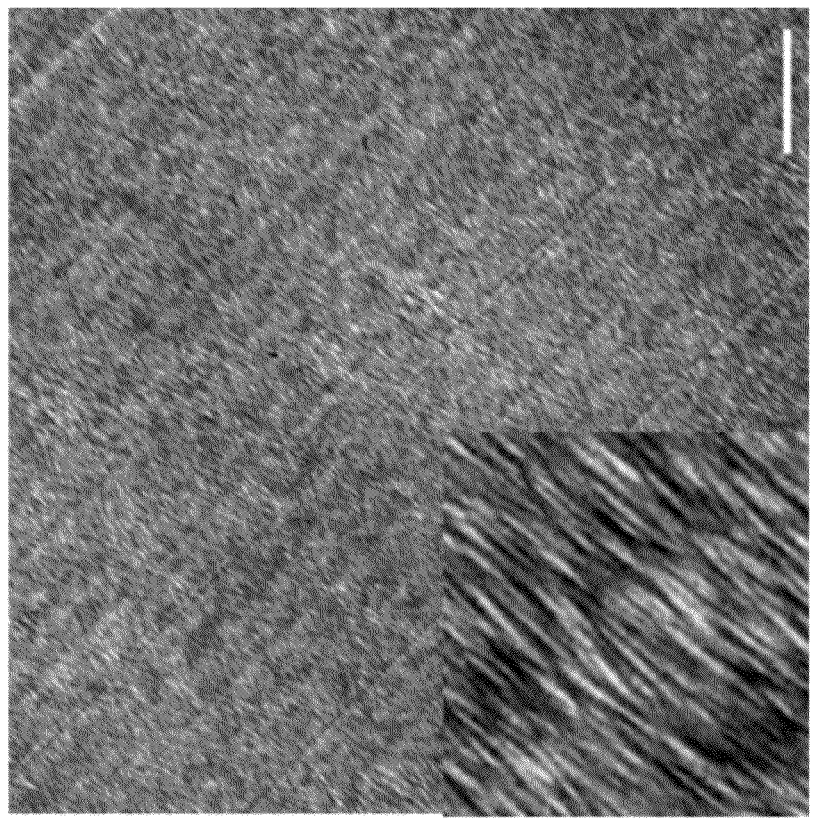
FIG. 7B is a representation of a sTEM micrograph of collagen from high concentration collagen monomers, where inset is a higher magnification, and bar is 100 nm.
Figure 7A:
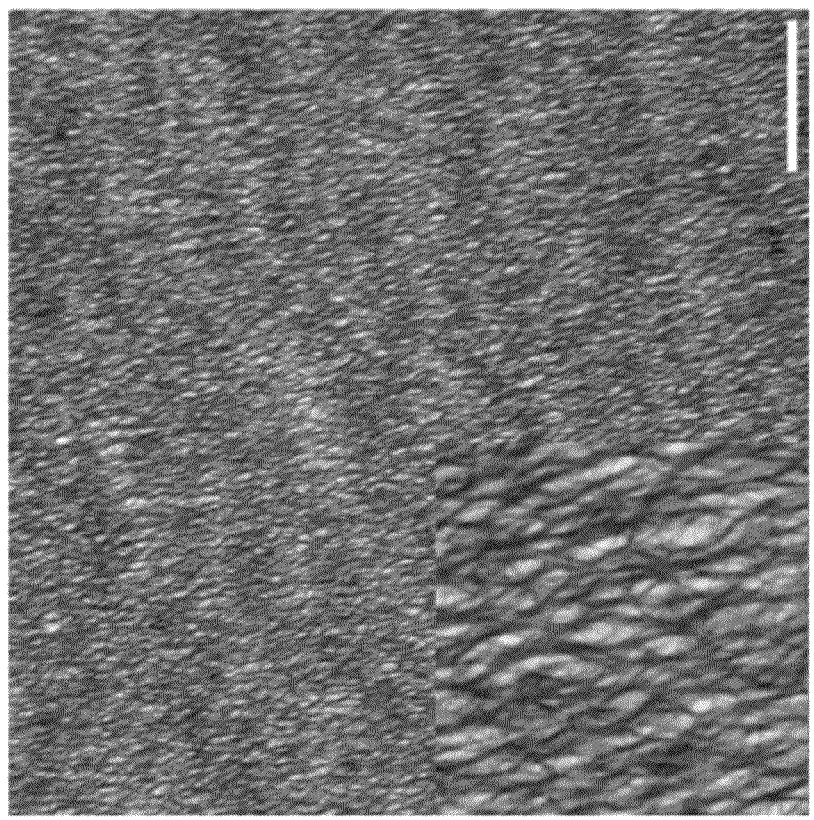
FIG. 7A is a representation of a sTEM micrograph of collagen from low concentration collagen monomers, where inset is a higher magnification, and bar is 100 nm.
Figure 7D:
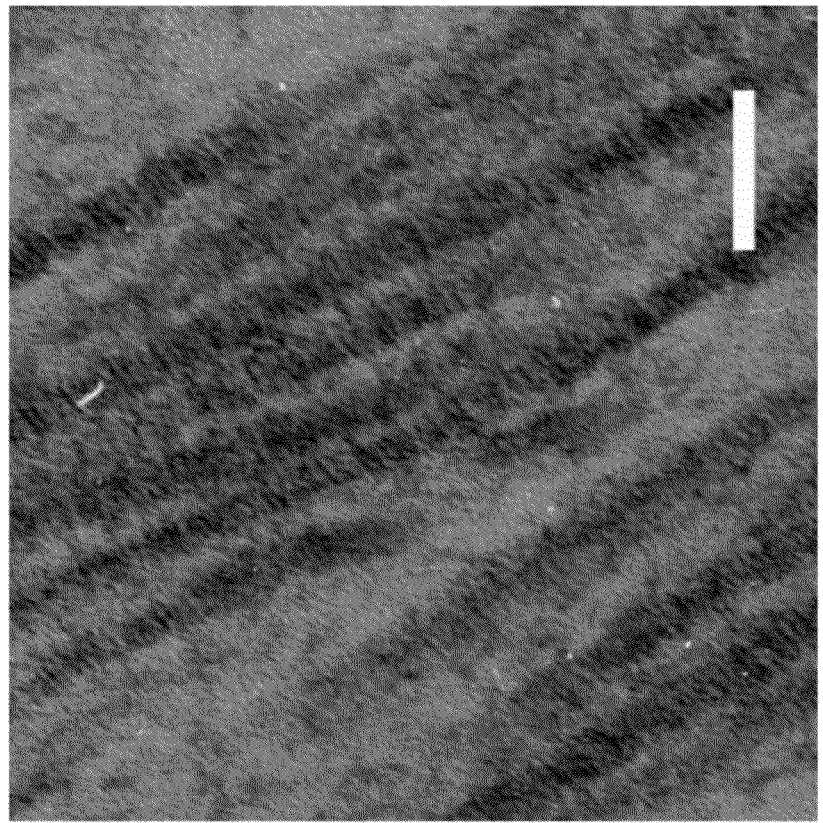
FIG. 7D is a representation of a sTEM micrograph of PHCSC-derived collagen, where bar is 100 nm.
Figure 7C:
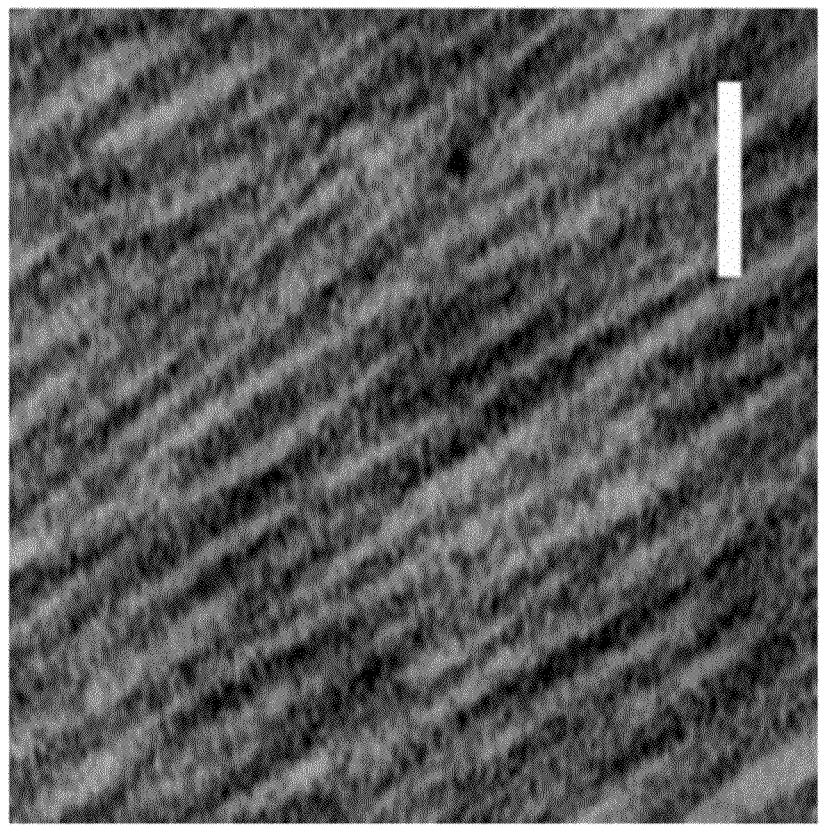
FIG. 7C is a representation of a sTEM micrograph of collagen from high concentration collagen monomers, and bar is 100 nm.

In the plane of the de novo constructs, TEM generally confirmed the DIC images. Large areas of complete fibril alignment parallel to the confining surfaces were seen (FIGS. 7A and 7B). In LC constructs, fibrils sometimes adopted a "wavy pattern", suggesting the production of open space as monomers were incorporated into the aggregating fibrils (FIG. 7A). In HC constructs, the collagen was generally more tightly packed and highly-aligned parallel to the confining surface (FIG. 7B). At high magnification, collagen fibrils in longitudinal section were thin (about 20μ), tightly packed and highly aligned (FIG. 7C). Direct comparison to PHCSC-synthesized collagen (FIG. 7D) demonstrated that the fibrils in the de novo construct were smaller and did not have clear D-periodic banding (though some striations were seen).

These results demonstrate that adequate information to produce both short and long-range fibrillar order is provided by the confining geometry and the triple-helical domain of the collagen molecule. These results further demonstrate that the triple helix in atelo-collagen carries long-range structural information that can be leveraged simply by confinement and concentration. This can relieve fibroblasts of the need to "stitch together" complex, highly organized 2-D+structures like the cornea. Rather, fibroblasts confine and concentrate collagen monomer while providing low-energy directional cues (such as active cell attachments to the matrix or merely the high aspect ratio "spindle" shape fibroblasts typically employ). Thus, cell organization may occur first, followed by organized matrix production, as was seen in the PHCSC-derived constructs.

Example 3

Geometric Guidance Cues Influence the Organizational Behavior of Collagen Fibrils Precipitated from Liquid Crystalline (LC) Phase Solutions of Monomer The concentration and precipitation of collagen monomers in the appropriate guiding geometry leads to the formation of fibrillar structures with organizations similar to those found in natural load-bearing tissues.

A. The Relationship Between Concentration and the Organizational Behavior of Collagen Molecules Both long and short range organization of collagen molecules are a function of monomer concentration and confining surface separation; monomer organization is readily translated to precipitated fibrillar organization.

Methods

Cold, acidic solutions of the atelo-collagen Type I monomers (Inamed, Fremont, Calif.) are dialyzed against 40% solution of 20 kMWCO polyethylene glycol (PEG) using 3.5 kMWCO dialysis tubing (Spectrum Labs, Rancho Dominguez, Calif.) to obtain the concentrations listed in Table 1.

TABLE 1

Parameters for Channel Depth and Concentration

| Conc (mg/ml) | Depth (μm) | | | | | |
|---|---|---|---|---|---|---|
| | 0.5 | 2 | 4 | 10 | 100 | 500 |
| 50 | ✓ | ✓ | ✓ | ✓ | ✓ | ✓ |
| 100 | ✓ | ✓ | ✓ | ✓ | ✓ | ✓ |
| 150 | ✓ | ✓ | ✓ | ✓ | ✓ | ✓ |
| 200 | ✓ | ✓ | ✓ | ✓ | ✓ | ✓ |
| 250 | ✓ | ✓ | ✓ | ✓ | ✓ | ✓ |

Figure 8:
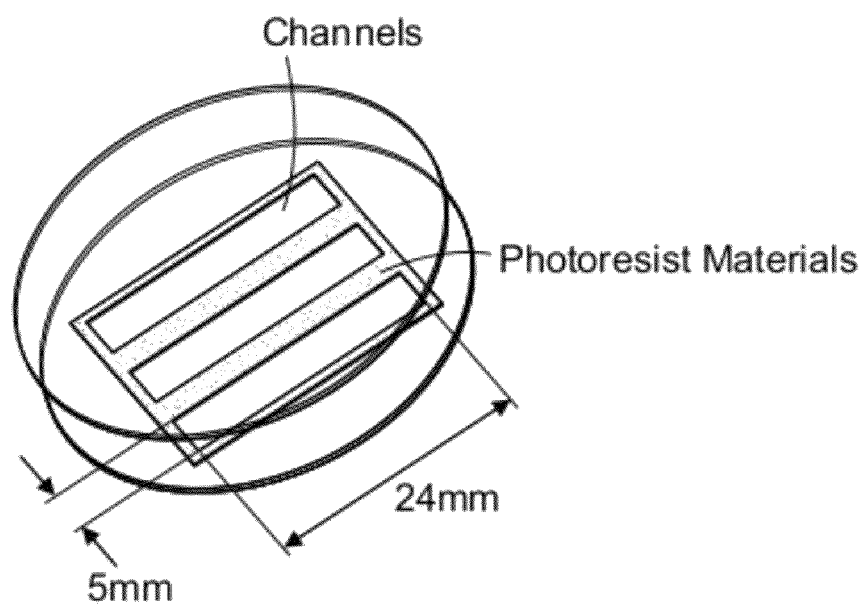
FIG. 8 is a diagrammatic representation of channels etched into a coverslip.

The solution is dispensed into guiding geometries (channels of varying depth etched into a coverslip as shown in FIG. 8). Briefly, the templates and microchannels are manufactured by spin coating a thin layer (120 nm) of PMMA onto the substrates (e.g, coverslips or silicon). In the case of a coverslip, an additional 5 nm layer of gold coating is added using an E-beam evaporator. The pattern of templates is written on the substrates using a supra 25 Zeiss SEM device equipped with a J, C, Nabity ver. 9—lithography and pattern generation system. The patterns are developed in a solution of MIBK and are etched to the desired depth using an ICP ether Dry plasma etch reactor.

Loaded channels are covered with a blank coverslip and stored at 4° C. for up to 96 hrs. Channel depths are chosen to correspond to natural length scales of the system—collagen molecule length, single and multiple tissue lamellar thickness (about 2 μm to about 100 μm), total thickness of a representative tissue (e.g., corneal stroma).

The triple helical domain can dominate organizational behavior of collagen at high concentration. However, the short non-helical terminal telopeptides (which may be important for cross-linking/mechanical strength) may influence the liquid crystalline organization. Thus, a subset of the experiments that produce the best organization are repeated using tropocollagen.

Acid-extraction of collagen preserves intact telo-peptides. Briefly, tropocollagen is obtained from bovine corneas following the method described by Trinkaus-Randall et al. (*Invest. Ophthalmol. Vis. Sci.* 32:603-609 (1991)).

Collagen fibrillogenesis is facilitated by neutralization and warming of the dense solution. Neutralization is accomplished by transfer of confined collagen in situ coverslips into a neutralized mixture of PEG in 1.5 M Trizma base solution (Sigma, St. Louis, Mo.) and allowing free ion exchange between two solutions through the porous photoresist. The collagen phase pH is monitored using pH sensitive dyes (Sigma, St. Louis, Mo.). Following neutralization, the monomers are incubated in situ at 37° C. for up to 30 days. Precipitated fibril alignment strength and lamellar angle changes are assessed by Differential Interference Contrast (DIC) microscopy and polarizing light microscopy (PLM) at 1 day, 2 days, 3 days, 7 days, 14 days, and 30 days.

DIC Microscopy is carried out as described by Petroll and Ma (*Cell Motility and the Cytoskeleton* 55:254-264 (2003)), with the exception that a Nikon TE-2000E inverted microscope equipped with a 60×1.45 NA oil immersion objective (Nikon, Melville, N.Y.) and Coolsnap EZ camera (Photometrics, Tucson, Ariz.) are used.

The large-scale organization and LC phasing of the collagen molecules is investigated using polarizing light microscopy (PLM) at time points (1 hr, 3 hrs, 6 hrs, 12 hrs, 24 hrs, 48 hrs, and 96 hrs). Quantitative Optical PLM is performed using an upright Nikon microscope equipped with a center-locked rotating stage and a Cri Abrio Micro Imaging system.

The ultrastructural organization and morphology of the fibrils (e.g., D-banding, fibril diameter, and fibril-to-fibril spacing) are investigated by standard TEM (sTEM) and Quick Freeze Deep Etch (QFDE). All collagenous constructs are processed routinely for sTEM as described in Guo et al., *Invest. Ophthalmol. Vis. Sci.* 48:4050-4060 (2007), with the following exceptions. 1% osmium tetroxide is used instead of 2%, and images are viewed on a TEM (JEOL JEM-1000, Tokyo, Japan). Confined samples are fixed by transferring them in situ to a fixative reservoir at 4° C. ON to allow for complete diffusion of fixative molecules. For QFDE imaging, samples are prepared as described in Guo et al. (supra); however, a custom modified CFE-40 Freeze fracture/freeze etch unit (Cressington Scientific, Watford, UK) is used, and images are taken on a JEOL JEM-1000 (Tokyo, Japan).

The tensile modulus of the construct is evaluated. All mechanical analyses are performed on collagenous constructs that are crosslinked using the primary fixation method described. Tensile material properties of the collagenous matrix are measured as described in Wan et al., *Thin Solid Films,* 425:150-162 (2003), with additional constraints and calculation of a buoyancy correction for sample immersion in 1×PBS. In-plane Young's modulus is reported.

Results

A clear, repeatable relationship is expected between concentration, surface separation and the organization (length scale and average angle of spontaneous direction changes) of collagen monomers in dense solutions. Monomer organization is directly translated to precipitated fibrillar organization, and the ability to predict and control matrix organization are established.

B. External Guidance Cues Influence the Organization of Precipitating Collagen Fibrils A close relationship exists between the orientation of elongated fibroblast cells in a confluent sheet and the organization of synthesized fibrillar arrays. External guidance cues (e.g., patterns on confining surface) with geometric scales similar to an elongated cell can influence the organization of adjacent collagen fibrils precipitated from dense solutions. This effect can propagate surface organization deep into the bulk collagen solution. A measure of the influence of a geometric feature on the bulk LC material is the "persistence length", defined as the maximum distance from the feature where fibril alignment is affected. To calculate persistence length, a z-stack (0.5 µm step) of images is captured. At each position, the angle of alignment and the strength of alignment is calculated to produce a 3-D field adjacent to the guidance cue. The "persistence length" is defined as the point where the angle of alignment is within 15% of the direction of the guidance cue, and the calculated strength of alignment greater than 95%.

Methods

Various high-aspect-ratio prismatic rectangles are formed on the surface of a coverslip (as described in Part A above). Table 2 shows the parameters for the length (L), width (w), and height (h) of the external templates. The scale of these dimensions match the natural length scales in ECM from monomer length to elongated cells. Number of runs per geometrical feature=3.

TABLE 2

| Parameters of External Templates | | | | |
|---|---|---|---|---|
| Width (w) and | Length (L, µm) | | | |
| Height (h, µm) | 0.3 | 2 | 5 | 10 |
| 0.3 | ✓ | ✓ | ✓ | ✓ |
| 1 | ✓ | ✓ | ✓ | ✓ |
| 2 | ✓ | ✓ | ✓ | ✓ |
| 4 | ✓ | ✓ | ✓ | ✓ |
| 8 | ✓ | ✓ | ✓ | ✓ |
| 15 | ✓ | ✓ | ✓ | ✓ |

Figure 9C:
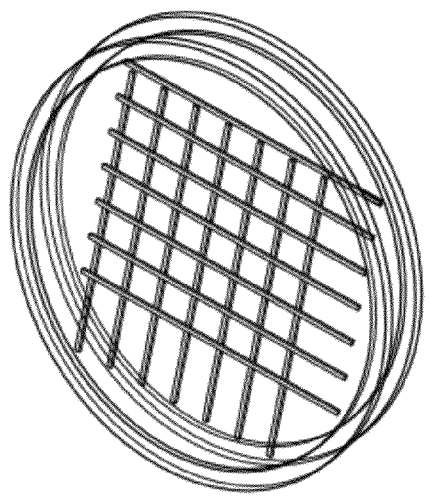
FIG. 9C is a schematic representation of perpendicular external templates.
Figure 9B:
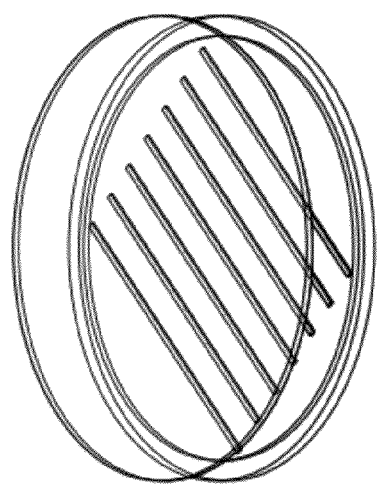
FIG. 9B is a schematic representation of multiple templates.
Figure 9A:
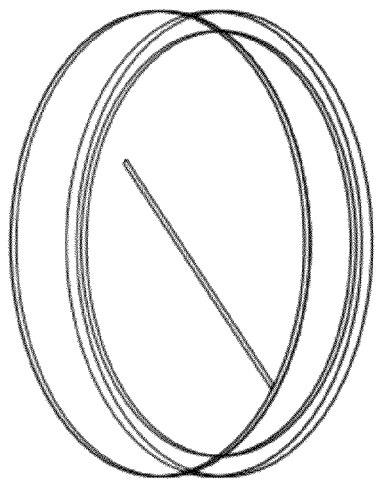
FIG. 9A is a diagrammatic representation of a single external template.

The rectangles serve as a single templating feature (FIGS. 9A-9C). The optimal concentration of atelo-collagen in solution (determined in Part A above) is then introduced onto the coverslip and confined from above with a featureless glass plate.

The feature that produces the maximum persistence length is multiply reproduced on the surface of a single coverslip with a spacing of twice the maximum persistence length found in the single feature experiment (FIG. 9B). Dense atelo-collagen solution is introduced and confined from above with a featureless glass plate. The persistence of the template-induced 3-dimensional organization into the bulk collagen is assessed. The alignment of collagen fibrils is quantified from DIC images using the edge detection method previously described by Chaudhuri et al. (*Pattern Recogn. Lett.* 14:147-153 (1993)). Briefly, the DIC image is convolved with two directional masks, $h_x$ and $h_y$, which results in the matrices $G_x$ and $G_y$. The gradient vector is calculated according to: $G=G_x^2+G_y^2$ and $\theta=\pi/2+\tan^{-1}(G_y/G_x)$.

The previous experiment is repeated with a second identical template coverslip (rather than a featureless surface) oriented perpendicular to the first to enclose the chamber (see FIG. 9C). The separation distance between the coverslips is reduced until the persistence length from each surface template overlaps. This experiment is repeated using tropocollagen.

Long range organization and alignment of precipitated fibrils is investigated using DIC and PLM as described in Part A above. The short range organization and morphology of the fibrils (e.g., D-banding, fibrils' diameter, and fibril-to-fibril spacing) are investigated by sTEM and QFDE imaging as described in Part A above. The tensile modulus of each construct is evaluated as described in Part A above. Each experiment is repeated 3 times.

Results

Specific external template parameters (geometries) are established that maximize the propagation of fibrillar organization into the bulk LC collagen.

C. Internal Template Guidance Cues Influence the Organization of Precipitating Collagen Fibrils Fibroblasts may control the alignment of collagen fibrils with their cell bodies or by extending filopodia. Whether internal templates of dimensions similar to filopodia (about 300 nm) can influence the organization of collagen over both short and long length scales is determined.

Methods

Figure 10C:
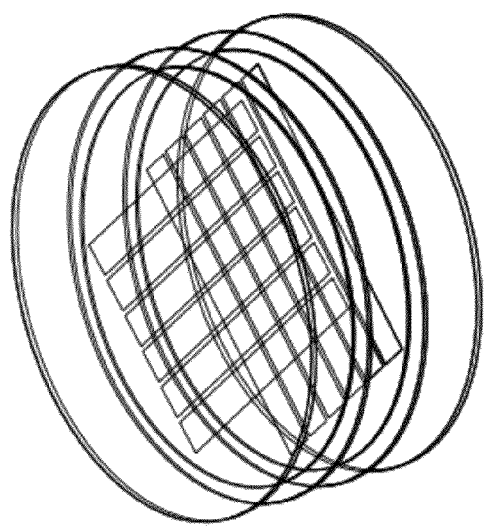
FIG. 10C is a schematic representation of perpendicular internal templates.
Figure 10B:
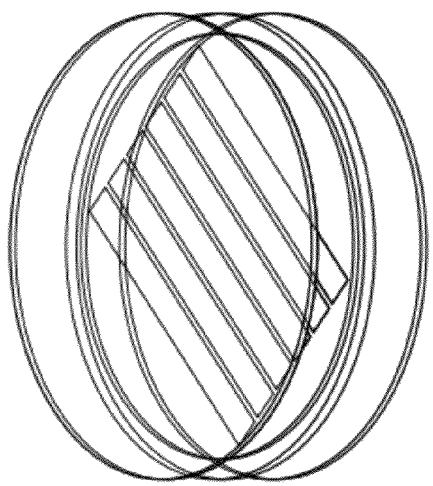
FIG. 10B is a schematic representation of multiple internal templates.
Figure 10A:
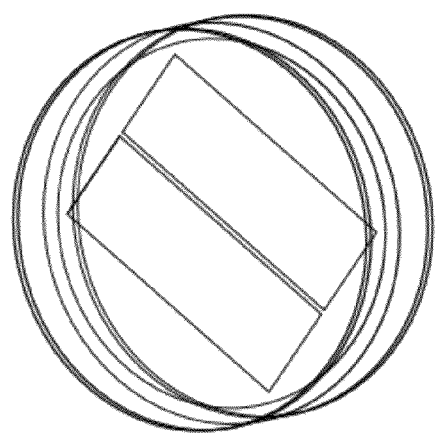
FIG. 10A is a schematic representation of single internal template.

The internal template comprises a prismatic square formed on a thin silicon wafer (FIG. 10A) and is placed between two thick gaskets. High concentration atelo-collagen is dispensed in the area surrounding the template and confined from both sides with two featureless coverslips. The fibrils are precipitated using the method described in Part A above. The width and thickness of internal templates are chosen based on the diameter of filopodia (300 nm and 500 nm) and elongated fibroblasts (1 µm and 5 µm). The length of all prismatic squares are 0.5 cm.

A series of parallel internal templates of similar geometries and a spacing of twice the most effective persistence length found using a single internal template are produced in a thin silicon wafer. Similar to the method used for a single internal template, atelo-collagen is dispensed, confined, and precipitated between two coverslips.

The previous method is repeated using two internal templating surfaces with similar geometries and perpendicular alignment. The spacing between the features on a single template is twice the persistence length found in the previous section. The distance between each of the internal templates to the adjacent confining coverslip is the same as the persistence length. This arrangement appears to result in complete organization of the fibrils between the coverslips.

DIC and PLM are used to investigate fibrillar organization across the construct, as described in Part A above. Alignment is evaluated using sTEM, and QFDE is used to further investigate the morphology and alignment of the resulting fibrils (as described in Part A above). The persistence length and the tensile modulus of each construct are evaluated as described in Part A above. Experiments are repeated 3 times.

Results

A combination of template geometry/spacing and collagen concentration are found that predictably control fibrillar organization at large distances from the template.

The natural length scale(s) associated with collagen organization at liquid crystalline concentrations (including characterizing spontaneous direction changes) are elucidated, along with a measure of the extent of the ability to control fibril organization via internal and external geometric guidance cues. This method provides a full assessment of the feasibility of utilizing the liquid crystalline behavior of collagen, along with guidance cues, to produce native-like fibrillar organization. Since surface features have the capacity to propagate organization over large distances into LCs, long-range control over the collagen is achieved.

Example 4

The Effect of Biologically Relevant Geometries on the Organization of Precipitated Fibrils The organization of precipitated fibrils from LC collagen monomers in various native developing tissues is in part determined by their naturally confining geometries. Such long-range influence is possible because of the natural tendency of the constituents of LCs to behave as a single unit.

A. Confined Collagen Monomers Within a Cylinder

Methods

Monomeric solutions of atelo-collagen are concentrated and injected into glass capillary tubing (BD, St. Louis, Mo.) of dimensions defined in Table 3.

TABLE 3

Parameters for Inside Diameter (R) and Length (L) of Capillary Tubing

| ID (R, mm) | Length (L, cm) | | |
|---|---|---|---|
| | 0.5 | 1 | 5 |
| 0.5 | ✓ | ✓ | ✓ |
| 1 | ✓ | ✓ | ✓ |
| 2 | ✓ | ✓ | ✓ |

Following injection, the ends of the tubing are blocked using 3.5 KMWCO dialysis tubing (Spectrum Labs, Rancho Dominguez, Calif.). Fibrillogenesis proceeds by neutralization through the dialysis tubing and warming as described in Example 3. A limited set of runs using tropocollagen are performed in the geometry that generates the best alignment.

After fibrils are precipitated (as described in Example 3), DIC microscopy is used to investigate the long-range organization of collagen fibrils. TEM and QFDE are used to evaluate morphology and short range organization.

Results

Confining a high-concentration solution of collagen molecules into a thin cylindrical tube (e.g., capillary tubing) causes the collagen molecules and the resulting precipitated fibrils to align in the same direction as the long axis of the cylinder (analogous to tendon/ligament). The resulting assembly of collagen molecules into long and parallel fibrils is similar to tendon fascicles.

B. Confined Collagen Monomers Within Concentric Cylinders

Methods

Figure 11:
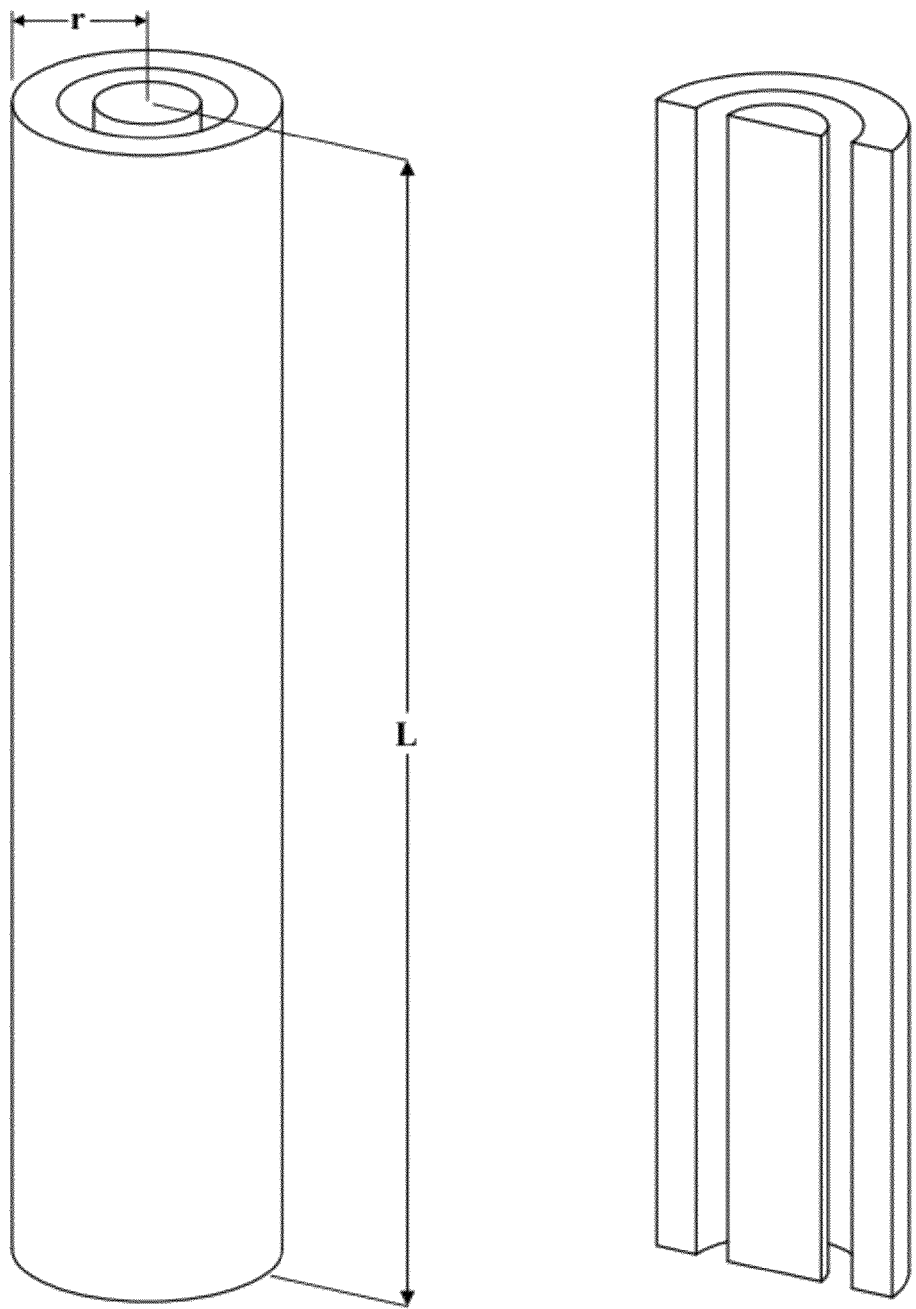
FIG. 11 is a diagrammatic representation of concentric glass cylinders to make concentric lamellae.

Highly-concentrated atelo-collagen molecules are injected into the space between concentric glass cylinders (BD, St. Louis, Mo.) (FIG. 11) with radius difference (r) (Table 4).

TABLE 4

Parameters for the Thickness (r) Between Two Cylinders and Length (L)

| Thickness (r, mm) | Length (L, cm) | | |
|---|---|---|---|
| | 0.5 | 1 | 5 |
| 0.5 | ✓ | ✓ | ✓ |
| 1 | ✓ | ✓ | ✓ |
| 2 | ✓ | ✓ | ✓ |
| 5 | ✓ | ✓ | ✓ |

The ends of the tubes are blocked using dialysis membrane, and the collagen solution is neutralized and warmed as described in Example 3. The geometrical parameters that provide the best result are tested with tropocollagen.

DIC is used to evaluate the organization and alignment of the collagen fibrils in large scale. TEM and QFDE are used to investigate the morphology and short range organization of the fibrils. Experiments are repeated three times.

Results

Confining collagen monomers in a thin space between two concentric cylinders causes precipitating fibrils to assemble into parallel lamellae tangent to the cylinder surface. The precipitating collagen fibrils are seen to organize into concentric lamellae similar to the collagen organization in annulus fibrosus.

C. Cornea-Like Collagen Organization

Methods

Figure 12:
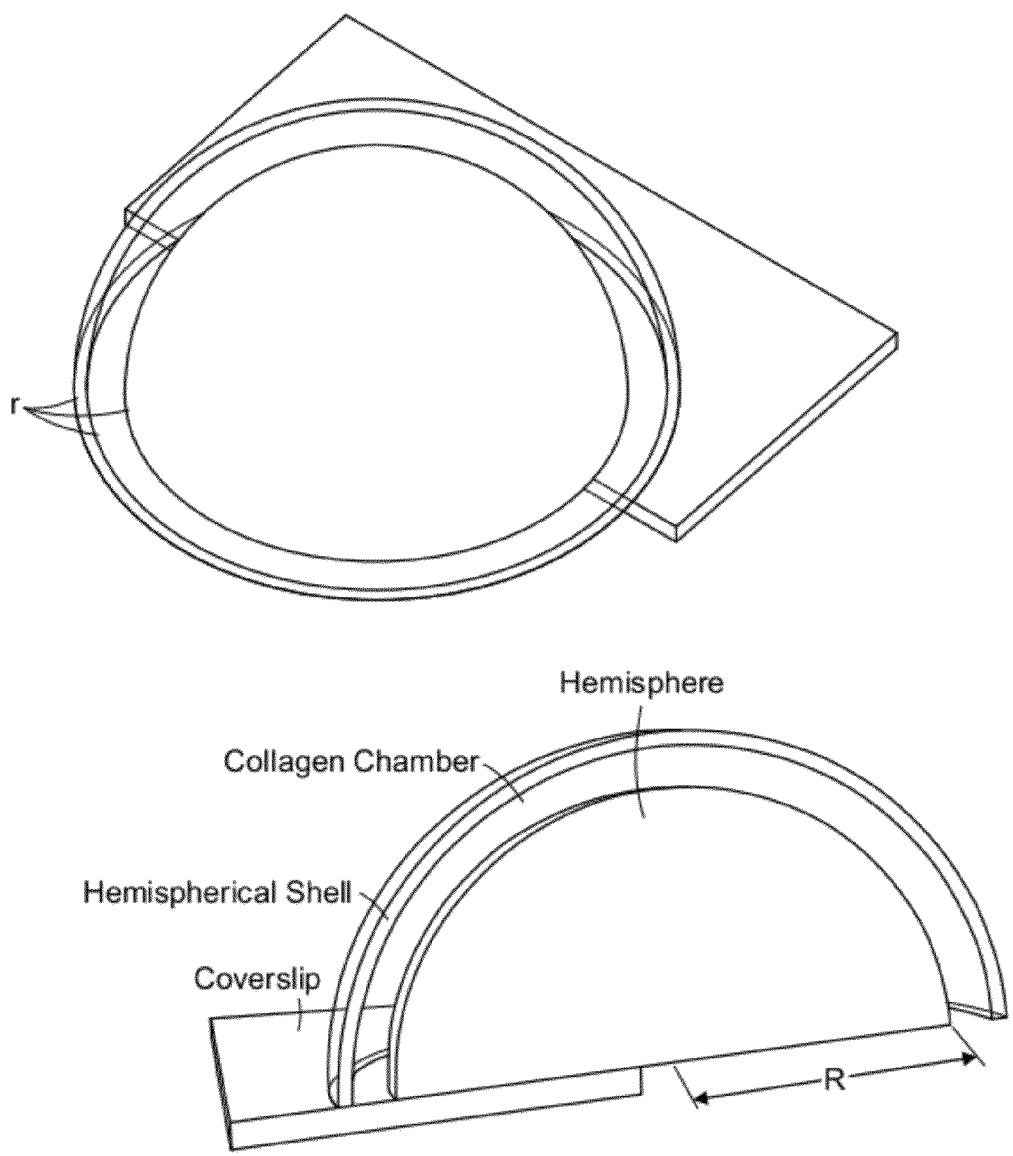
FIG. 12 is a diagrammatic representation of concentric hemispheres to make cornea-like collagen.

Atelo-collagen monomers are concentrated and confined between two concentric hemispheres (FIG. 12) that are obtained from McMaster-Carr (Princeton, N.J.). The dimensions are chosen to provide biologically relevant thicknesses (r) and radii of curvature, L (Table 5).

TABLE 5

Parameters for Hemisphere Radius and Thickness Between Two Hemispheres

| Thickness (r, mm) | Radius (L, cm) | | |
|---|---|---|---|
| | 0.5 | 1 | 1.5 |
| 0.5 | ✓ | ✓ | ✓ |
| 1 | ✓ | ✓ | ✓ |
| 2 | ✓ | ✓ | ✓ |
| 5 | ✓ | ✓ | ✓ |
| 10 | ✓ | ✓ | ✓ |

One hemisphere is fixed onto a coverslip and filled partially with collagen solution. The second hemisphere is positioned to produce the appropriate gap. The open gap is sealed with dialysis tubing and fibrils are precipitated by neutralization and warming similar to the method described in Example 3. The geometry that produces the best organization is used to repeat this experiment with tropocollagen.

DIC microscopy is used to investigate the long-range organization of the fibrils and lamellae. sTEM and QFDE are used to investigate the morphology and short range organization of the fibrils. Experiments are repeated 3 times.

Results

Confining a high concentration of collagen molecules into limited space with corneal-like curvature results in the formation of highly aligned fibrils arranged into orthogonal layers similar to native corneal lamellae.

The large scale confining geometry plays a significant role in the organization of precipitated collagen fibrils. The large length scales over which liquid crystals can be manipulated are sufficient to produce structures in precipitated collagen that mimic in vivo fibrillar organization.

Example 5

Auxiliary ECM Molecules Influence Collagen Fibril Morphology and Spacing

The collagen triple helix contains adequate information to produce both short and long-range organization. Collagen fibril morphology (such as diameter and D periodicity) and fibrillar spacing may be under the control of auxiliary ECM proteins (such as proteoglycans and glycosaminoglycans). The influence of controlling ECM molecules glycosaminoglycans, hyaluronic acid, proteoglycan core proteins, intact proteoglycans and collagen Type V on the morphology and structural organization of Type I collagen fibrils precipitated from dense solutions are determined.

The presence of highly-sulfated GAG chains or HA increases the rate of fibrillogenesis due to the co-nonsolvency effect that is produced by the presence of a high fixed negative charge density. The effects of three major non-collagenous components found ubiquitously throughout various connective tissues (keratan and chondroitin sulfates (KS and CS) and HA) are assessed. To demonstrate that the effect is physicochemical (rather than specific), a substitute hygroscopic molecule is also tested.

A. Highly Sulfated GAGs Fixed Charge Density Influences the Rate of Type I Collagen Fibrillogenesis Methods Purified bovine corneal KS and shark cartilage CS are obtained from Sigma (#K3001 and #C4384 respectively). Each GAG is serially diluted and pipetted into optimized cold, cholesteric collagen mixtures prior to concentration, and the resulting mixture is processed as described in Example 3 to allow assembly. The GAG content of concentrated collagen solutions is normalized to physiological range as outlined in Table 6.

TABLE 6

KS/CS Single GAG Addition Conditions Post Concentration

| GAG addition | Hrs of assembly | | | | | |
|---|---|---|---|---|---|---|
| | 6 | 12 | 24 | 36 | 48 | 72 |
| 120 µg/ml | ✓ | ✓ | ✓ | ✓ | ✓ | ✓ |
| 225 µg/ml | ✓ | ✓ | ✓ | ✓ | ✓ | ✓ |
| 500 µg/ml | ✓ | ✓ | ✓ | ✓ | ✓ | ✓ |
| 750 µg/ml | ✓ | ✓ | ✓ | ✓ | ✓ | ✓ |
| 1000 µg/ml | ✓ | ✓ | ✓ | ✓ | ✓ | ✓ |
| 7000 µg/ml | ✓ | ✓ | ✓ | ✓ | ✓ | ✓ |
| 20 mg/ml | ✓ | ✓ | ✓ | ✓ | ✓ | ✓ |

The rate of collagen fibril assembly is assessed using DIC microscopy (n=3) at strategic timepoints based on the developmental sequence of the chick cornea. Cuprolinic blue staining in conjunction with sTEM is used to assess fibril banding and GAG interaction (n=1). Briefly, high-resolution visualization of the sulfated GAGs is accomplished by en bloc Cuprolinic blue labeling as described in Scott (Coll. Relat. Res. 5:541-575 (1985)). Stained sections are imaged on JEOL JEM-1000 (Tokyo, Japan).

GAG chain assimilation is also tested in the entire construct on the light level scale by immunofluorescence microscopy against high and low KS (5D4 and 1B4) and CS (4C3 and 7D4) sulfation motifs (n=1).

To determine the assimilation of controlling molecules, constructs are oriented horizontally and vertically in embedding medium (for in plane and transverse sections), frozen, and sectioned on a cryostat. Labelling of the sections with antibodies raised against HA, highly-sulfated and lesser sulfated GAG motifs, and all PG core proteins are carried out as described in Young et al. (*Invest. Ophthalmol. Vis. Sci.* 48:3083-3088 (2007)). Constructs are observed using a Nikon Eclipse TE2000-E (Nikon, Japan) microscope at 25× magnification to achieve full thickness images. Antibodies and antibody specificities for immunofluorescence and immuno-electron microscopy are listed in Table 7.

TABLE 7

| Antibody | Description | Epitope | Pre-treatment |
|---|---|---|---|
| 5D4 | Mouse monoclonal IgG | Linear penta-sulfated sequences of N-acetyl lactosamine disaccharides of KSPGs with both GalNAc and Gal sulphated (Caterson et al. 1985, Mehmet et al., 1986) | None - reacts with native epitope |
| 1B4 | Mouse monoclonal IgG | Linear tetra-sulfated sequences of N-acetyl lactosamine disaccharides of KSPGs (Mehmet et al.., 1986) | None - reacts with native epitope |
| 4C3 | Mouse monoclonal IgG | Chondroitin-6-sulfate with non-reducing termination of GlcAβ1, 3GalNAc6S- (Plaas et al., 1997) | None - reacts with native epitope. Can be used in conjunction with C'ase ABC |
| 7D4 | Mouse monoclonal IgG | Lesser sulfated combinations of sulfated and non-sulfated disaccharide isomers in native CS (Caterson et al., 1995). Proposed as a marker for OA (Carlson et al., 1995) | None - reacts with native epitope |
| Lum$^{-1}$ | Mouse monoclonal IgM | Lumican core protein, amino acid sequence unknown | K'ase I/II/endo-β-gal to remove KS side chains |
| 70.6 | Mouse monoclonal IgG | Amino acid residues 50-65, termed the N-terminal cysteine cluster region of decorin (Sawada et al., 2002) | None - reacts with native epitope. C'ase ABC aids immuno-EM. |
| Anti-HA | Mouse monoclonal IgG | Hyaluronic acid, exact epitope unspecified (Immunology Consultants Laboratory Inc.) | None - reacts with native epitope |
| Anti-PEG | Rabbit polyclonal IgG | Terminal methoxy group of the PEG molecule (Epitomics) | None - reacts with native epitope |

Results

The addition of sulfated GAG chain fixed negative charge densities into a concentrated collagen solution expedites fibril formation in comparison to untreated controls. The greater the water attractive and absorptive tendencies, the more pronounced the co-nonsolvency effect. In vivo, corneal GAG chains undergo increasing net sulfation during embryonic development, and the water retentive and attractive properties of these KS and CS/DS GAGs are not equal. Control of the co-nonsolvency effect allows control of the rate of fibrillogenesis de novo.

B. Unsulfated HA Influences the Rate of Type I Collagen Fibrillogenesis and Morphology Methods Collagen assembly is initiated as described in Example 3, and HA is added to the concentrated collagen solution in the following concentrations: 0.5 µg/ml, 2 µg/ml, 4 µg/ml, 8 µg/ml, 20 µg/ml, 40 µg/ml, 100 µg/ml, 500 µg/ml, 1000 µg/ml, and 5000 µg/ml. Constructs are assessed on the same timescale as described in Part A above, in parallel with a negative control (no HA). Bovine HA is obtained from Sigma (#53728, Fluka).

The rate of collagen fibril assembly is determined as described in Part A above, using DIC to analyze the rate of fibril formation (n=3), sTEM (n=1), and immunofluorescence to investigate HA assimilation into (or independent of) the construct (n=1). Antibodies raised against HA are obtained from Immunology Consultants Laboratory Inc, Newberg, Oreg. (#MHGT-45A-Z).

Results

Increasing the presence of HA increases the rate of fibrillogenesis due to the physicochemical water sorptive capabilities of the group. HA is a ubiquitous ECM carbohydrate polymer that is a prominent feature of load bearing tissues such as cartilage. HA is transiently expressed in significant quantities during the early stages of avian development as the cornea swells and the template-like primary stroma is laid down. Over half the GAG assayed after 50 hrs of chick embryogenesis is HA.

C. A Substitute Hygroscopic Molecule with Potent Co-Nonsolvency Properties Influences the Rate of Type I Collagen Fibrillogenesis and Morphology Methods Atelo-collagen monomers are stimulated to assemble (as described in Example 3) in the presence of PEG 400, 600, 1000, 4000, and 8000 (NC9063854, AAB2179830, NC9395474, NC9090155, and BP233-100, respectively; Fisher Scientific (Pittsburgh, Pa.)). PEG is added using the optimum concentrations determined in Parts A and B above, and monitored on the same timescale, along with a negative control (n=2 for each concentration).

Constructs are assessed as outlined in Part B, above. Anti-PEG antibodies are obtained from Epitomics, Burlingame, Calif. (#2061-1).

Results

The substitution of GAG for a similarly hygroscopic synthetic macromolecule increases the rate of fibrillogenesis through physicochemical water sorption. PEG is a simple hydrophilic non-interacting polymer that can mimic the co-nonsolvency effect of sulfated GAG, which modulates the rate of collagen fibrillogenesis. A variety of comparatively small molecular weight PEG are used to approximate the fixed charge density provided by GAG in biological systems such as cornea, cartilage and intervertebral disc, and the resulting rate of fibrillogenesis is monitored. The rate of fibril assembly is expedited in comparison to control samples in the absence of HA/GAG and PEG. DIC images taken at specific timepoints are assessed to monitor the rate of fibril assembly between sulfated and non-sulfated GAG chain inclusion against comparable controls. These results determine the optimum conditions for controlled collagen precipitation.

D. PG Core Protein and Collagen Interaction Affect Fibril Banding and Diameter

The presence of either lumican or decorin core proteins nucleates self-assembling collagen fibrils to aid ordered banding and diameter control, and the increased order of assembly can inhibit the rate of fibrillogenesis. PG cores perform an interchangeable role in collagen fibril morphology control. Upregulation of lumican in keratocan knockout mice, and biglycan in decorin null mice both compensate to mask a phenotype. Double knockouts have cloudy corneas comprising abnormally thick collagen fibrils, with both increased fibril diameter and abnormal lateral growth.

Methods

Bovine lumican and decorin cores are isolated and purified from fresh bovine corneal tissue using a novel method to retain biological activity with a higher yield than conventional techniques. In this new method, corneas are frozen, pulverized and homogenized. Briefly, PGs are isolated by anion exchange chromatography on Q-Sepharose and treatment with chondroitinase ABC or keratanase I/II/endo-β-galactosidase for side chain removal. Lumican and decorin cores are purified by a second Q-Sepharose chromatography with affinity chromatographies on heparin—Sepharose and concanavalin A—Sepharose, as described in Brown et al. (*Protein Expr. Pur* 25:389-399 (2002)). Core proteins are concentrated and purified before filtering and storage at $-20°$ C.

Cores are combined with dense collagen mixtures prior to neutralization, concentration and assembly in the quantities outlined in Table 8.

TABLE 8

PG Core Protein Addition Conditions After Concentration

| Core protein | Hrs of assembly | | | | | |
|---|---|---|---|---|---|---|
| (μg/ml) | 0.5 | 1 | 6 | 12 | 24 | 36 |
| 5 | ✓ | ✓ | ✓ | ✓ | ✓ | ✓ |
| 10 | ✓ | ✓ | ✓ | ✓ | ✓ | ✓ |
| 50 | ✓ | ✓ | ✓ | ✓ | ✓ | ✓ |
| 100 | ✓ | ✓ | ✓ | ✓ | ✓ | ✓ |
| 200 | ✓ | ✓ | ✓ | ✓ | ✓ | ✓ |
| 500 | ✓ | ✓ | ✓ | ✓ | ✓ | ✓ |
| 1000 | ✓ | ✓ | ✓ | ✓ | ✓ | ✓ |

Initial experiments optimize the conditions through variation of parameters such as equilibrium time to allow core protein binding. Core protein additions approximate physiological quantities, with a range of concentrations added to result in an excess. Negative control experiments are also completed, for direct comparison.

The relationship between collagen fibril spacing and PG cores is investigated using DIC to monitor the rate of fibrillogenesis (n=3) and immunofluorescence to label cores in the whole construct (n=1), as described in Part A above. A closer examination of this relationship is also completed using immuno-electron microscopy (n=1). Constructs are subjected to low temperature embedding into lowicryl by automated freeze substitution (AFS, Leica), followed by core protein labeling using a Lumican (L-20) antibody (SC-27718, Santa Cruz Biotechnology, Inc., Santa Cruz, Calif.) and 70.6 anti-decorin.

For low temperature embedding, preservation of antigenicity and spatial distribution of PG cores, PGs and GAGs are achieved using automatic freeze substitution. Controlling molecules are immunogold labelled (primary antibodies shown in Table 7) as outlined in Young et al. (*Invest. Ophthalmol. Vis. Sci.* 48:3083-3088 (2007)). Labelled sections are viewed on a JEOL JEM-1000 (Tokyo, Japan).

Blocks are sectioned and stained as described in Part A above. Control experiments reflect (i) absence of primary antibody, and (ii) absence of secondary antibody.

Results

Banding patterns of constructs in the presence of lumican and decorin core proteins approach values seen in healthy ECM, (67 nm axial periodicity) compared to control samples.

E. Intact PG Affects Cholesteric Self-Assembled Collagen Fibril Banding and Spacing Methods Atelo-collagen are assembled in the presence of intact lumican and decorin isolated from fresh bovine corneal tissue, as described in Part B above. Pulverized fresh bovine corneas are extracted at 4° C. under guanidine extraction buffer for 48 hrs, 1 ml/100 mg tissue. Extracts are centrifuged after 24 hrs, the supernatant removed, and fresh buffer used to resuspend corneal fragments. After successive extractions, supernatants are combined and exhaustively dialyzed against DI. Guanidine extraction buffer is used at pH 5.8-6.8 and includes 4 M guanidine HCl (Sigma G-4505), 0.05 M NaAc (Sigma S-7545), 0.01 M $Na_2EDTA$, 0.1 M 6-amino (caproic) acid combined with protease inhibitors (5 mM benzamidine HCl (Sigma B-6506)), and 0.5 mM phenylmethylsulfonylfluoride in methanol immediately prior to use.

For core protein reformation and PG purification, DEAE and affinity chromatography are used as described Dunlevy et al. (*Invest. Ophthalmol. Vis. Sci.* 45:3849-3856 (2004)). Briefly, lyophilized (Laconic Freezone 4.5) extracts are reconstituted in 6.0 M urea containing NaCl, Tris, and CHAPS, and applied to DEAE Sepharose step columns equilibrated in the same solvent. PGs are eluted from the column, dialyzed against water, and lyophilized. Affinity purification of lumican and decorin is performed using monoclonal core protein antibodies, removing other proteins by washing from the affinity substrate in a column format. Core proteins are eluted from the column, dialyzed against $dH_2O$, and lyophilized.

PGs are added according to GAG content (assayed against a known shark cartilage standard by DMMB), reported in vivo. For microquantification of GAG, a DMMB dye binding assay is used. GAGs bind DMMB reagent via negatively charged sulfate groups resulting in a metachromatic shift (color change) in the absorbance maxima at 525 nm. Extracts are measured against known dilutions of CS used to generate a standard curve, and concentration is calculated from the resulting graph. 40 μl sample is tested for the presence of sulfated GAG with 200 μl DMMB reagent against shark cartilage (Sigma C-4384) standards at 525 nm. This assay loses linearity if GAG concentration is greater than 40 μg/ml, so samples are diluted if needed. Dimethylmethylene Blue reagent is prepared from 16 mg 1,9 dimethylmethylene blue (DMMB, SERVA #20335) in 5 ml 98% ethanol, 2 ml formic acid, 2 g sodium formate, 1 L with MilliQ $H_2O$, pH 6.8.

The method is first carried out using the GAG concentrations and methods described in Part A above (Table 6 supra).

PG additions are then modified as shown in Table 9, where corneal approximations are shown in white, and tendon in gray. Negative control experiments are also completed for direct comparison.

TABLE 9

KS/CS Mixture GAG Addition Conditions for Intact PGs

| KS | | Hrs of assembly | | | | | |
|---|---|---|---|---|---|---|---|
| (μg/ml) | CS | 0.5 | 1 | 6 | 12 | 24 | 36 |
| 225 | 120 | ✓ | ✓ | ✓ | ✓ | ✓ | ✓ |
| 1500 | 3000 | ✓ | ✓ | ✓ | ✓ | ✓ | ✓ |
| 2250 | 2250 | ✓ | ✓ | ✓ | ✓ | ✓ | ✓ |
| 3000 | 1500 | ✓ | ✓ | ✓ | ✓ | ✓ | ✓ |
| 2250 | 4750 | ✓ | ✓ | ✓ | ✓ | ✓ | ✓ |
| 3500 | 3500 | ✓ | ✓ | ✓ | ✓ | ✓ | ✓ |
| 4750 | 2250 | ✓ | ✓ | ✓ | ✓ | ✓ | ✓ |
| 7270 | 14540 | ✓ | ✓ | ✓ | ✓ | ✓ | ✓ |
| 11000 | 11000 | ✓ | ✓ | ✓ | ✓ | ✓ | ✓ |
| 14540 | 7270 | ✓ | ✓ | ✓ | ✓ | ✓ | ✓ |

DIC is used to monitor the rate of fibrillogenesis (n=3). Optionally, QFDE is used to determine construct morphology (n=2) (as described in Example 3), in addition to immunoelectron microscopy (n=1) to demonstrate collagen/PG interaction (as described in Part D, above). GAG chains are labeled using the same monoclonal antibodies described in Part A, above, and 70.6 anti-decorin. X-ray analysis (n=1) of full-thickness, mean center-to-center collagen fibril spacing in fully hydrated tissue is conducted.

For X-ray analysis, constructs are placed between two pieces of cling film to maintain hydration and minimize disturbance through handling, frozen at 253 K, and transported on dry ice to SPring-8 for examination using small-angle x-ray scattering. Experiments are conducted on beamline 40XU using a 30 μm diameter x-ray beam ($\lambda$=0.83 Å). Frozen constructs are thawed under ambient air while wrapped in cling film, and then secured onto a Mylar sheet and mounted into the x-ray beam path with the construct face perpendicular to the incident beam direction. Exposures are obtained from designated points across the entire construct, and the resulting SAXS patterns are recorded on a cooled CCD camera (ORCAII-ER, Hamamatsu Photonics) coupled with an x-ray image intensifier (V5445P, Hamamatsu Photonics) 3 m behind the specimen. Average x-ray intensity is recorded during data collection by an ion chamber placed between the incident beam and the specimen. X-ray patterns are analyzed using purpose-written, Unix-based software followed by a graphics and statistics package (Statistica; Statsoft, Tulsa, Okla.) as previously described by Meek et al. (*Prog. Retin. Eye Res.* 20:95-137 (2001)). In addition to measuring mean fibril to fibril centre spacing, the first order equatorial reflection is also used to estimate the degree of local order in the collagen matrix. Average collagen fibril diameter is also calculated, as described by Worthington et al. (*Intl. J. Biol. Macromolecules* 7:2-8 (1985)).

Data analysis is carried out in accordance with protocols described by Quantock et al. (*Invest. Ophthalmol. Vis. Sci.* 42:1750-1756 (2001)), using the position of the first-order equatorial reflection. The first subsidiary maximum of the experimental data is further analyzed to ascertain average fibril diameter, as described in Meet et al. (*Prog. Retin. Eye Res.* 20:95-137 (2001)). Constructs are assessed at the specific timepoints outlined, which are expanded into a binary search.

Results

Collagen interaction with intact lumican and decorin promotes collagen assembly into banded fibrils with altered interfibrillar spacing at a restored rate of fibrillogenesis. Lumican and decorin interact with collagen via a horseshoe-shaped core protein, with physico-chemical properties derived from their GAG content. The increased length and sulfation of CS and dermatan sulfate (DS) carried by decorin, and shorter KS chains on lumican, may be short and long-range mediators of fibril spacing.

The D-banding patterns of KSPG/collagen constructs approach closer values to those seen in cornea, with an increase in fibril order and more regular fibril diameter and spacing (as measured by x-ray diffraction) compared with controls. Restoration of assembly rate over PG core only assembly rates is observed.

F. Affect of Type V Collagen Co-Assembly on Self-Assembled Collagen Fibril Diameter and Spacing Whether manipulation of Type V collagen concentration enables control of fibril diameter in a self-assembling heterotypic collagen mixture (Types I and V) is evaluated.

Methods

Type V collagen is extracted and purified from bovine cornea in the presence of protease inhibitors using an acetic acid extraction followed by limited salt fractionation (as described in Example 3). The Type V collagen is combined with Type I collagen. Fibrillogenesis is induced as described in Example 3. Type I collagen is combined at various concentrations: 1%, 2%, 5%, 10%, 20%, 25%, 30%, and 40%, and the methods are repeated three times.

DIC microscopy is used to study the rate of fibrillogenesis (n=5). sTEM is undertaken to investigate collagen banding and fibril thickness after preservation through standard resin embedding (n=1), and QFDE is used to determine fibril morphology. To verify Type V incorporation into heterotypic fibrils (and link fibril diameter effects), immunoelectron microscopy is used (n=1), and antibody labeling is carried out after assembly for a representative number of samples (as described in Birk, *J. Cell Sci.* 95:649-657 (1990)). Monoclonal antibodies against Types I (5D8-G9/Coll, Abcam, Cambridge, Mass. #ab23446), and V (1E2-E4/Col5, Abcam #ab36382) can be used.

To elucidate the mechanism of ordered matrix assembly in vivo and produce cross-linked fibrils, selected methods are also conducted using the collagen precursor, procollagen. Procollagen terminal domains help to form the triple helix and inhibit fibril formation until suitable LC concentrations are reached in vivo, when a wave of protease enzymes are released allowing fibrils to rapidly assemble under templating geometries in the presence of ancillary molecules. To analyze this, Type I procollagen is extracted from fetal skin, obtained from Pelfreeze-bio (#57090-1). Procollagen is extracted and purified using the methods described by Byers et al. (*Proc. Natl. Acad. Sci. U.S.A.* 72:3009-3013 (1975)). Extracts are purified using DEAE-cellulose chromatography.

Type I procollagen is stimulated to assemble using (1) the optimized templating features from Example 3, (2) most favorable PG concentration for ordered fibril banding and spacing from Example 5, and (3) the optimal combination of both. These constructs are subjected to N- and C-terminal domain cleavage (extracted N-Proteinase, C-Proteinase) and evaluated in terms of rate of assembly (DIC), fibril banding and spacing (TEM, QFDE).

Results

Constructs assembled in the presence of Type V collagen show a fibril banding and diameter response to Type V collagen manipulation. The successful manipulation of collagen assembly and morphology by the addition of collagen controlling molecules enables control of assembly conditions and constitutes a first generation model of engineering biomimetic load-bearing tissue by design. Additionally, information is provided regarding the optimum conditions for de novo tissue assembly. The ersatz matrix serves as a test bed for strategic knock-out and knock-in experiments, where the roles of auxiliary ECM are identified.

Example 6

Strain-Directed Collagen Degradation in Native Tissue

A. Tensile Degradation Assay Experiments on Bovine Corneal Stroma

The cornea is unique in that it comprises arrays of uniform diameter Type I/V heterotypic collagen fibrils arranged in 2 μm thick lamellae that are parallel to the corneal surface, stacked orthogonal to one another and run uninterrupted across the entire cornea. Additionally, the fibrils do not interact with one another covalently and are generally thought to "float" in the extracellular matrix. Thus, a uniaxially loaded strip of cornea possesses a population of loaded fibrils (aligned with the tensile load) and a control population of unloaded fibrils (transverse and oblique to the load). To quantify the kinetics of native collagen cleavage in uniaxial strips of cornea, a miniature, thermally-controlled bioreactor capable of applying precise tensile loads/strains to tissue strips in an aqueous environment was constructed Church, et al. *BMES* Oct. 12, 2007). Using this new device and more active collagenase (e.g., purified collagenase or MMP), the kinetics of collagen degradation in strips of bovine cornea were examined.

Methods

Briefly, strips of devitalized bovine cornea were excised, debrided and loaded into the bioreactor. Strips were placed in load control mode with tensile uniaxial applied forces of 0.25 N, 0.1 N or unloaded (after creep in) and exposed to 0.05 M bacterial collagenase (crude). The detailed methods are described in Example 10, below.

Results

Figure 13A:
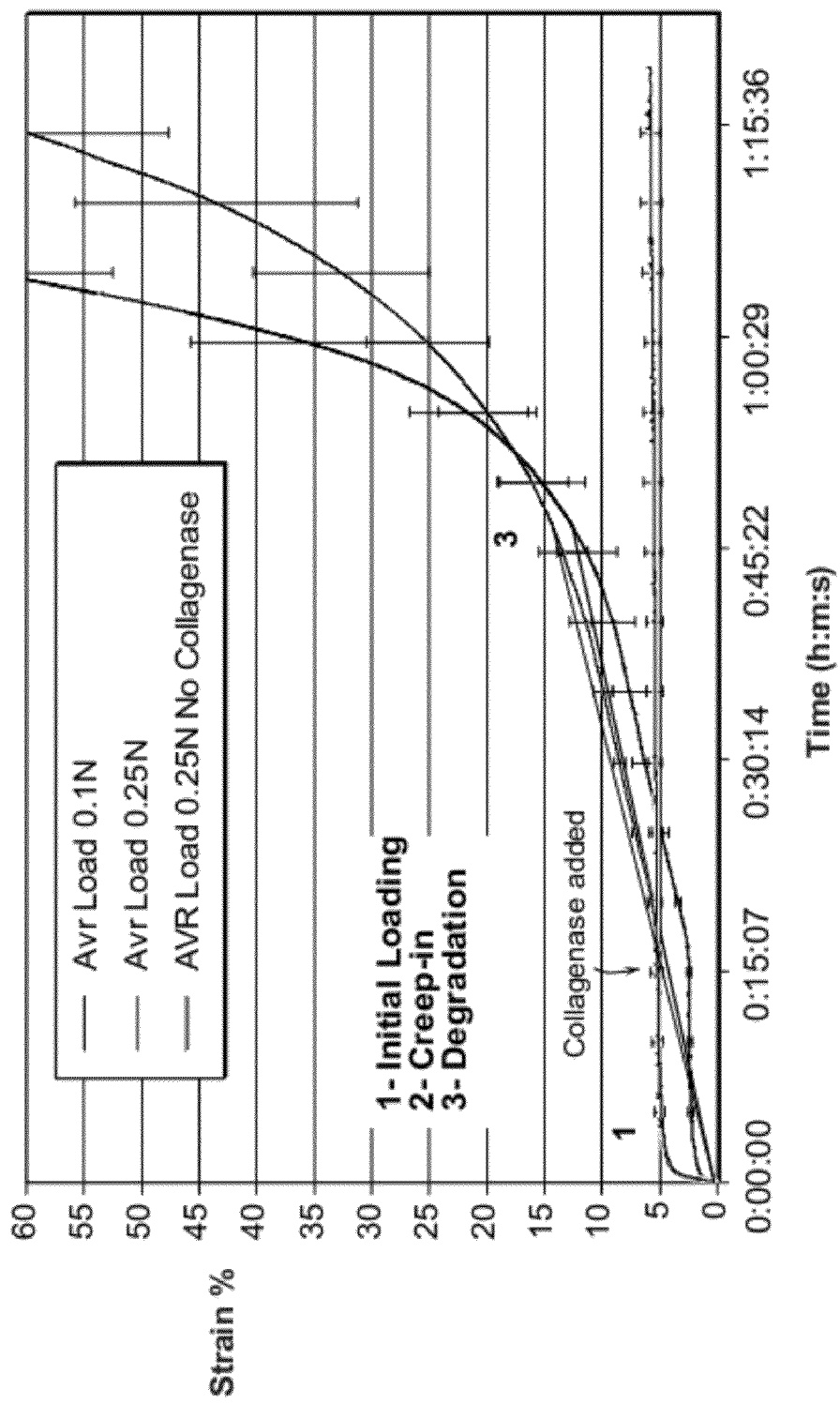
FIG. 13A is a graphic representation of % strain versus time curves for native tissue strip in a uniaxial loading bioreactor (load control).
Figure 13B:
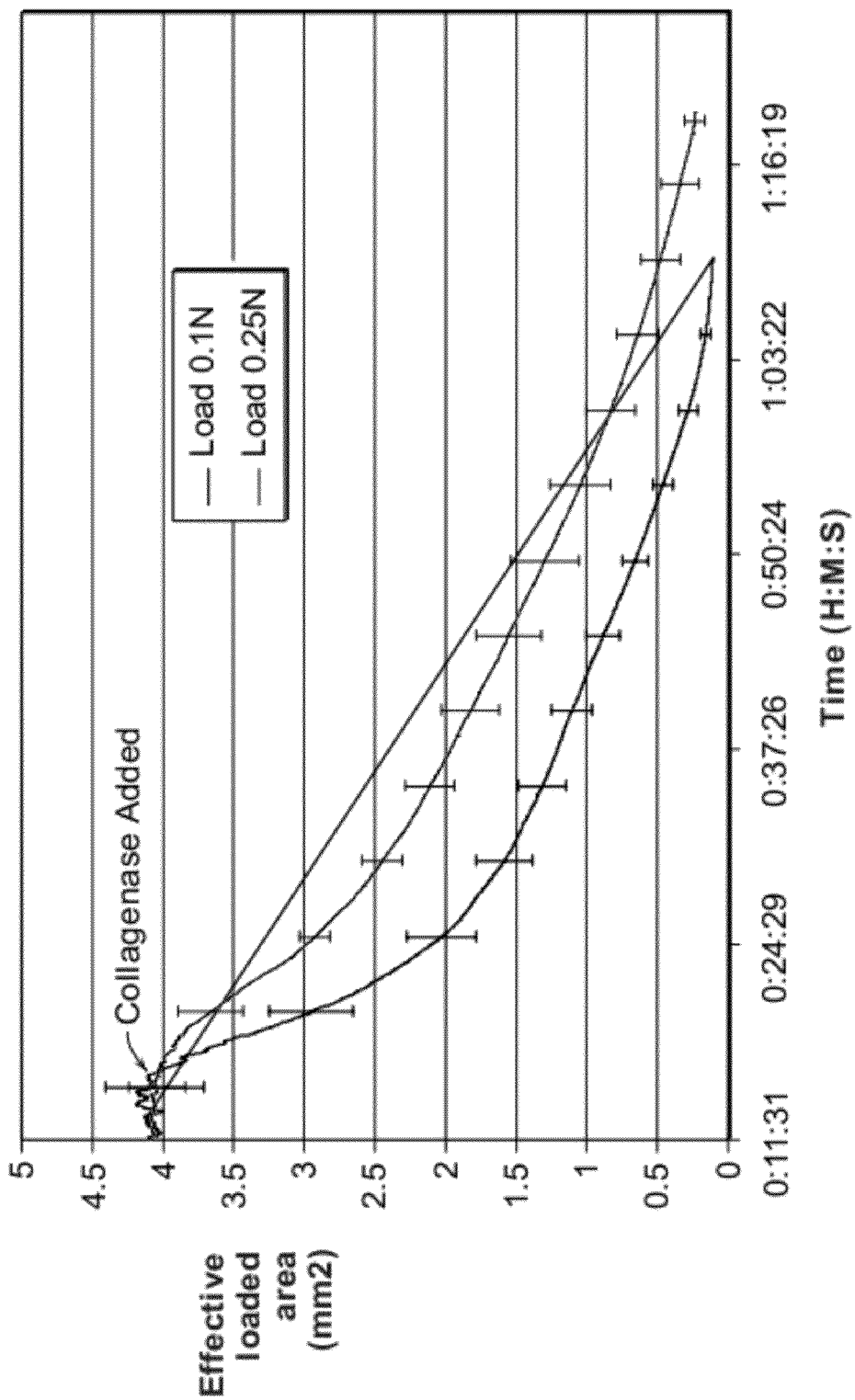
FIG. 13B is a graphic representation of estimates of effective loaded-area loss as a function of time for native tissue strip in a uniaxial loading bioreactor.

FIGS. 13A-13B are plots of the results that shows strain and area loss as a function of time. FIG. 13 shows degradation curves for native tissue strip in uniaxial loading bioreactor (load control). The strain versus time curves in FIG. 13A demonstrates that cornea tissue subjected to lower loads degrades to failure more quickly. In FIG. 13B, estimates of effective loaded-area loss as a function of time indicate that tissue subjected to lower loads lose area more rapidly during initial degradation. Increasing strain reduces rate of area loss (right side of curve). (Red—0.25 N; n=5); (Blue—0.1 N; n=6). Control curve shows minimal creep after 15 minutes (n=5). Tissue that was completely unloaded during degradation lost mechanical integrity faster than either loaded sample (n=3).

These figures demonstrate that the rate of area loss (cleavage rate of collagen) was significantly faster when the load was reduced (even at this high concentration of bacterial collagenase). Corneal strips degraded more slowly when loaded.

B. Compressive Degradation Assay on Bovine Articular Cartilage

Because collagen with lower tensile load is more susceptible to cleavage by collagenase, compressive mechanical overload of cartilage results in accelerated collagen catabolism. This has direct relevance to osteoarthritis in that Type II collagen that is relieved of its normal tensile load in cartilage (due to a local compressive overload) may be susceptible to enzymatic cleavage. Thus higher cartilage compression translates to lower collagen tension. When collagen fibrils are protected by the internal tensile strain generated by the GAG fixed negative charge density, "unloading" the fibrils in cartilage accelerates collagen degradation (in the presence of enzyme). Collagen was thus "unloaded" in cartilage plugs (by applied compression) in the presence of BC and the mechanical properties of the cartilage (stress evolution) were monitored.

Figure 14C:
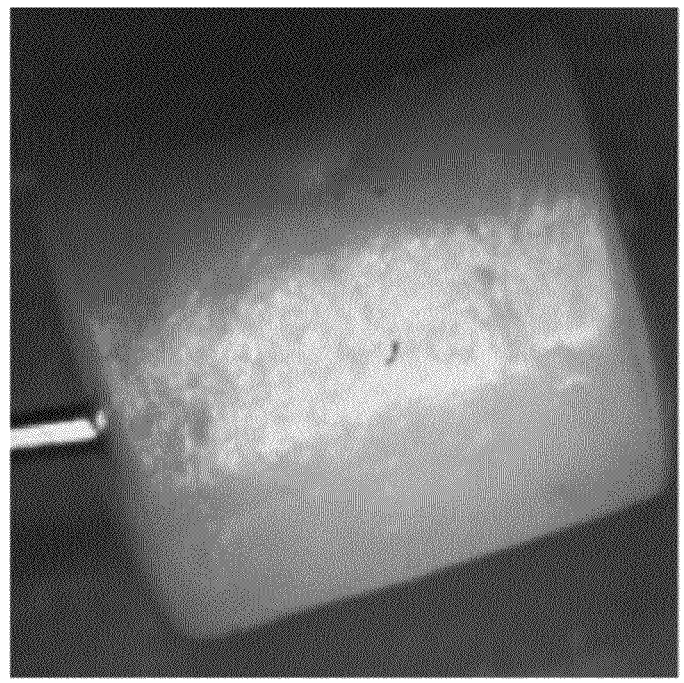
FIG. 14C is a representation of a photograph of a rehydrated cartilage plug ready to be warmed and mechanically examined.
Figure 14B:
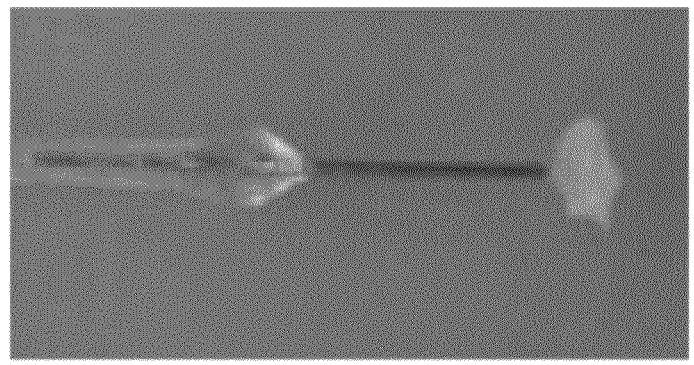
FIG. 14B is a representation of a photograph of a dehydrated cartilage plug loaded with MMP-13 solution.
Figure 14A:
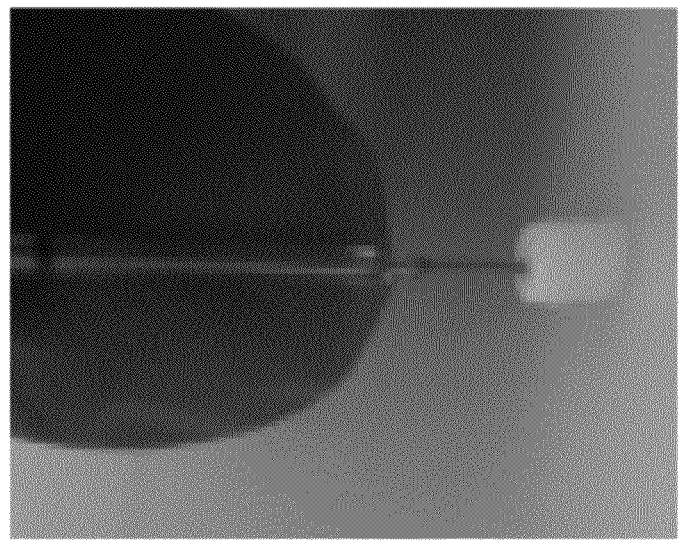
FIG. 14A is a representation of a photograph of a cartilage plug with a capillary tube needed inserted.

Methods 3 mm diameter, bovine tibial plateau cartilage plugs excised from bovine knee were infiltrated with precise microgram quantities of BC by transpiration. FIGS. 14A-14C show a capillary tube filled with enzyme solution and tipped with a needle inserted into a cartilage plug. The plug was dehydrated at 4° C., which resulted in the drawing of BC solution from the capillary tube. The specimen was then rehydrated in PBS at 4° C. and placed in an ELF3100 (Bose, Eden Prairie, Minn.) dynamic mechanical analyzer. This method allowed the precise "rapid" infiltration of a known quantity of enzyme directly into the center of a small sample volume. Static (unconfined) compressive strains of 10% and 20% were applied and the temperature was raised to 37° C. The stress evolution as a function of time was followed for up to three hours. The detailed methods are described in Example 10, below.

Results

Figure 15:
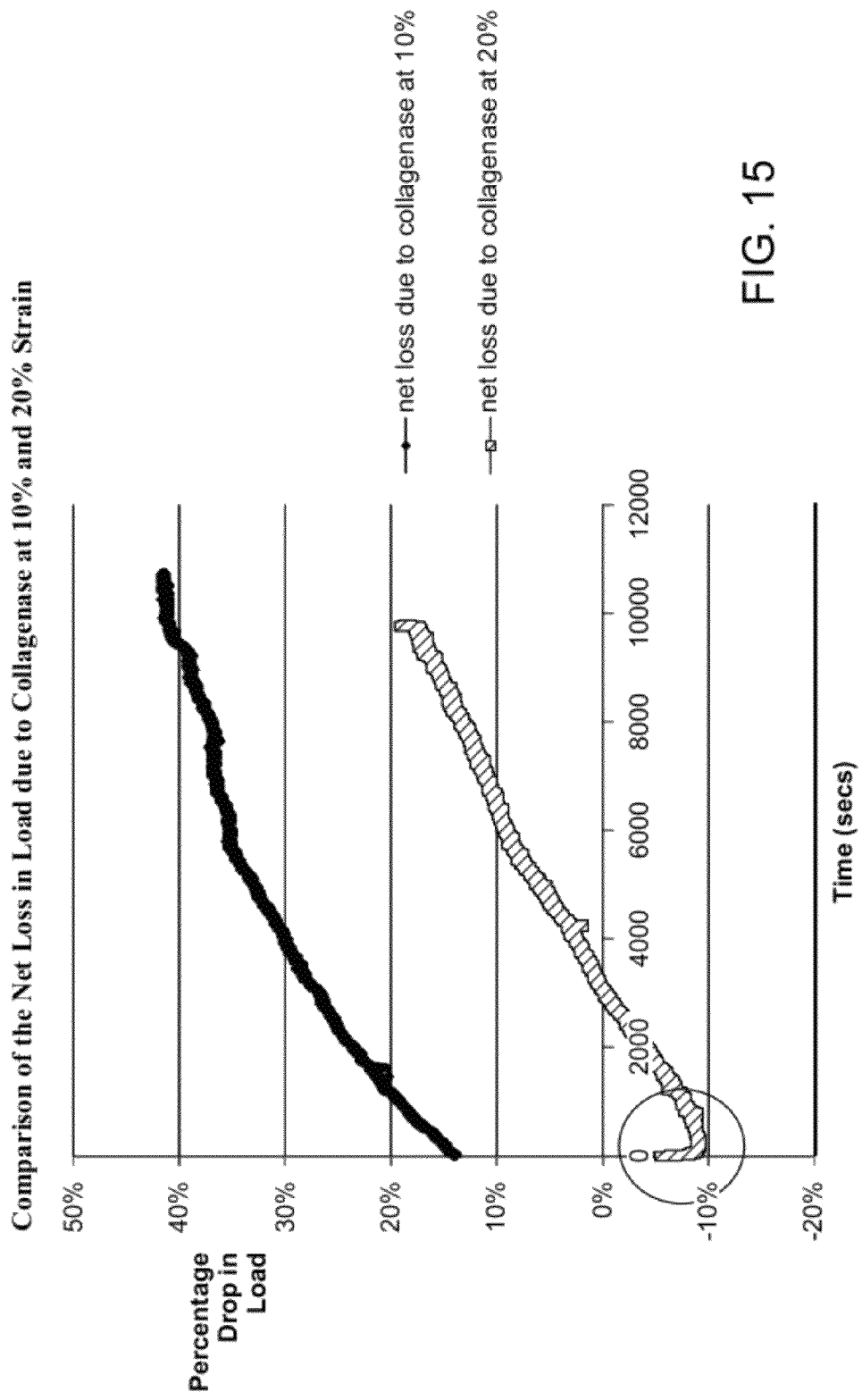
FIG. 15 is a graphic representation comparing the net loss (percentage drop) in load versus time due to collagenase at 10% and 20% strain.

The compressive modulus of rehydrated cartilage plugs following sham buffer or BC loading was always lower than fresh plugs, and untreated samples lost mechanical integrity with time in buffer and while under compression. This was due to loss of GAGs from the samples. FIG. 15 depicts the net loss in compressive strength for samples that were being degraded and losing GAG simultaneously. Compared to sham-loaded controls, the 20% strain sample first gained strength (circle), then lost compressive strength slowly, while the 10% strain sample lost strength continuously.

That the 20% strained sample actually gained compressive modulus indicated that loss of collagen (which restrains swelling pressure) was more rapid than in the 10% samples.

Example 7

Strain-directed Collagen Degradation of Reconstituted Collagen Gels

An environmentally-controlled microchamber to allow direct micromanipulation and observation of collagen gels was constructed in order to directly observe the mechanochemical kinetics of collagen fibril degradation by enzymes.

Methods

Microenvironmental Chamber

Figures 16A, 16B:
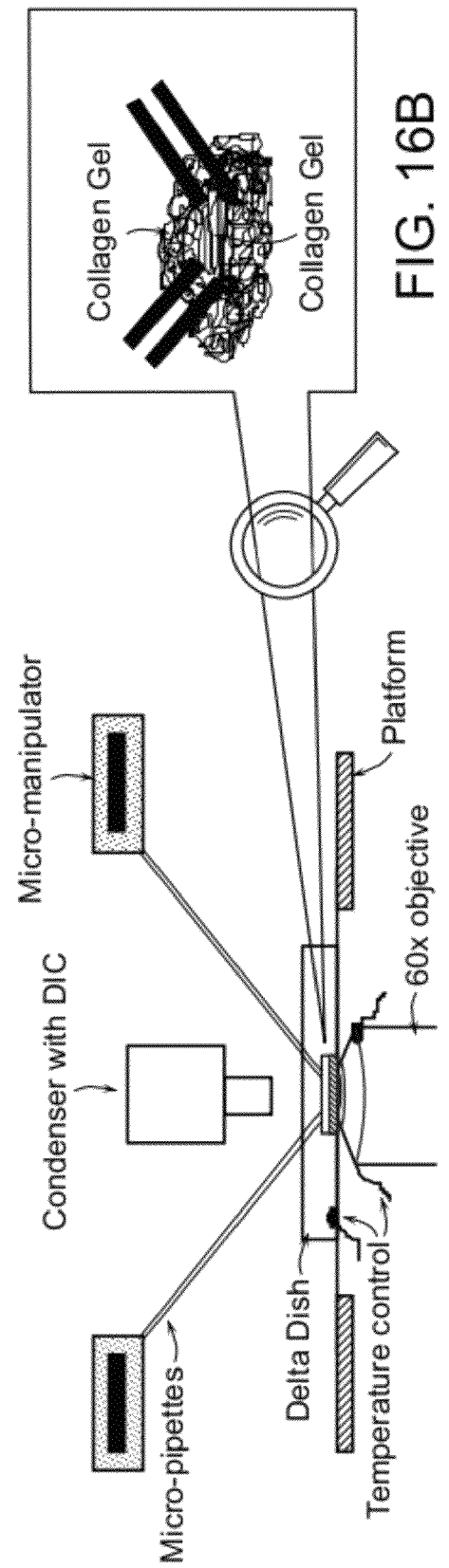
FIG. 16A is a diagrammatic representation of a system to carry out degradation of strained collagen in micro chamber while observing the process using DIC microscopy.
FIG. 16B is an inset schematically depicting the micropipette position and collagen gel in strained and unstrained form inside the micro chamber.

FIG. 16 depicts the microenvironmental chamber constructed on the surface of a Bioptechs Delta T4 (Bioptechs, Butler, Pa.) system comprising a delta-T dish (0.17 mm, 04200415B), triple plate stage adapter (PN 0402602), Delta T4 culture dish temperature controller (PN 0420-4-03) and objective heater controller (PN 0420-4-03). A small cylinder (height: 2.2 mm, inner diameter: 3.5 mm) was affixed to the Delta T4 glass surface. The initial reaction volume was created by placing 10 µl of collagen solution into the cylinder then covering it with objective oil (Cargille, non-drying, Type A, viscosity 150, Cedar Grove, N.J.) to prevent evaporation. The final reaction volume was created by dropping an additional 10 µl of collagenase solution through the oil.

Enzyme and Substrate.

Commercially available, pepsin-extracted, bovine, type I, atelocollagen monomers at a concentration of 3.0 mg/ml was used (PureCol™, NAMED, Fremont, Calif.). Extracted collagen monomers were kept from aggregating by storage in cold, acidic solution. Commercially available bacterial collagenase (crude, Sigma-Aldrich C0130, lot 016K1251) was used.

Optical Imaging.

Differential interference contrast (DIC) or Nomarski microscopy is a beam-shearing interference method that detects gradients in the index of refraction (optical path). Reconstituted type I collagen fibrils were resolved by DIC. DIC optics were mounted to a Nikon TE2000E (Nikon, Tokyo, Japan) inverted microscope equipped with a 60×, 1.45 NA Plan Apochromat objective and a digital camera (CoolSNAPHQ2 1394, Photometric, Pleasanton, Calif.). The microscope was also outfitted with a Perfect Focus® interference feedback stage controller capable of controlling vertical drift to less than 50 nm (Nikon, Tokyo, Japan).

Formation and Micromanipulation of Reconstituted Collagen Micronetworks.

To generate micronetwork strain, a pair of micropipettes were fitted to Eppendorf TransferMan® NK2 micromanipulators (Eppendorf, North America) and were mounted on the stage (H101A, Proscantm II, PRIOR Scientific, Rockland, Mass.) of the Nikon TE2000E. Prior to mounting, the tips of the pipettes (fire polished borosilicate with filament, OD 1.0 mm, ID 0.50 mm) were custom manufactured for minimum taper using a P-97 Flamming/Brown micropipette puller (Sutter Instrument Company, Novato, Calif.) with a five step program setting (Heat=712, pull=40, Vel=15, Time=150). To facilitate binding of collagen to the pipette tips, they were first plasma-cleaned (PDC-32G, Harrick Plasma, Ithaca, N.Y.) for 0.5 minutes at 50 watts and 200 mTorr. The pipettes were then functionalized by silanization (3 mercaptopropyl—trimethoxysilane) followed by N-(γ-Maleimidobutyryloxy) succynimide ester (GMBS) treatment. The functionalized micropipettes were positioned via the micromanipulator such that they could be observed in close proximity (about 20 μm apart) at 600×. Collagen monomers were prepared for fibrillogenesis according to the packet insert (by gentle mixing of buffer (PBS 10×), NaOH (0.1 M) and the collagen solution (3.0 mg/ml) in parts of 8:1:1). To produce a fibrillar network or gel, 10 μl of neutralized collagen in buffer was added to the Delta TPG dish, covered with the immersion oil, and the temperature was raised to 37° C. A sparse gel micronetwork formed both around and between the pipettes. The micromanipulators were then adjusted to produce a network strain of up to 50% based on initial pipette separation.

Collagen Network Degradation.

10 μl of 0.025 M bacterial collagenase in DMEM was dropped through the oil immediately following micropipette repositioning to permit interaction with the strained micronetwork. In this way, the timing of collagenase addition was controlled to account for stress-relaxation. The final concentration of enzyme-to-monomer resulted in a 3.125:1 ratio, allowing the presence of more enzyme molecules than available collagen monomers at all times in the chamber.

To analyze any systematic effect of enzyme diffusion delay on the calculated degradation rates, experiments were visually screened for unequal degradation onsets in the unstrained fibrils on either side of the strained fibrils. Further, a conservative set of statistical comparisons between the calculated degradation rates of the unstrained and strained fibrils were carried out to normalize for delay in the onset of degradation of the strained fibrils. The timing of collagenase addition was controlled by consistent addition immediately following pipette repositioning.

Image Signal Processing.

The DIC images extracted during the experiment were subjected to region of interest (ROI)-based edge detection for quantifying collagen degradation rates. To reduce intensity variations across a large field of view, smaller regions of interest were chosen for analysis to minimize the effect of spatial contrast variation on the edge detection algorithm. The contrast for each strained and unstrained ROI was adjusted to a fixed width gamma line in MATLAB (The Math Works, Inc., Natick, Mass.) to normalize fibril edge sharpness across time. The initial gamma line width was determined by the first image taken in the ROI and held constant for the remaining data in the image sequence. The contrast normalized images were then smoothed using a Gaussian filter by a small value (R=1) to reduce the background noise. Edge detection was performed on the temporal stack of strained and unstrained ROI images using a Canny-Deriche edge detection algorithm (alpha=0.5) in ImageJ software (NIH, Bethesda, Md.). The edge-detected 32 bit grayscale image output was converted to 8 bit, and the background noise (corresponding to fibril-free areas within each ROI) was subtracted using MATLAB. The summation of all of the pixel intensities (which reflect DIC gradient strength and thus diameter) in an image was assumed to represent the integration of fibril length (detected-edge length)×fibril diameter (gradient intensity) and thus represents a measure of the remaining fibril volume. Summation values for each ROI were normalized to percentages by dividing all values by the maximum value obtained for that ROI during the run. Thus the values obtained (which were interpreted as the percentage of remaining fibril volume in the 2-D slice), were plotted against time for both the strained and unstrained regions. The resulting plots tracked the rate of fibril volume loss due to enzymatic degradation of each of the collagen fibril populations in the ROIs.

Edge Detection Method Validation.

To validate the edge-intensity image processing method used to determine relative fibrillogenesis and degradation rates qualitatively, an ideal network of constant-diameter fibrils was simulated for a range of diameters and then evaluated using the same image processing method. Collagen fibrils are modeled as infinite cylinders in the plane of observation where the light scattering effects can be calculated by solving the cylindrical wave equation as shown by Bohren & Huffman, *Absorption and scattering of light by small particles*, New York: Wiley (1983). While the orientation of fibrils in reconstituted networks is random, DIC microscopy has excellent out of plane rejection and thus in-plane fibrils will dominate the intensity data. Forward scatter intensity profiles can be generated for a range of fibril diameters and in-plane angles with respect to incident light polarization, Op. A constant-diameter fibril network was simulated by randomly superimposing generated profiles for different values of θP with noise added. The DIC image of this simulated network was calculated to produce the final expected image.

Quick Freeze Deep Etch (QFDE) Imaging.

Morphology preserving QFDE imaging was used to evaluate the initial polymerized condition of the fibrillar networks. Formed collagen gels were slam frozen at −196° C. on copper blocks with a portable cryogen (Delaware Diamond Knives, Wilmingdale, Del.). The samples were transferred under liquid nitrogen into a custom CFE-40 freeze-fracture/freeze-etch device (Cressington, Watford, UK). They were then etched at 95° C. for 45 min and rotary shadowed at −130° C. with 2 nm platinum and carbon at 20° angle and backed by 90° angle carbon. Replicas were picked up on grids and imaged digitally at 70 kV on a Jeol JEM-1000 (JEOL, Tokyo, Japan).

Data Analyses and Statistics.

Figure 17:
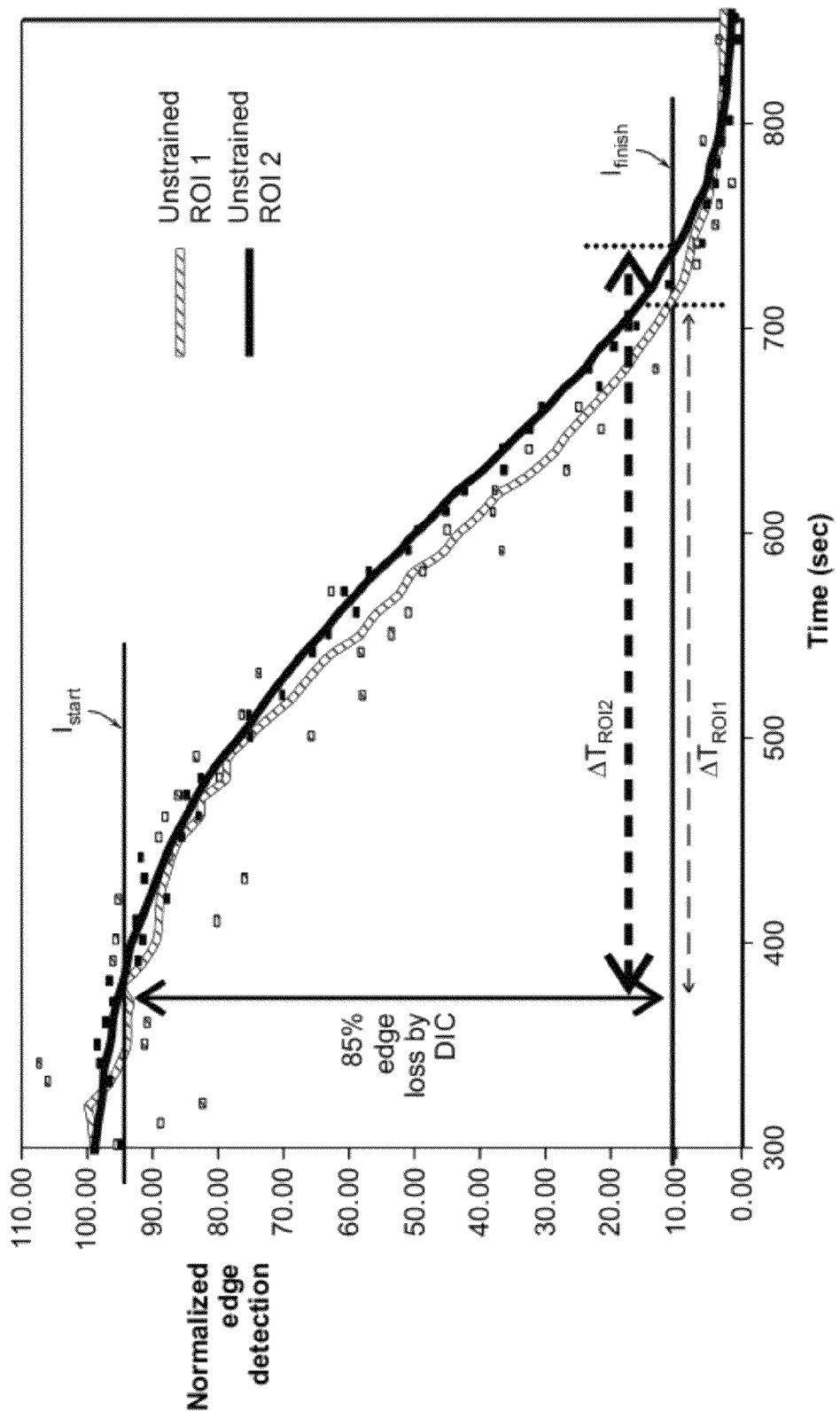
FIG. 17 is a graphic representation of the quantification of edge loss against digestion time ΔT in control sample (no strain).

Degradation times within specified ROIs were extracted from the curves produced by the image processing algorithm described above. The measured "degradation" time was defined as the time interval ($\Delta T$) between 95% ($I_{start}$) and 10% ($I_{finish}$) of $I_{max}$ (FIG. 17). The lower bound was chosen to be 10% of $I_{max}$, as there were multiple strained fibril digestion experiments that did not reach 5% of ($I_{max}$) prior to the end of the experiment. Degradation times from experimental runs were analyzed for Normality (Shapiro-Wilks test), skewness and kurtosis, and outliers removed using SPSS15. A paired, two-tailed Students T-test (Excel, Microsoft Corp.) was used to assess statistical significance ($p \leq 0.05$) in the processed data sets (n=10) and control experiments (n=2).

Results

Figure 18C:
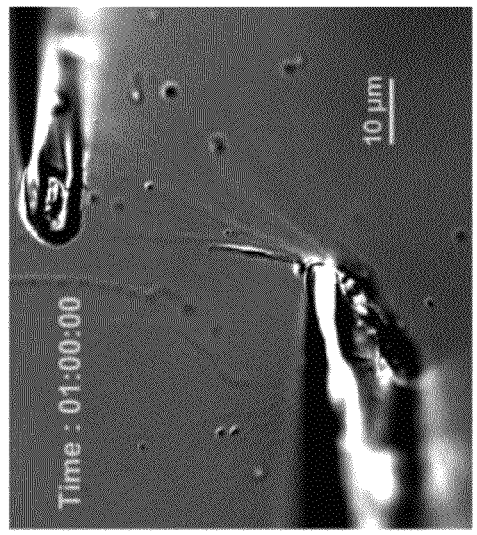
FIG. 18C is a representation of a DIC image of preferential, strain-directed degradation of a reconstituted collagen gel by bacterial collagenase at time 01:00:00.
Figure 18B:
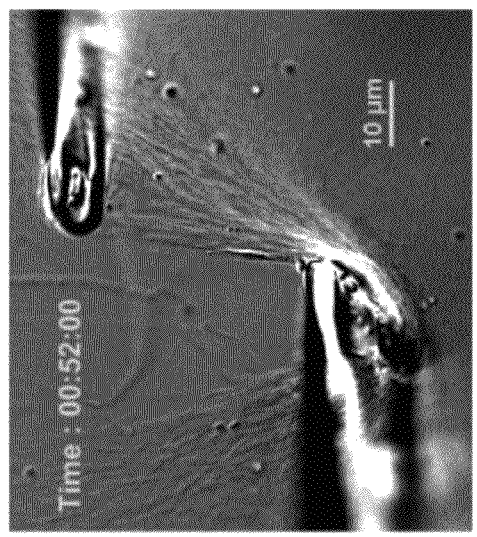
FIG. 18B is a representation of a DIC image of preferential, strain-directed degradation of a reconstituted collagen gel by bacterial collagenase at time 00:52:00.
Figure 18A:
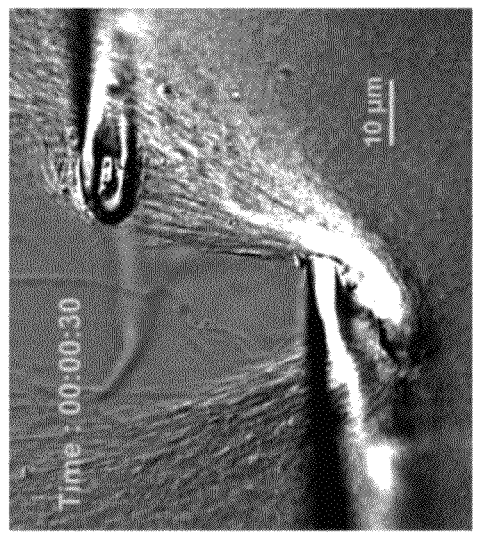
FIG. 18A is a representation of a DIC image of preferential, strain-directed degradation of a reconstituted collagen gel by bacterial collagenase at time 00:00:30.

FIG. 18 demonstrates that reconstituted collagen fibrils strained between two micropipettes degraded at a slower pace than unloaded control fibrils in the same gel. The access of the enzyme to the strained fibrils was not limited via strain-induced diffusion coefficient reduction as indicated by the loss of dense fibrils that were compressed under the bottom pipette (arrows). With bacterial collagenase, eventually all fibrils were lost to enzymatic cleavage. However, a statistically significant difference in the observed time to degradation (signal loss) between unloaded and loaded fibrils was detected, p=0.00129.

In these experiments, it was possible to discern that strained fibrils survived the enzymatic attack longer than unstrained fibrils. The video-enhanced and edge-detected DIC elucidated the surviving structures. Initial evaluation of simulated edge intensities using the image processing method described above showed a linear relationship between fibril diameter and DIC edge intensity for fibril diameters of 60-250 nm. Within this range, edge intensity provided a good qualitative, and potentially quantitative, method for evaluation of relative fibril diameter. Outside of this range, the edge intensity did not seem to vary much with diameter.

Figure 19:
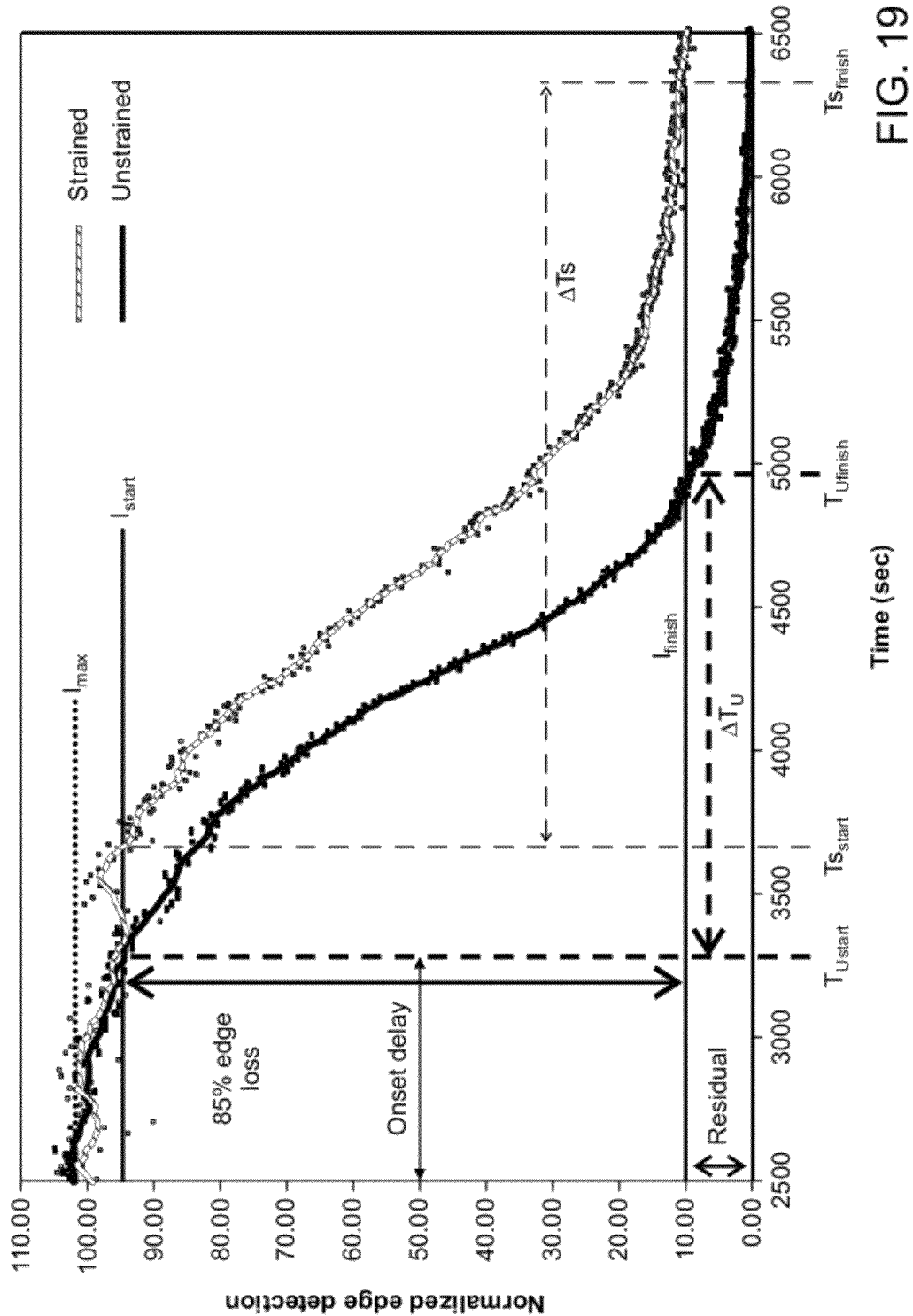
FIG. 19 is a graphic representation of the quantification of edge loss against digestion time ΔT.

FIG. 19 provides a temporal plot of the integration of detected edge strength, which was interpreted as being directly reflective of fibril volume, from two ROIs (strained or unstrained fibrils). Analysis of the data demonstrated that normalized degradation times for unstrained and strained fibrils were statistically different. Moreover, in every experiment, degradation was consistent: $\Delta T_S > \Delta T_U$. Quantitatively, the loss of edge detection by DIC between $I_{start}$ and $I_{finish}$ in strained and unstrained fibrils respectively, mean degradation time ($\pm$SE) $\Delta T_S$=1113$\pm$260 secs, and $\Delta T_U$=654$\pm$149 secs (p=0.0071). This significant difference included an allowance for the "delay" in the onset of degradation that could be attributed to diffusion differences across the experimental domain. However, the delay in the onset of degradation was consistent and only affected the strained fibrils. The effect of strain was efficiently isolated by the presence of control (unstrained) fibrils microns away from the strained ROI, therefore the reproducibility of the initial gel state was unlikely skewing the analysis.

Comparison of the average "onset" time for degradation (defined sd 95% of $I_{max}$); mean ($\pm$SE) for strained fibrils was $T_{Sstart}$=723$\pm$357 secs, and for unstrained fibrils was $T_{Ustart}$=586$\pm$323 secs. $T_{finish}$ time also increased under strain; with a mean ($\pm$SE) of 1836$\pm$587 secs compared to an unstrained mean ($\pm$SE) of 1240$\pm$454 secs.

The total loss of strained fibrils was also compared during the time it took for unstrained fibrils to fully degrade as defined by $I_{Ustart}$ and $I_{Ufinish}$ (a total of 85% edge detection loss). The loss of strained fibrils was significantly smaller during this period, with a mean fibril loss of ($\pm$SE) 63$\pm$4%, p=0.0002. When fibril degradation was defined to begin when the unstrained fibrils reached 95% of $I_{max}$ ($I_{USstart}$) and when degradation was defined to end when each set of fibrils reached 5% of $I_{max}$ ($I_{SFinish}$), the mean ($\pm$SE) $\Delta T_S$ was 1250$\pm$306 secs, and the mean $\Delta T_U$ was 654$\pm$149 secs, indicating a highly-significant difference in degradation time (p=0.0078). In control experiments where fibrils in the reconstituted matrix (including those between the functionalized pipette tips) were unstrained, the mean ($\pm$SE) digestion time $\Delta T$ (between pipette tips) was 510$\pm$180 secs, and in the surrounding matrix $\Delta T_U$ was 565$\pm$215 secs, which was a non-significant difference (p=0.5250). This implies that strain was attributed as the causative factor in degradation time differences.

MMP-8 was tested to determine if the strain-induced resistance of collagen to BC extended to this mammalian collagenase. FIGS. 20A-20C demonstrate that MMP-8 preferentially removed fibrils that were not under clear mechanical strain. The pipettes moved apart during the experiment due to loss of fibrils that had polymerized and tethered the pipette to the matrix. These fibrils are out of view of the images in FIGS. 20A-20C. In most cases, fibrils under load were retained for the duration of the experiment (unlike bacterial collagenase). MMPs are more sensitive to strain-induced molecular distortion given their specificity for one cleavage location and the reorientation of collagen momomer during cleavage.

Example 8

Strain-directed Collagen Degradation and Monomer Incorporation in Reconstituted Collagen Gels To determine whether strain preferentially protects loaded fibrils and also enhances their reinforcement and growth, monomers were assayed for incorporation into fibrils under strain.

Methods

Type I Collagen was polymerized around functionalized micropipettes as described in Part A above; however, during the polymerization process, the micropipettes were slowly moved apart (at a rate of about 1 µm/min-2 µm/min).

Results

FIGS. 21A-21D are DIC image sequences that demonstrate the preferential incorporation of monomers into a loaded cluster of fibrils between two pipettes that were moving apart. The initial collagen connecting the pipettes appeared to both thicken and extend in length. In the background, a random network of fibrils is shown gelling. This suggests that collagen monomers incorporate into fibrillar structures that are under strain. Further evidence is depicted in FIG. 20A, where fibrils that formed between two pipettes and between the left pipette and the gel were "strained" early in the polymerization process. The fibrils appeared "thicker" and the fibrillar structure was denser than background fibrils that formed with no load. Remodeling and growth of collagenous, load-bearing ECM can be accomplished efficiently and without direct cell intervention by the addition of monomer by collagen fibrils when loaded.

Example 9

Statistical Reaction-Diffusion-Strain Model of Collagen Catabolism

The kinetics of collagen catabolism by bacterial collagenase or human skin fibroblast collagenase follows Michaelis-Menten rate kinetics. When incorporated into fibrils, monomer availability is reduced due to fibril insolubility and steric hindrance leaving only surface monomers available for degradation. To incorporate strain-dependence into the reaction rate coefficients and to model the viscoelastic strain-behavior of loaded, degrading corneal strips, a 1-dimensional reaction-diffusion model was extended.

Methods

Figure 22:
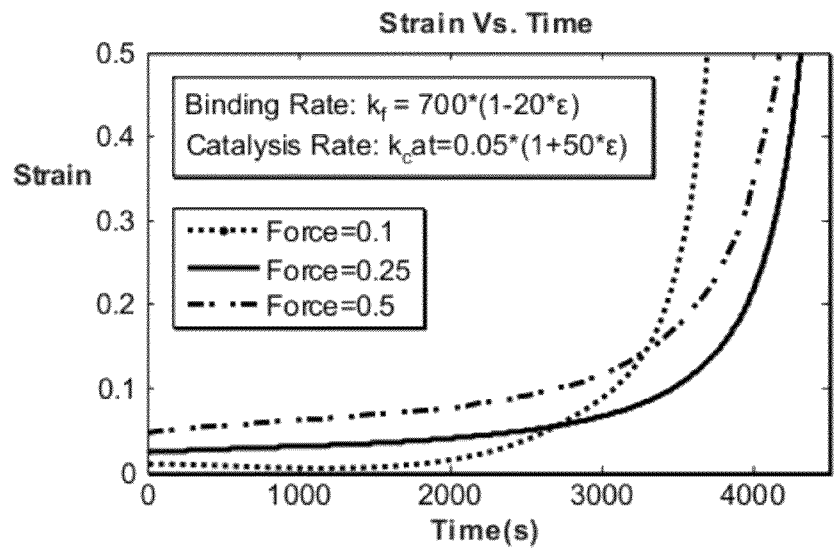
FIG. 22 is a graphic representation of strains at various times for corneal stromal collagen degradation by BC based on a model.

Both the forward binding rate coefficient and cleavage rate coefficient were assumed to possess simple bounded, linear strain-dependence (see FIG. 22). Since the kinetic parameters, $K_{cat}$ and $K_m$, for *Clostridium histolyticum* collagenase acting on Types I and III collagens are similar in magnitude to those of human enzymes acting on their preferred substrates, the data from Example 6 were qualitatively "fit" to the model.

Results

FIG. 22 shows a family of curves produced when the binding rate and catalysis rate coefficients were modeled as linear functions of strain. The data qualitatively matched that depicted in FIG. 13 (where the enzyme binding decreased with strain, but the cleavage rate increased with strain) and included a good fit of data from 0.5 N load control experiments.

To achieve the characteristic family of curves, the binding rate coefficient was forced to decrease with strain, and the cutting rate coefficient was forced to increase with strain. The net effect produced a "sweet" spot in the strain/degradation behavior of corneal collagen (about 4%), which can be maintained to protect a population of collagen fibrils. Strain-induced decreases in enzyme diffusion rates produced a similar set of curves. The strain-induced decrease in diffusion is about 54% for a change in strain of only 3%.

Example 10

Determination of the Degradation Kinetics of Whole Tissues

Collagen fibril survival is a function of the strain energy density and the concentration of catabolic enzymes present in the matrix. Native tissues, whose resident collagen fibrils are placed under varying strains, are exposed to catabolic enzymes (e.g., MMP-8, MMP-13, Cathepsin-K, and BC) and the relationship between strain and enzyme reaction rate kinetics is determined.

A. Relationship Between Strain and Enzyme Reaction Rate Kinetics in Native Tissue A combination of applied load/strain and enzyme concentration "protects" loaded fibrils from removal (but permits cleavage of unloaded fibrils). A uniform force is applied on one set of collagen fibrils from corneal stroma while another set remains unloaded. Corneal transparency allows real-time observation of degradation of off-axis fibril arrays via cross-polarizers. MMP-8 and BC are the enzymes for the cornea's Type I/V heterotypic collagen fibrils.

1. Titration of MMP and BC Against Applied Fixed Load

Combinations of load and enzyme concentration are established that remove unloaded fibrils.

Methods

Uniaxial tensile specimens are prepared from fresh bovine eyes (40-100 lbs, Research 87 Inc. Boylston, Mass.). Corneas with a surrounding scleral rim are dissected away from the globe and debrided prior to cell lysis by multiple freeze-thaw cycles. Freeze-thawing has little effect on corneal ultrastructure. A central corneal strip with inferior-superior orientation is extracted (0.7 mm thick×17.5±2.5 mm length×6 mm wide) and inserted into a custom-built bioreactor chamber, as described in Church, et al. *BMES Meeting*, Oct. 12, 2007. The scleral rim is fastened into custom grips. Silicon adhesive is used to protect attachment points from digestion. The chamber is filled with pre-heated media (DMEM with 1.0% gentamycin) and a small preload of 0.01 N is applied to produce an effective "zero" strain. Following a short "creep-in" period, activated MMP-8 (Chondrex Inc.—5001, Redmond, Wash.) or BC solution is used to replace the loading media.

MMP's are stored in Tris Buffer, pH 7.6, containing 0.05 M Tris, 0.2 M NaCl and 5 mM $CaCl_2$. MMPs are activated with p-AminoPhenyl Mercuric Acetate (APMA) at a 20:1 ratio and incubated at 37° C. for 1 hr before injection into the chamber.

A binary search is used to titrate a range of enzyme concentrations (beginning with a concentration equal to 1/10th the available collagen monomer in the corneal strip). Strips are held in load-control mode with applied forces representing sub-physiological, physiological and overload (0.1 N, 0.25 N, and 0.5 N) in the presence of the active enzyme at 37° C.

Strain is recorded. Polarization images are taken every 30 sec for the duration of the experiment with the cross polarizers aligned at 90-0° or 135-45° to the load axis. Control experiments are conducted with heat-deactivated enzyme. Significant deviation of the strain from average control strains at 3 hr results in a binary reduction in the titer concentration. Stable strain is defined as a deviation from control strains of ±2.0% after 3 hrs. Production of a "stable-strain" results in a binary increase in titer concentration. Once the titration threshold concentration is established, the assay is repeated 5 times and assessed for preferential loss of unloaded collagen as described below.

Polarizing Light Microscopy (PLM) is used to qualitatively observe collagen loss. Specimens are imaged (Prosilica-CV-640, Burnaby, Canada) through crossed-polarizers. Polarization images at the center of the sample are taken using uniform illumination with the load axis either aligned with one of the cross-polarizing lens axes or at a 45° angle to both lens axes. Images are examined qualitatively and quantitatively for loss or gain of birefringent signal intensity.

Briefly, the unique lamellar structure of central corneal fibrils is illuminated by passing polarized light through the sample. Alignment of one polarization axis with the specimen axis (load direction) illuminates off-load-axis (unloaded) fibrillar arrays. Loss of birefringence signal indicates loss of unloaded fibrils. Immunofluorescence is used to analyze Type I collagen loss across the entire sample in comparison to control samples, using a collagen I specific antibody (Abcam, Cambridge, Mass.) (n=2). TEM is used to examine this relationship on the fibrillar scale in a representative number of samples.

For TEM analysis, specimens from the tensile loading chamber are fixed while held to uniform thickness between coverslips. The center of each specimen is imaged at low magnification (3000×) both transverse to and in parallel with the applied load. The number of collagen fibrils in 5 random images oriented perpendicular to the load axis are counted. The number of perpendicular (not load bearing) fibrils are compared across digested and non-digested specimens.

Collagen loss into the media is also measured by a hydroxyproline assay. Released fibrils are hydrolyzed under 1 ml/mg construct 11.7 N HCl at 110° C. overnight, and then freeze dried to remove acid. Dried hydrolysates are reconstituted in DI before centrifugation to remove particulate material. Hydroxyproline residues are assayed in 30 ml triplicate against known standard dilutions of 0 mg/ml, 2 mg/ml, 4 mg/ml, 6 mg/ml, 8 mg/ml, and 10 mg/ml, with 70 ml diluent, 50 ml oxidant, and 125 ml color reagent, and read at 540 nm after 10-20 mins incubation at 70° C. Hydroxyproline content in the unknown constructs are calculated from the standard curve on each 96 well plate. Collagen content is extrapolated by multiplying hydroxyproline content by 7. (500 ml Stock buffer: 28.5 g Sodium acetate trihydrate, 18.75 g Tri sodium citrate dehydrate, 2.75 g Citric acid, 200 ml Propan-2-ol. Diluent: 100 ml Propan-2-ol, 50 ml distilled water. Oxidant: 0.7 g Chloramine T, 10 ml distilled water, 50 ml stock buffer. Color reagent: 7.5 g dimethylamino benzaldehyde, 9.64 ml Perchloric acid 70%, 1.61 ml distilled water (=60% acid), 62.5 ml propan-2-ol. Hydroxyproline stock solution: 10 mg purified hydroxyproline (Sigma) in 10 ml DI=1 µg/µl stock solution.).

Extraction of enzymatic cleavage rate coefficients is performed as described in Part 4, below.

2. Titration of MMP and BC Against Applied Fixed Strain to Determine the Threshold Concentrations That Yield Constant Load Combinations of strain and enzyme concentration are established that remove unloaded fibrils. Strain control is less dynamic and provides more stable data at each strain than load control.

Methods

Corneas are prepared and fitted into the chamber as described in Part 1, above. Strains are applied at about 2%, 3%, 4% or 5%. All specimens are assessed for morphological and biomechanical changes as described in Part 1 above using PLM, sTEM, and immunofluorescence. Extraction of enzymatic cleavage rate coefficients are performed as described in Part 4, below.

3. Effect of Cyclic Strain on the Rate of MMP and BC Cleavage

Dynamic strains of appropriate frequency alter effective enzyme reaction rate kinetics by modulating binding affinity and cutting efficiency. Examination of the collagen cleavage enzyme reaction equations reveals three reaction rate coefficients, forward binding of enzyme to monomer $k_m$, unbinding $k_u$ and cleavage $k_{cat}$. These rates possess different time scales (particularly due to the asymmetric nature of the forward and reverse binding coefficients time constants), indicating that cyclic loading produces marked accelerations or decelerations in collagen catabolism. Extracted enzyme reaction rates are used to determine the actual values of frequency and dynamic strain that provide maximum protection of loaded fibrils (see Part 4, below).

Methods

Corneal test specimens are prepared and loaded into the chamber as described in Part 1, above. The specimens are then subjected to dynamic strains (about ±1% and ±2%) around a fixed static strain (about 3% and 4%) and at multiple frequencies (about 0.5 Hz, 1.0 Hz, and 2.0 Hz). Samples are strained at static strain until the stress-relaxation transient dissipates (about 30 min). Dynamic strains are superimposed onto the static strain for a period 10 hrs in the presence of active (experimental) or inactive (control) enzyme. Force is recorded during the entire procedure. Corneal strips are assessed as described in Part 1, above, for morphological and biomechanical changes before, during and after enzyme degradation (using PLM, sTEM, and immunofluorescence). Strain and load information obtained is reported as Strain vs. Time, Strain Rate vs. Time, and Strain Rate vs. Strain Percentage in load control tests. For strain control tests, Load vs. Time and Load Rate vs. Time are reported. Collagen loss into the media is also measured by hydroxyproline assay at intervals that depend on enzyme activity. One procedure for which the titration produces good results (demonstrable loss of unloaded fibrils) is repeated with high-angle beamline. Collagen mass changes are assessed and collagen organizational changes during enzyme exposure are directly quantified by X-ray diffraction.

To measure fibril orientation using high angle X-ray diffraction, each cornea is mounted into a modified Perspex experimental chamber and exposed to the loading/enzyme conditions outlined in Parts 1 and 2, above. Media is removed to obtain a scatter pattern, and is replaced immediately after x-ray exposure (about 30 secs). A beam of parallel X-rays is scattered by an array of collagen fibrils perpendicular to the direction of the incident X-ray beam. At small angles, the equatorial X-ray scattering arises from the distribution of collagen fibrils, and at wide angles it arises from the distribution of collagen molecules within the fibrils arranged approximately parallel to the fibril axis. Irradiation is performed using a 0.1 mm cross section beam (Beamline I22, camera length 12 cm). Scattering patterns are collected on an image plate detector (Mar Research, Hamburg, Germany) at each point across a 25 point grid in the center of the corneal strip. Scattering from noncollagenous components of the tissue is subtracted, and the patterns normalized to account for fluctuations in x-ray beam intensity.

4. Extraction of Enzyme Reaction Rate Coefficients Using Statistical Reaction-Diffusion-Strain Model of Collagen Catabolism Methods A Reaction-Diffusion-Strain model of collagen degradation is used to fit the model output to data for both load-control and strain-control. Degradation of collagen (Types I-V) by bacterial collagenase and human skin fibroblast collagenase follow Michaelis-Menten rate kinetics. Insoluble fibrillar array degradation in a gel has been modeled using a coupled set of reaction-diffusion equations (see Tzafriri et al., *Biophys. J.* 83:776-793 (2002)). This model is modified for loaded corneal strip degradation. The geometric monomer availability constant, k, is changed in the following equation, where $a_m$ and $d_f$ are the corneal monomer intermolecular Bragg spacing and the fibril diameter, respectively.

$$k = 4\left(\frac{a_m(r,0)}{d_f(r,0)}\right)\rho_o^{1/2}$$

Collagen in a GAG matrix is modeled as a viscoelastic material with a time dependent modulus approximated using the standard linear model (SLM) and the following equation.

$$E(t) = \frac{E_1}{1 - \frac{E_2}{E_1 + E_2}\exp(-t/\tau)}, \tau = \eta_1 \frac{E_1 + E_2}{E_1 E_2}$$

For increased accuracy, $E_2$ in the SLM is replaced by 1 nested SLM and reproduces the strain response of a 0.25 N uniaxially loaded corneal strip. The viscoelastic parameters E1, E2, E3, η1 and η2 are extracted from the normalized load-control experimental data using a bounded Levenberg damped least squares method (see Bard, Nonlinear parameter estimation. 1973, New York; Academic Press).

To reproduce the loss of load-bearing fibrils in degrading tissue, the equilibrium modulus in the SLM is assumed to be proportional to the number of loaded monomers.

The model is discretized, the spatial second derivative governing diffusion is approximated using the centered difference method, and the system is integrated numerically.

Where s is the variable vector (concentrations of enzyme, monomer, enzyme-bound monomer, and degradation products), θ is the parameter vector (initial degradation rate constants, initial diffusion coefficients and strain-dependence parameters affecting both rate constants and diffusion coefficients), and h is the operator vector defined by the initial equations derived by Tzafriri et al, *Biophys. J.* 83:776-793 (2002). Differentiating the following equation with respect to θ:

yields the following set of differential equations in δs/δθ:

$$\frac{d}{dt}\left(\frac{\partial s}{\partial \theta}\right) = \frac{\partial h}{\partial \theta} + \frac{\partial h}{\partial s}\frac{\partial s}{\partial \theta}$$

This set is numerically integrated simultaneously with the original set from Tzafriri over time and space to obtain the sensitivity matrix $J_{t,T}$. From here the model is fitted to data obtained herein using a bounded Levenberg damped least squares method.

The principal adjustable parameters for the fit are the binding and cleavage rate coefficients. The oscillatory strain experiments described in Part 3, above, are run at frequencies and strains based on relevant time-scales (for diffusion and binding) extracted from the model.

To model corneal tissue, the tensile loading experiments are modeled as a 1-D problem across the corneal thickness assuming uniformity over the width and length of the tissue strip. The concentration of available monomer is calculated using fibrillar and molecular spacing data along with a geometrical correction. The strain distribution in the model cornea is based on statistical values of collagen fibril alignment derived from experimental data.

The diffusion coefficient of collagenase and monomer in the cornea is obtained by comparison of compiled diffusion coefficients for similar size molecules and Stokes radii. Gelman et al. (*J. Biol. Chem.* 255:8098-8102 (1980)) provide the diffusion coefficient of monomer in solution $(0.78 \times 10^{-7}$ cm$^2$/s) as well as in forming RCNs (monomer concentration 0.1 mg/ml, $0.15 \times 10^{-7}$ cm$^2$/s).

The bovine cornea comprises Type I/V heterotypic fibrils but is predominantly Type I collagen. Thus, collagen lysis rates in the model are approximated using known Type I collagen degradation data. For degradation of Type I collagen by MMP-1, $K_m$ is 0.8 µM and the catalysis rate constant, $K_{cat}$, is 34.2 h$^{-1}$. $K_m$ and $K_{cat}$ for the degradation of Type I collagen by *Clostridium histolyticum* collagenase (CHC) are 3.1-5.5 µM and 900-2100 h$^{-1}$, respectively. These values are used as initial values with which to seed the model.

If a single family of parameters (initial enzyme rate constants and enzyme rate constant strain-dependencies) predicts values in agreement with experimental data for a specific setup and load function, then the model is valid for that load function.

Results

The model fits experimental data for values of reaction-rate coefficients that depend on strain either linearly or with a low order function. The forward binding coefficient, $K_m$, decreases linearly as a function of strain, while the cleavage rate constant, $K_{cat}$, increases linearly with strain.

A clear, consistent relationship between strain and the reaction rate coefficients is obtained. A "target" strain (as a function of enzyme concentration) is identified that can protect loaded fibrils while allowing enzymes to remove unloaded ones. Such a relationship is used in the engineering of tissue.

B. The Relationship between Strain and MMP Reaction Rate Kinetics in Native Tissue Increasing compressive load on cartilage leads to increased collagen catalysis by MMP-13 and Cathepsin K. MMPs and Cathepsins play a role in the degradation of cartilage in osteoarthritis. Unloading collagen can enhance catabolism via enzymes and may be involved in the initiation and progressive nature of the disease. Chronic local compressive overloading of cartilage can lead to chronic tensile unloading of the internal collagen network, making the network susceptible to cleavage by available MMPs or Cathepsin K.

1. Titration of the Concentration of MMP-13 and Cathepsin K Against

Equilibrium Hydration in Cartilage Plugs Under Static Osmotic Stress

Methods

Cartilage samples (6 mm diameter, 4 mm length) are excised from the superficial and middle regions of bovine tibia articular cartilage and transpiration-loaded with MMP-13 or Cathepsin K (in activation buffer) for 12 hrs at 4° C. Enzyme loaded samples are rehydrated in 0.15 M NaCl containing 300 mM L-threose (Sigma, St. Louis, Mo.), 5 units/ml penicillin (Sigma), and 5 µg/ml streptomycin (Sigma) for 24 hrs at 4° C. before enclosing inside dialysis tubing (1000 Da, Spectrum). MMP-13/Cathepsin K thermosensitive activation is induced by incubation at 37° C. 50 ml-80 ml calibrated, osmotically active PEG-20 kD (Fluka, Buchs, Switzerland) solutions are used to exert osmotic stress on the cartilage plugs as described by Basser et al., *Arch. Biochem. Biophys.* 351:207-219 (1998) and Verzijl et al., *Arthritis Rheum.* 46:114-123 (2002). The tensile stress on the collagen network is calculated from the "balance of forces" at equilibrium hydration, as described in Basser et al., *Arch. Biochem. Biophys.* 351:207-219 (1998). For each PEG concentration, MMP-13 concentration (beginning at 0.1× collagen monomer concentration in cartilage) is incrementally decreased using a binary search, to find the concentration at which the equilibrium hydration is no different from controls (indicating total collagen fibril protection by internal tensile stress). The experiment is run four times. Control experiments are conducted using activation buffer containing heat denatured MMP-13/Cathepsin.

Equilibrium hydration is plotted as a function of enzyme concentration and internal tensile load on the collagen as defined in Basser et al., *Arch. Biochem. Biophys.* 351:207-219 (1998). Digested explants are processed as described in Part A, above, for sTEM and immunofluorescence with SPM239 against collagen II (Abcam, Cambridge, Mass.).

Results

An inverse relationship between internal collagen stress and titrated MMP/Cathepsin K concentration (and thus a directly proportional relationship between compressive stress and collagen catabolic rate) indicates that compressive overload of cartilage, which leads to lower internal collagen tensile stress, can lead to collagenolysis.

2. Titration of the Concentration of MMP-13 and Cathepsin K Against

Equilibrium Hydration in Cartilage Plugs Under Cyclic Strain

Methods

The protocol described in Example 6 is performed with MMP-13/Cathepsin K and with (6 mm diameter×4 mm length) cartilage plugs. Briefly, enzyme loaded cartilage explants (removed and transpiration-loaded as described in Part 1, above) are rehydrated in DMEM for 5 hrs at 4° C. Enzyme thermosensitive activation is induced at 37° C. in the controlled environment of a compression bioreactor (Bose/Enduratec ELF 3100 Dynamic Mechanical Analyzer, Bose Corp., ElectroForce Systems Group, Eden Prairie, Minn.). The compressive piston assembly is precisely manipulated using LinTalk software to determine "zero" strain and the applied DC offset strain is set to 10%, 20%, or 30%. Cyclic strain amplitudes of ±2% and ±4% are applied at frequencies of 0.5 Hz, 1 Hz and 2 Hz. Load cell data are monitored continuously via the LabVIEW interface during the degradation. After 3 hr, the samples are returned to "zero" initial strain while load is monitored for one hour. A similar enzyme titration is used to find the concentration of MMP for which the load at "zero" initial strain does not rise above "zero," indicating little or no collagen catabolism. For this concentration of enzyme, the procedure is repeated four times. Control experiments include a series of statically-loaded runs and a complete rerun of all "good" experiments with heat-denatured enzyme.

GAG loss into the surrounding media is quantified using DMMB assay (as described in Example 5), and collagen loss by hydroxyproline assay (as described in Part A, above). sTEM and immunofluorescence are also carried out on a representative number of samples, as described in Part A, above.

Results

Changes in the titrated enzyme concentration (compared to static loading) are detected that depend on both the amplitude and frequency of the cyclic strain. A clear repeatable relationship between degradation rate (measured by equilibrium swelling of plugs) and the loading regime is determined.

Example 11

Analysis of the Mechanochemical Kinetics of Reconstituted Collagen Networks (RCNs) During Degradation and Polymerization Reconstituted collagen networks resist enzymatic degradation when "strained" and preferentially incorporate free collagen monomer into "loaded" fibrils. Collagen degradation and polymerization depend on the applied mechanical environment. The effect of mechanical force/strain on the kinetics of collagen degradation and polymerization in reconstituted strained fibrillar networks is quantified.

A. The Kinetics of Collagen Monomer Incorporation/Polymerization Under Mechanical Tensile Load Load enhances the polymerization rate of collagen self-assembly in the direction of mechanical tension. Collagen self-assembly is mechanosensitive in vivo, and can therefore be modulated in vitro through appropriate loading and monomer concentration. Manipulation of these factors enables the determination of the reaction conditions to control fibril diameter and organization/alignment. The dynamic polymerization of monomers in solution during the application of strain to assembled fibrillar arrays is directly quantified.

Figure 23:
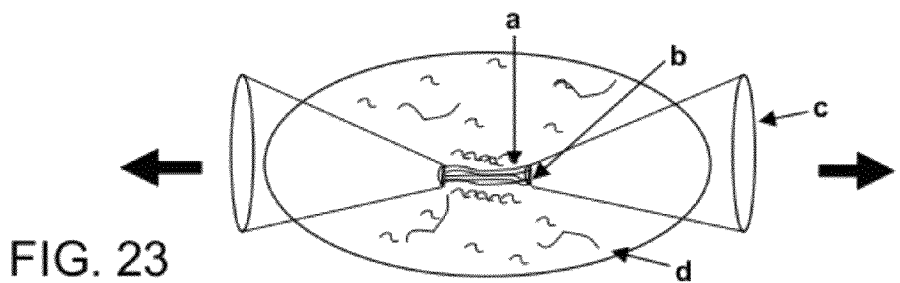
FIG. 23 is a diagrammatic representation of a device for measuring the kinetics of collagen monomer polymerization, where (a) indicates FITC labeled collagen monomers polymerizing onto stretched fibrils, (b) represents stretched collagen fibrils, (c) represents micropipettes (programmed for inducing static/cyclic strain), and (d) depicts collagen fibrils formed in unloaded matrix.

1. The Effect of Constant Strain-Rate on the Kinetics of Collagen Monomer Incorporation/Polymerization Methods Bovine Type-I collagen is self assembled (as described in Example 7) around micropipettes and equilibrated for 2 hrs. Following application of a starting strain (5%, 10%, or 20% of the initial pipette separation of 5 µm) the pipettes are separated at constant rates of 0.0, 0.25, 0.5, 0.75 and 1.0 µm/min while FITC labeled bovine Type-I monomer (Arthrogen-CIA®, Chondrex, Inc., Washington) and neutralization buffer are co-injected slowly (at a rate of about 0.025 µl/min) to produce a constant supply of fresh monomer (see FIG. 23). Concentrations of 0.05, 0.1, 0.5, and 1.0 mg/ml FITC labeled collagen are used. Fibrils in the surrounding media are used as unloaded controls. Monomers can "slide" relative to one another in strained, uncrosslinked RCNs. Local matrix strain is extracted using embedded microbeads or quantum dots. Each experiment is performed 3 times.

Collagen monomer incorporation is examined at intervals and quantified using fluorescence microscopy (FITC excitation λex=490 nm, emission λem=520 nm). Briefly, corneal strips are oriented horizontally and vertically (for in plane and transverse sections) in a large droplet of Tissue Tek (Miles, Ind., USA), and then processed as described in Young et al. (*Invest. Ophthalmol. Vis. Sci.* 43:2083-2088 (2007)). A Nikon Eclipse TE2000-E (Nikon, Tokyo, Japan) microscope is used to observe the constructs at 25× magnification to achieve full thickness images.

To track fibrils during the entire experiment, low-light-intensity, shuttered DIC imaging is used and combined with fluorescence images to produce movies of gel remodeling. Fibril ultrastructural morphology is investigated using sTEM. For sTEM, collagenous tissue/RCNs are processed routinely for sTEM as described in Guo et al. (*Invest. Ophthalmol. Vis. Sci.* 48:4050-4060 (2007)) and are viewed and digitally photographed using a JEOL JEM-1000 TEM (Tokyo, Japan)

Results

Collagen monomers preferentially incorporate into loaded fibrils. A quantitative relationship between estimated strain, strain-rate, and monomer incorporation is produced.

2. Determination of the Effect of Superimposed Cyclic Strain on the Kinetics of Collagen Polymerization Methods Fibril assembly is initiated as described in Part 1, above. Initial strains of 5%, 10%, and 20%; strain-rates of 0.0 µm/min, 0.25 µm/min, 0.5 µm/min, 0.75 µm/min, and 1.0 µm/min; frequencies of 0.01 Hz, 0.1 Hz, and 1 Hz; and oscillatory strain amplitudes of 0%, 2.5%, and 5% are used. FITC labeled collagen is injected as described in Part 1, above. Fibrils in the surrounding media are used as unloaded controls. Each experiment is performed 3 times.

Monomer incorporation is assessed as described in Part 1, above, using fluorescence microscopy, DIC and sTEM. Fibril monomer incorporation is a function of static strain, oscillatory strain amplitude and frequency. A quantitative multi-parametric relationship between monomer incorporation and strain parameters is produced.

Results

Preferential assembly of labeled monomers into loaded fibrils is observed. A consistent repeatable relationship between strain, monomer concentration and oscillatory parameters is established.

B. The Mechanochemical Kinetics of Enymatic Degradation of Reconstituted Collagen Networks (RCNs) Exposed to Tensile Strain Strained-collagen fibrils in RCNs resist enzymatic degradation. Resistance is a function of concentration. The two operative forward reaction coefficients (enzyme binding and collagen catalysis) are a function of mechanical strain. Information regarding the rate of catalysis is determined using the methods described below by comparing degradation rates on loaded and unloaded fibrils that are derived from processed optical images.

Methods

RCNs are formed around pipettes as described in Part 1, above. To prevent monomer sliding in fibrils, some of the RCNs are cross-linked by incubation under 0.1% riboflavin phosphate-20% dextran T 500 solution for 1 min before photosensitive activation under UVA irradiation (370 nm, 3 mW/cm$^2$) for 30 mins. Media is slowly exchanged with 12 volumes at approximately 1 µl/min to avoid structural disturbance. Static strains of 5%, 10%, or 20%, and oscillatory strains of ±2.5%, ±5%, or ±10% are applied at frequencies of 0.01, 0.1 or 1 Hz to uncrosslinked or crosslinked gels. Activated MMP-8 or BC containing media is introduced and the kinetics of enzymatic degradation is directly observed. Enzyme titrations begin at 0.1× the concentration of available monomers and expanded using a binary search, and the threshold concentration is determined at which only unloaded fibrils are removed. Experiments at the final titrated concentrations for each parameter set are repeated 3 times.

DIC optical imaging is used to track the rate fibril degradation. Curves of fibril DIC signal loss were produced by running DIC images through a Fourier transform edge detector followed by integration of observed edges. The results were qualitatively consistent with observer estimates of fibril loss rates. TEM is used to examine fibril morphology. Optionally, MMP-8 cleavage is confirmed using SDS-PAGE.

Results

A threshold concentration of enzyme is determined below at which loaded fibrils are not affected. Until that concentration is reached, a clear relationship between strain, strain-amplitude, frequency and degradation rates is observed for each enzyme. Higher strains lead to lower degradation rates for concentrations of enzyme above "threshold". The crosslinked fibrils have an increased resistance to enzymatic attack.

C. "Growing" an Aligned, Fibrillar, Collagenous Array

Connective tissues in vivo form mechanically-stable, aligned structures through a combination of strain-dependent enzymatic degradation and polymerization. Organized collagenous tissues are produced in vitro by applying appropriate strain in the presence of excess monomer and an appropriate concentration of enzymes. This "mimics" the growth process of an aligned collagenous structure.

Methods

Figure 24:
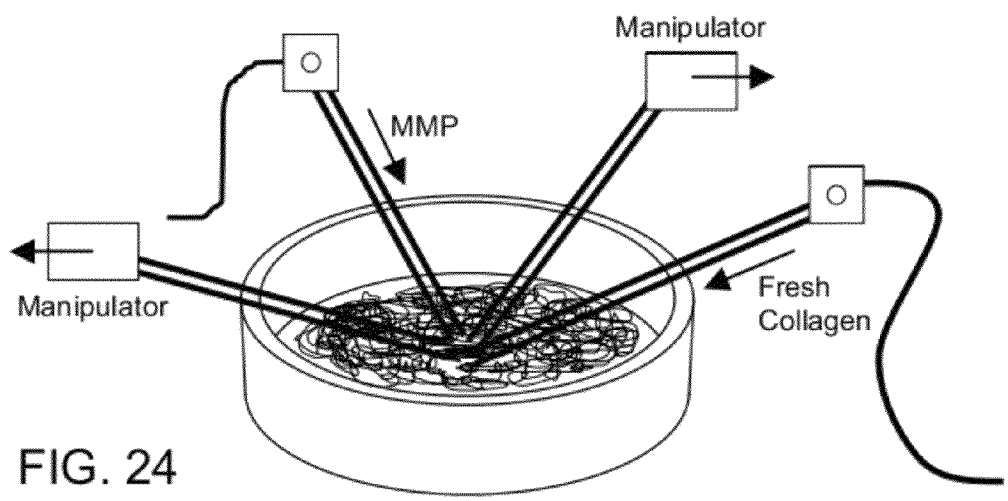
FIG. 24 is a diagrammatic representation of a chamber modified to facilitate collagenous tissue growth.

The chamber described in Part A, above, is modified (see FIG. 24) to allow continuous addition of monomer and enzyme. As shown in the FIG. 24, two micropipettes stretch collagen fibrils while an additional two micropipettes provide a fresh supply of collagen monomers and activated MMP into the reaction buffer. To accommodate four micropipettes, the chamber volume is increased to 80 µL primarily by increasing the diameter. The initial volume of collagen during polymerization in between the pipettes is kept at 20 µL. In the growth phase, the strain regime (rate, frequency and amplitudes), fresh monomer injection (rates and concentrations), and enzyme concentrations are initially determined from the results.

Growth of the collagen construct is directly observed with live DIC microscopy. Polarization microscopy is used to assess the alignment of the construct periodically during the run. The detailed morphology of the structure formed between the pipettes is studied using sTEM.

Results

The preferential removal of unloaded collagen combined with the preferential incorporation of monomer into loaded fibrils yields a load-adapted, aligned structure capable of "growth".

Example 12

The Relationship between Applied Mechanical Load and the Binding Affinity and Cleavage Rate Coefficient of Single Type I Collagen Monomers Application of a tensile load directly to single Type I collagen monomers reduces the effective cleavage rate by specific collagenolytic enzymes (bacterial collagenase, cathepsin-K and matrix metalloproteinases) compared to unloaded controls. This is demonstrated by exposing multiple collagen molecules, in parallel, to degrading enzymes in a custom single molecule magnetic force assay.

Type I human collagen, covalently attached at either end to a superparamagnetic (SPM) bead and a glass slide surface, is loaded via a uniform magnetic field. The time to cleavage is estimated from probability distributions of collagen-tethered SPM bead ejection from the glass surface following addition of cleavage enzymes. The magnetic field strength is varied to alter the time to cleavage. The relationship between load and effective cleavage rate and the relationship between load and the time to complex formation (binding affinity) are determined.

A. Quantitative Relationship Between Load and Effective Rate of Collagen Monomer Cleavage for Various Collagenolytic Enzymes Methods Commercially available recombinant Type I human collagen (RhCl-003, Fibrogen, San Francisco, Calif.) is tethered between antibody functionalized superparamagnetic beads and a glass surface. For bead preparation, SPM beads (1.05±0.02 µm diameter, Invitrogen, Carlsbad, Calif.) are functionalized with antibodies to the C-terminus telopeptide of human collagen. The antibodies are attached to the beads via an EDAC linker using the PolyLink Protein Coupling Kit (Polysciences, Inc., Warrington, Pa.). LF-67 Human αI(1) carboxyl-telopeptide is added to EDAC linker coated beads in solution to allow antibody binding. The antibody functionalized beads are blocked with BSA and aggregation is minimized by exposure to Triton-X100.

The antibody functionalized beads are then exposed to collagen solution to promote binding. For glass preparation, 40 mm #1 borosilicate glass slides are plasma cleaned and silanized followed by direct addition of the linker GMBS (N-[g-maleimidobutyryloxy]succinimide ester)[GMBS, Pierce, Rockford, Ill.]. LF-116 Human α2(I) amino-telopeptide mixed with 10 ml 1% BSA/PBS solution is used to functionalize the glass. For antibody optimization, antibody dilutions of 1:100, 1:250, 1:500, 1:1000, 1:2000 and 1:5000 are tested and optimized, and optionally expanded into a binary search. These preliminary experiments are conducted by direct ELISA.

To apply mechanical load, the antibody-coated coverslip is placed into a microscope-mounted, closed-cell, flow chamber (FCS2, Bioptechs, Butler, Pa.) and exposed to the collagen-coated beads for incubation (1 hr at 25° C.). A stack of five neodymium magnets, which are calibrated for field strength vs. distance using Stoke's drag on a sphere, are positioned to produce a 10 pN force on the SPM beads. Collagen molecules reach their contour length of 300 nm at this level of applied load, and untethered beads are removed. The image plane of the microscope is set to the plane of the centerline of the tethered beads (nominally 800 nm above glass surface). Activated cleavage enzyme is introduced to the chamber at a rate and concentration that minimizes disturbance, yet provides rapid transport. Applied loads begin at a level that does not elongate a collagen monomer past its entropic regime (about 2 pN) and is extended into the elastic regime >10 pN. Load is increased depending on the detected sensitivity of the collagen/enzyme complex. To achieve forces greater than 10 pN, SPM beads of diameter greater than 1 µm are used. Controls are run with heat-inactivated cleavage enzyme. These experiments are repeated to include bacterial collagenase, MMP-1, MMP-8, MMP-13 (all Sigma, Mo.), and cathepsin-K (Biomol International Inc., PA). At least five different loads per enzyme concentration will be run and three different enzyme concentrations are run per load. Experiments are repeated three times.

For cleavage events, beads are tracked optically under 40× magnification on a TE2000 Nikon microscope (Nikon, Tokyo, Japan) using a Photonics CoolSNAP black and white CCD camera at one second intervals. Each enzyme vs. force experimental run produces population data that relate the time blocks to the number of ejected beads during that time block. The position of the peak of this population curve is the effective cleavage rate. For assessment of stress measurements, though the magnetic stack is calibrated, the dipole moment of each SPM bead can vary. To determine the applied force with greater accuracy, the Brownian motion of the tethered bead is analyzed. The force on the collagen is then determined using the following formula, where z is the average end-to-end extension length of the molecule, 300 nm, and δx is the lateral Brownian excursion of the bead center:

$$F = \frac{k_s T(z)}{((\delta x)^2)}$$

Z position is determined using the method described in Part B, below.

A relationship is determined between cleavage rate and mechanical load/concentration for every enzyme that is tested.

Results

Increasing tensile load on collagen monomers increases the time to cleavage.

B. Quantifying the Effect of Tensile Mechanical Load on the Binding Rate Coefficient Governing Collagen/Cleavage Enzyme Complex Formation Methods Quantum dots (Invitrogen, Carlsbad, Calif.) are prepared according to the manufacturer's protocol, and bound to GMBS in the same fashion as antibody attachment as described in Part A, above. During a binding event, the MMP alters the length, z, of the collagen monomer or alters the Brownian excursion distance, δx. Collagen length change is measured as follows. Since the refractive index of the quantum dot and the experimental media are different, the point spread function (PSF) of the quantum dots varies based on depth in the media. By using a model of the predicted point spread function developed by Aquet et al. (*Confocal, Multiphoton, and Nonlinear Microscope Imaging II* (2005)), the z-position is determined with precision in the nanometer range by fitting the actual PSF to the model. A 60× objective is focused onto the collagen tethered SPM beads with the quantum dots glass-bound position out of focus. The quantum dot positions are determined with greater accuracy using defocused particles. Bead position relative to the focal plane is estimated by fitting a circle to the outline of the bead, and the PSF fit determines the position of the quantum dot. This distance is monitored for changes as enzyme is introduced into the chamber. Brownian motion changes are measured as follows. Since the catabolic enzymes bind tightly to the collagen molecule (stiffening) and comprise a significant percentage of collagen's molecular weight (33% for BC), binding alters the Brownian excursion. Thus, x-y position is monitored following the introduction of enzyme to the chamber.

A high-resolution camera (Retiga EXL, QI Imaging, 1394b, Mono, 14 bit cooled OC) is added to a Nikon TE2000E microscope, which enables vertical, spatial and temporal resolution to a level that allows detection of changes in the relative position of particles on the order of nanometers. Bead and quantum dot positions are reported as functions of time, and the relative displacement curves are examined for abrupt changes.

Results

Strain applied to collagen monomers modifies the binding rate coefficient and the cleavage rate coefficient. Effective cleavage rates of collagen by enzymes are the result of a binding and cleavage event. Both of these events involve physical interaction of the enzyme with specific sites on the collagen monomer and are affected by the application of strain. The detection of the binding events allows a direct determination of the extent each event (binding or cleavage) is influenced by mechanical strain.

C. Effect of Mechanical Force on the Physical Behavior of Collagen Molecular Structure and on Hierarchical Collagen Assemblies Methods Atomistic-based multi-scale modeling is used for the chemomechanical behavior of tropocollagen monomers and the hierarchical structure of collagen fibrils, focusing on the effect of strain, enzymatic activity, and the coupling between strain and cleavage probability. The mechanical properties of tropocollagen molecules are investigated using steered molecular dynamics simulations using both a CHARMM force field as well as the new first principles based reactive force field ReaxFF. The ReaxFF model includes a first principles based description of all chemical bonds in the system (including breaking and formation of covalent bonds). This method captures chemomechanical coupling. The ReaxFF model bridges the scale from first principles quantum mechanical descriptions (limited to <200 atoms) to empirical CHARMM-like force fields and molecular mechanics models. In ReaxFF, the energy of atoms and molecules and their charges is not calculated based on simple distance-energy relations, but instead, is calculated dependent on the quantum mechanical state or bond orders.

The software THeBuScr (Triple-Helical collagen Building Script) is used to build a model of the tropocollagen molecule. This builder enables the generation of tropocollagen monomers with any desired sequence. The sequence is chosen based on those structures relevant to the cleavage domain in the collagen molecule. The MMP enzyme structures are taken from the protein data bank (PDB).

The tropocollagen molecule is subjected to traction along its principal axis using steered molecular dynamics (SMD). Other studies are focused on coupling between mechanical strain and the effect on the collagen network formation and stability. The interaction of a single tropocollagen molecule with MMP is studied under varying stain. The energy landscape of these atomic mechanisms is mapped and quantitative information is provided of how strain affects the interaction of the enzyme with the collagen. This series of computational experiments discerns that binding affinity and/or cleavage ability (modeled as the change in energy used to separate an alpha chain from the triple helix) is affected by the applied load. Using a combination with mesoscale simulations, entropic effects are captured that may play a key role at longer time-scales and, in the case of longer tropocollagen monomer sections, during assembly processes. The interaction and assembly of a large ensemble of >10,000 tropocollagen monomers is simulated under varying mechanical strain and under varying enzymatic activity.

Example 13

Producing Organized Collagen by Strain-Stabilization Effect

Collagen fibrils are protected from enzymatic attack if they are "strained" appropriately. The methods described in Example 2 are modified by applying a strain field to the construct, creating a strain on the order of 1.5% to 4% where fibril retention is desired. Fibrils outside this range are preferentially degraded. Controllable strain is created by fixing the organized collagen gels to moveable grips or functionalized surfaces (see, e.g., Ruberti et al., *Biochem. Biophys. Res. Commun.* 336:483-489 (2005)). FIG. 25 shows two devices that are used to apply known loads to collagen constructs.

Both devices allow high-powered optical observation and media access for enzyme and monomer cycling. These devices create uniaxial and tangential loads suitable for the production tendon-like and cornea-like organization.

EQUIVALENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. A method of producing an organized array of collagen fibrils, the method comprising:
   contacting a template with a solution comprising collagen monomers from collagen fibrils in the solution;
   applying a tension to a plurality of collagen fibrils in the solution, where the tension is controlled to generate a strain on the plurality of collagen fibrils of about 1% to about 10% such that controlled load on the collagen monomers is produced; and
   contacting the plurality of collagen fibrils with a collagen lytic protease, thereby producing the organized array of collagen fibrils form the plurality of collagen fibrils.

2. The method of claim 1, further comprising neutralizing the pH of the solution in contact with the template.

3. The method of claim 2, further comprising neutralizing the pH of the solution in contact with the template at about 10° C. to about 39° C.

4. The method of claim 1, wherein the tension is applied to both ends of the plurality of collagen fibrils.

5. The method of claim 4, further comprising adding supplemental collagen monomers to the solution continuously during application of the tension.

6. The method of claim 5, wherein the collagen lytic protease and the supplemental collagen monomers are added simultaneously to the solution.

7. The method of claim 5, wherein the collagen lytic protease and the supplemental collagen monomers are added sequentially to the solution.

8. The method of claim 5, wherein the collagen lytic protease and the supplemental collagen are added more than once to the solution.

9. The method of claim 1, further comprising organizing the array of collagen fibrils into a tissue.

10. The method of claim 5 further comprising continuously extending a collagen fibrillar structure at a rate of from about 0.1 μm/min to about 100 μm/min.

11. The method of claim 10 further comprising adding collagen lytic protease to the solution while extending the collagen fibrillar structure.

12. The method of either claim 10 or 11 further comprising extending the collagen fibrillar structure in the presence of a proteoglycan.

13. The method of claim 10 further comprising extending the collagen fibrillar structure in the presence of a co-nonsolvency agent.

14. The method of claim 12 further comprising extending the collagen fibrillar structure in the presence of a co-nonsolvency agent.

15. The method of claim 1, wherein the load on each collagen monomer is from 1.0 piconewtons to a 10.0 piconewtons.

* * * * *

UNITED STATES PATENT AND TRADEMARK OFFICE
CERTIFICATE OF CORRECTION

PATENT NO. : 8,338,570 B2
APPLICATION NO. : 12/901286
DATED : December 25, 2012
INVENTOR(S) : Nima Saeidi et al.

It is certified that error appears in the above-identified patent and that said Letters Patent is hereby corrected as shown below:

In The Claims

Column 49, line 19, Change "from collagen" to "to form collagen"

Column 49, line 23, Change "controlled load" to "a controlled load"

Column 49, line 27, Change "form the plurality" to "from the plurality"

Signed and Sealed this
Third Day of May, 2016

Michelle K. Lee
*Director of the United States Patent and Trademark Office*